(12) United States Patent
Inglese et al.

(10) Patent No.: US 10,808,010 B2
(45) Date of Patent: Oct. 20, 2020

(54) PEPTIDE INHIBITORS OF PHOSPHOGLYCERATE MUTASE AND METHODS OF USE

(71) Applicants: The United States of America, as represented by the Secretary, Dept. of Health and Human Services, Bethesda, MD (US); The University of Tokyo, Tokyo (JP); New England Biolabs, Inc., Ipswich, MA (US)

(72) Inventors: James Inglese, Bethesda, MD (US); Patricia Dranchak, Gaithersburg, MD (US); Ryan MacArthur, Odenton, MD (US); Hiroaki Suga, Tokyo (JP); Hao Yu, Tokyo (JP); Clotilde Carlow, South Hamilton, MA (US); Zhiru Li, Lexington, MA (US)

(73) Assignees: The United States of America, as represented by the Secretary, Department of Health and Human Services, Bethesda, MD (US); The University of Tokyo, Tokyo (JP); New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 16/324,424

(22) PCT Filed: Aug. 10, 2017

(86) PCT No.: PCT/US2017/046228
§ 371 (c)(1),
(2) Date: Feb. 8, 2019

(87) PCT Pub. No.: WO2018/031730
PCT Pub. Date: Feb. 15, 2018

(65) Prior Publication Data
US 2019/0169234 A1 Jun. 6, 2019

Related U.S. Application Data

(60) Provisional application No. 62/373,835, filed on Aug. 11, 2016.

(51) Int. Cl.
| | |
|---|---|
| *C07K 7/64* | (2006.01) |
| *C07K 7/08* | (2006.01) |
| *C07K 7/06* | (2006.01) |
| *C07K 7/56* | (2006.01) |
| *C07K 14/00* | (2006.01) |
| *A61P 33/10* | (2006.01) |
| *A61K 38/12* | (2006.01) |
| *A61K 45/06* | (2006.01) |
| *A61K 38/00* | (2006.01) |

(52) U.S. Cl.
CPC ............... *C07K 7/64* (2013.01); *A61K 38/12* (2013.01); *A61K 45/06* (2013.01); *A61P 33/10* (2018.01); *C07K 7/06* (2013.01); *C07K 7/08* (2013.01); *C07K 7/56* (2013.01); *C07K 14/00* (2013.01); *A61K 38/00* (2013.01); *Y02A 50/421* (2018.01); *Y02A 50/473* (2018.01)

(58) Field of Classification Search
CPC ............... A61K 38/00; A61K 39/3955; A61K 39/0258; C07K 16/40; C07K 16/1275; C07K 16/20; C07K 14/4354; C07K 14/44; G01N 2333/195; G01N 2333/245
See application file for complete search history.

(56) References Cited

U.S. PATENT DOCUMENTS 6,472,368 B1 10/2002 Doherty et al.

FOREIGN PATENT DOCUMENTS

| WO | WO 2009/055054 | 4/2009 |
| WO | WO 2014/138429 | 9/2014 |

OTHER PUBLICATIONS

Cofactor-Independent Phosphoglycerate Mutase from Nematodes Has Limited Druggability, as Revealed by Two High-Throughput Screens. PLoS Negl Trop Dis. 2014; 8(1): e2628. (Year: 2014).*
Blackburn et al., "Trypanosomatid phosphoglycerate mutases have multiple conformational and oligomeric states," *Biochemical and Biophysical Research Communications*, vol. 450, pp. 936-941, 2014 (including Supplementary Online Data).
Crowther et al., "Cofactor-Independent Phosphoglycerate Mutase from Nematodes Has Limited Druggability, as Revealed by Two High-Throughput Screens," *PLOS Neglected Tropical Diseases*, 8(1):e2628, 2014 (9 pages).
Driggers et al., "The exploration of macrocycles for drug discovery—an underexploited structural class," *Nature Reviews Drug Discovery*, vol. 7, pp. 608-624, 2008.

(Continued)

*Primary Examiner* — Soren Harward
*Assistant Examiner* — Jia-Hai Lee
(74) *Attorney, Agent, or Firm* — Klarquist Sparkman, LLP

(57) ABSTRACT

Disclosed herein are isolated peptides inhibit activity of a cofactor-independent phosphoglycerate mutase. In some examples, the isolated peptide is 6-20 amino acids long and includes the amino acid sequence of any one of SEQ ID NOs: 1-22 or 54, an analog or derivative thereof, or a pharmaceutically acceptable salt or ester thereof. In some examples, the peptide is a cyclic peptide with an N-terminal ring of 6-15 amino acids (for example, 6-10 amino acids) and a C-terminal linear portion of 1-9 amino acids (for example, 3-8 amino acids. Also disclosed h are methods of treating or inhibiting an infection in a subject, including administering to the subject an effective amount of a composition including one or more of the disclosed peptides, or analogs or derivative thereof, or pharmaceutically acceptable salts or esters thereof.

16 Claims, 36 Drawing Sheets
Specification includes a Sequence Listing.

(56) References Cited

OTHER PUBLICATIONS

Roychowdhury et al., "Complete catalytic cycle of cofactor-independent phosphoglycerate mutase involves a spring-loaded mechanism," *FEBS J.*, vol. 282, pp. 1097-1110, 2015.
Yu et al., "Macrocycle peptides delineate locked-open inhibition mechanism for microorganism phosphoglycerate mutases," *Nature Communications*, 8:14932, 2017 (13 pages).

* cited by examiner

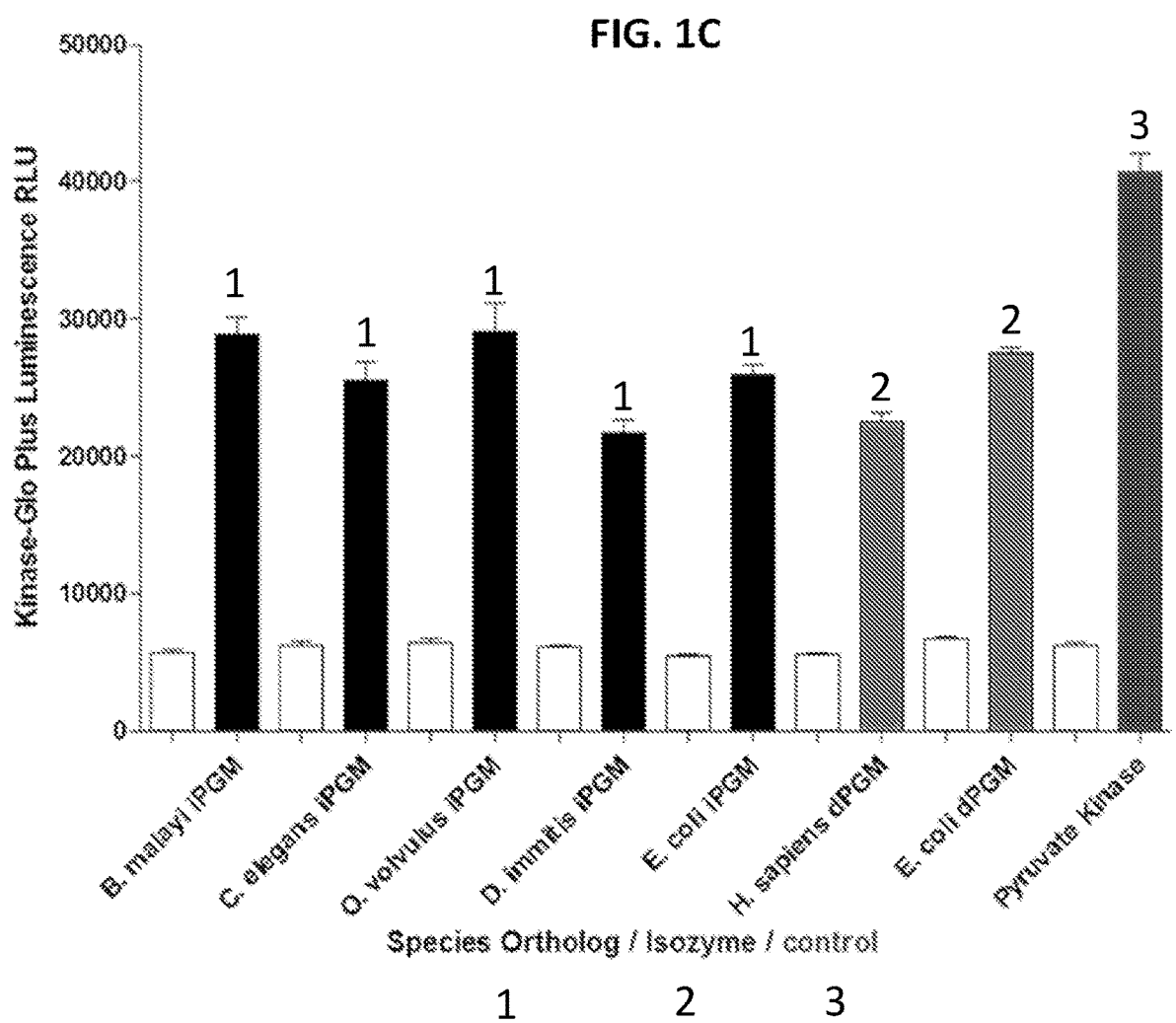

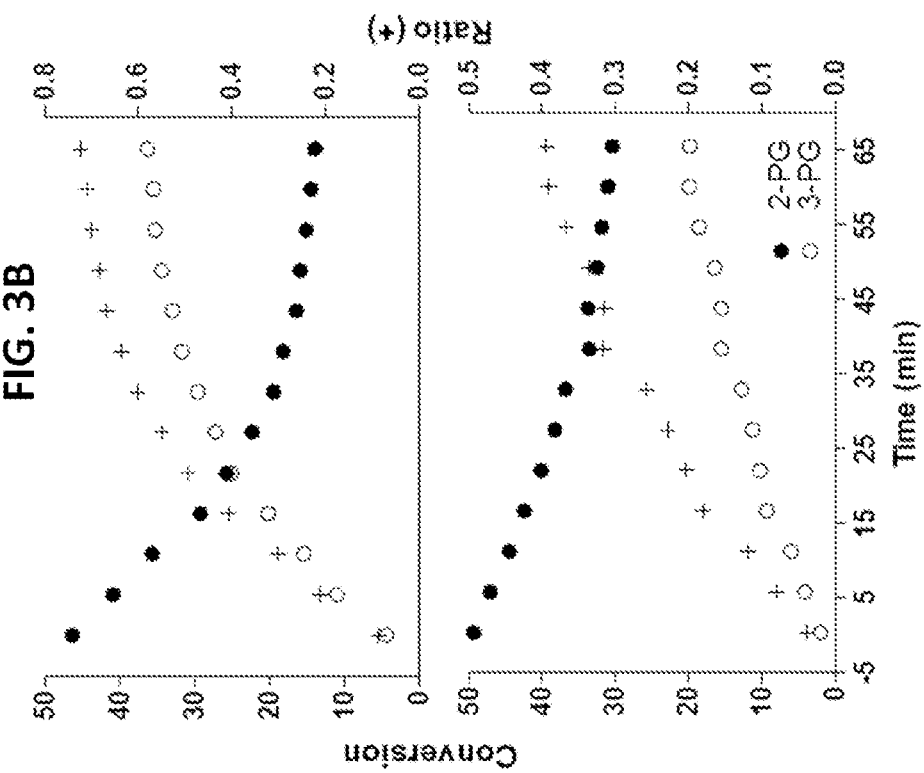
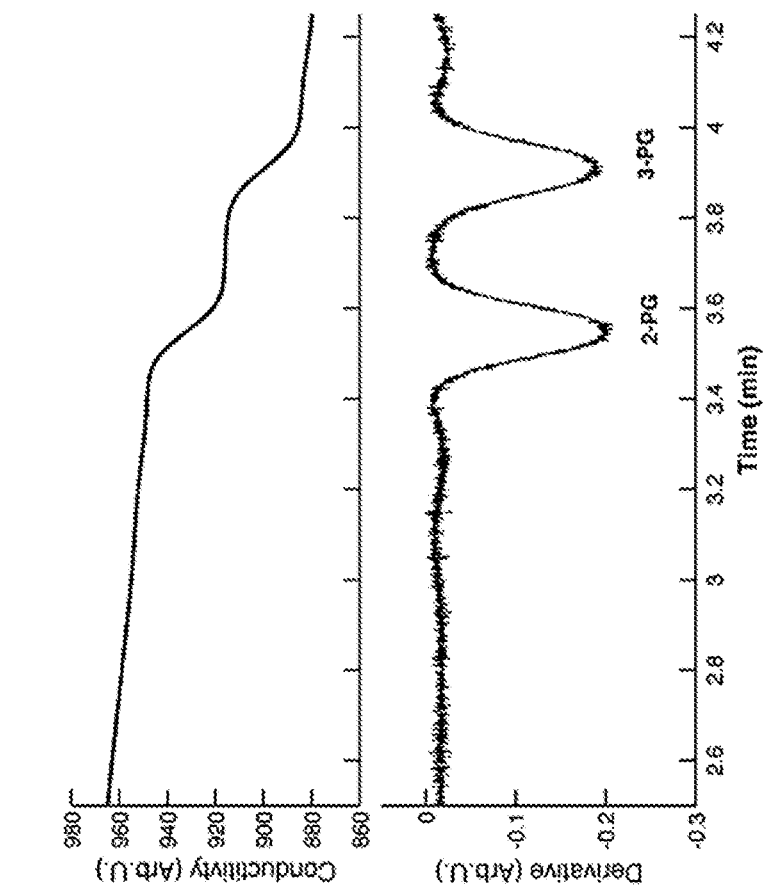
FIG. 3A
FIG. 3B

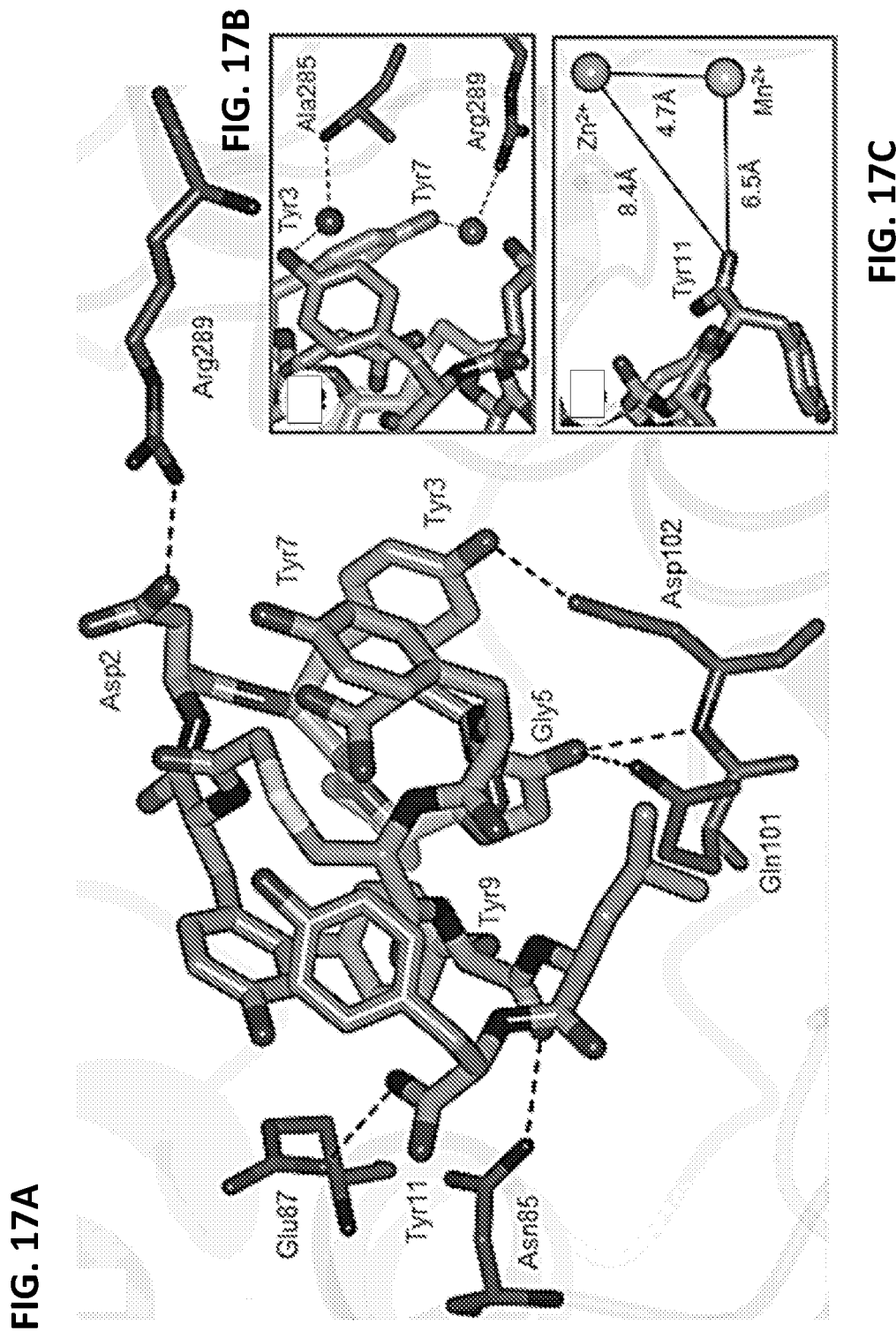

FIG. 19B

|  | Domain A region (N-terminus) | Hinge 1 | Domain B region | |
|---|---|---|---|---|
| C. elegans | GLHVGLPEGLMGNSEVGHLN | IGAGRVIYQD | IVRINLAVKNNKFVTNESLVDAC | 125 |
| B. malayi | GLHVGLPEGLMGNSEVGHLN | IGAGRVVYQD | IVRINLAVKNKTLVENKHLKEAA | |
| O. volvulus | GLHVGLPEGLMGNSEVGHLN | IGAGRVVYQD | IVRINLAVKNKTLVENKHLKEAA | |
| D. immitis | GLHVGLPEGLMGNSEVGHLN | IGAGRVVYQD | IVRINLAVKNKTLVENKHLKEAA | |
| E. coli | GLEVGLPDRQMGNSEVGHVNL | GAGRIVYQD | LTRLDVEIKDRAFFANPVLTGAV | |
| consensus | :**:*:**:* | :**:: | ::.****:.:*:*:*:.: * | |

|  | Domain B region | Hinge 2 | | |
|---|---|---|---|---|
| C. elegans | NDDTIIFFDYRADRMREISAAM | QVYGMTQYKAE | FPFKSLFPPASNKNVLAE | 342 |
| B. malayi | DGDTLIFFDYRADRMREITECM | QVIGMTQYKAE | FTFPALFPPESHKNVLAE | |
| O. volvulus | DGDTLIFFDYRADRMREITECM | QVIGMTQYKAE | FTFPALFPPESHKNVLAE | |
| D. immitis | DGDTLIFFDYRADRMREITECM | QVIGMTQYKAE | FTFPALFPPESHKNVLAE | |
| E. coli | DGDALIFMNFRADRAREITRAF | DFVMLTEYAAD | IKTAVAYPPASLVNTFGE | |
| consensus | :.*:.:::*.**:*..: | :.:.:**:.: | :.:..:* **.*:*.:.* | |

|  | Domain A region (C-terminus) | | | |
|---|---|---|---|---|
| C. elegans | HVTFFFNGGLEKQFEGEEERC | ADHGNAEKMKAP-DGGKHTAHTCYRVPLTLS | | 495 |
| B. malayi | HVTFFFNGGVEKQFANEEERC | ADHGNAEKMMAP-DGSKHTAHTCNLVPFTCS | | |
| O. volvulus | HVTFFFNGGVEKQFENEEERC | ADHGNAEKMMAP-DGGKHTAHTCNLVPFTCS | | |
| D. immitis | HVTFFFNGGVEKQFENEEERC | ADHGNAEKMIAP-DGGKHTAHTCNLVPFTCS | | |
| E. coli | HVTFFFNGGVEESFKGEDRI | ADHGNAEQMRDPATGQAHTNLPVPLIYV | | |
| consensus | ********::.*:.**:* | *******:*: .*.:** .:*:.. * | | |

SEQUENCE LISTING

```
<160> NUMBER OF SEQ ID NOS: 69

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 1

Tyr Asp Tyr Pro Gly Asp His Cys Tyr Leu Tyr Gly Thr Cys Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 2

Tyr Asp Tyr Pro Gly Asp Tyr Cys Tyr Leu Tyr Gly Thr Cys Gly
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc
<222> LOCATION: (1)..(13)
<223> OTHER INFORMATION: cyclic linkage

<400> SEQUENCE: 3

Tyr Ile Thr Leu Ala Asn Pro Phe Arg Ile Leu His Cys Gly
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(13)
<223> OTHER INFORMATION: cyclic linkage

<400> SEQUENCE: 4

Tyr Thr Thr Leu Ala Asn Pro Phe Arg Ile Leu His Cys Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 5

Tyr Asp Tyr Pro Gly Asp Tyr Cys Tyr Leu Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 6

Tyr Asp Tyr Pro Gly Asp Tyr Cys Tyr Leu Tyr Gly Thr Ser Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Tyr Asp Tyr Pro Gly Asp Tyr Ser Tyr Leu Tyr Gly Thr Cys Gly
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MISC_FEATURE
<222> LOCATION: (1)..(1)
<223> OTHER INFORMATION: N-chloroacetyl modification

<400> SEQUENCE: 8

Tyr Asp Tyr Pro Gly Asp Tyr Ser Tyr Leu Tyr
1               5                   10

<210> SEQ ID NO 9
<211> LENGTH: 7
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MISC_FEATURE
<222> LOCATION: (1)..(1)
<223> OTHER INFORMATION: N-chloroacetyl modification

<400> SEQUENCE: 9

Tyr Leu Tyr Gly Thr Cys Gly
1               5

<210> SEQ ID NO 10
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: cyclic linkage

<400> SEQUENCE: 10

Tyr Ser Trp Pro Asn Ala Pro Glu Ile Trp Lys Cys Cys Gly
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(13)
<223> OTHER INFORMATION: cyclic linkage

<400> SEQUENCE: 11

Tyr Asp Leu Arg Thr Pro Trp Leu Lys Arg His Ala Cys Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(12)
<223> OTHER INFORMATION: cyclic linkage

<400> SEQUENCE: 12

Tyr Gln Asn Arg Ser Ile Trp Leu Tyr Gly Cys Cys Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
```

```
<223> OTHER INFORMATION: cyclic linkage

<400> SEQUENCE: 13

Tyr Leu Glu Trp Pro Asn Cys Asn Thr Cys Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: cyclic linkage

<400> SEQUENCE: 14

Tyr Leu Asp Trp Pro Asn Cys Ser Thr Cys Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: cyclic linkage

<400> SEQUENCE: 15

Tyr Pro Glu Trp Pro Asn Cys Ser Thr Cys Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(7)
<223> OTHER INFORMATION: cyclic linkage

<400> SEQUENCE: 16

Tyr Ala Val Trp Pro Asn Cys Arg Thr Cys Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 17

Tyr Asp Tyr Pro Gly Asp Tyr Cys Tyr Leu Tyr Gly Thr Cys
1               5                   10

<210> SEQ ID NO 18
<211> LENGTH: 13
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 18

Tyr Asp Tyr Pro Gly Asp Tyr Cys Tyr Leu Tyr Gly Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 19

Tyr Asp Tyr Pro Gly Asp Tyr Cys Tyr Leu Tyr Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage

<400> SEQUENCE: 20

Tyr Asp Tyr Pro Gly Asp Tyr Cys Tyr Leu
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MISC_FEATURE
<222> LOCATION: (1)..(1)
<223> OTHER INFORMATION: N-chloroacetyl modification
<220> FEATURE:
<221> NAME/KEY: MISC_FEATURE
<222> LOCATION: (1)..(8)
<223> OTHER INFORMATION: cyclic linkage

<400> SEQUENCE: 21

Tyr Asp Tyr Pro Gly Asp Tyr Cys Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: D-Tyrosine
<220> FEATURE:
<221> NAME/KEY: MISC_FEATURE
<222> LOCATION: (1)..(1)
<223> OTHER INFORMATION: N-chloroacetyl modification
<220> FEATURE:
<221> NAME/KEY: MISC_FEATURE
<222> LOCATION: (1)..(8)
<223> OTHER INFORMATION: cyclic linkage

<400> SEQUENCE: 22

Tyr Asp Tyr Pro Gly Asp Tyr Cys
1               5

<210> SEQ ID NO 23
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 23
atgagttggc ctaatgctcc ggagatttgg aagtgttgcg gc                           42

<210> SEQ ID NO 24
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 24
atggatctta ggacgccttg gttgaagcgg catgcttgcg gc                           42

<210> SEQ ID NO 25
<211> LENGTH: 39
<212> TYPE: DNA
<213> ORGANISM: Artificial Sequence
<220> FEATURE:
<223> OTHER INFORMATION: Synthetic nucleic acid

<400> SEQUENCE: 25
atgcagaata ggtcgatttg gctgtatggt tgttgcggc                               39

<210> SEQ ID NO 26
<211> LENGTH: 33
<212> TYPE: DNA
<213> ORGANISM: Artificial Sequence
<220> FEATURE:
<223> OTHER INFORMATION: Synthetic nucleic acid

<400> SEQUENCE: 26
atgcttgagt ggccgaattg taatacttgc ggc                                     33

<210> SEQ ID NO 27
<211> LENGTH: 33
<212> TYPE: DNA
<213> ORGANISM: Artificial Sequence
<220> FEATURE:
<223> OTHER INFORMATION: Synthetic nucleic acid

<400> SEQUENCE: 27
atgcttgatt ggcctaattg tagtacttgc ggc                                     33
```

<210> SEQ ID NO 28
<211> LENGTH: 33
<212> TYPE: DNA
<213> ORGANISM: Artificial Sequence
<220> FEATURE:
<223> OTHER INFORMATION: Synthetic nucleic acid

<400> SEQUENCE: 28
atgcctgagt ggccgaattg tagtacttgc ggc        33

<210> SEQ ID NO 29
<211> LENGTH: 33
<212> TYPE: DNA
<213> ORGANISM: Artificial Sequence
<220> FEATURE:
<223> OTHER INFORMATION: Synthetic nucleic acid

<400> SEQUENCE: 29
atggctgttt ggcctaattg taggacgtgc ggc        33

<210> SEQ ID NO 30
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 30
atggattatc cgggtgatca ttgttatctt tatgggacct gcggc        45

<210> SEQ ID NO 31
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 31
atggattatc cgggtgatca ttgttatctt tatgggactt gcggc        45

<210> SEQ ID NO 32
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 32
atggattatc ctggtgatca ttgttatctt tatgggactt gcggc        45

<210> SEQ ID NO 33
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 33
atggattatc caggtgatca ttgttatctt tatgggacct gcggc        45

<210> SEQ ID NO 34
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 34
atggattatc cgggagatca ttgttatctt tatgggactt gcggc            45

<210> SEQ ID NO 35
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 35
atggattatc cgggagatca ttgttatctt tatgggacct gcggc            45

<210> SEQ ID NO 36
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 36
atggattatc caggtgatca ttgttatctt tatgggacat gcggc            45

<210> SEQ ID NO 37
<211> LENGTH: 45
<212> TYPE: DNA
<213> ORGANISM: Artificial Sequence
<220> FEATURE:
<223> OTHER INFORMATION: Synthetic nucleic acid

<400> SEQUENCE: 37
atggattatc cgggtgatta ttgttatctt tatgggactt gcggc            45

<210> SEQ ID NO 38
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 38
atgattacgc ttgcgaatcc ttttcgtatt ttgcattgcg gc               42

<210> SEQ ID NO 39
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 39
atgattacgc ttgcgaatcc ttttcgtatt ttgcactgcg gc               42

<210> SEQ ID NO 40
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 40
atgattacgc ttgcgaatcc ttttcgcatt ttgcactgcg gc               42

<210> SEQ ID NO 41
<211> LENGTH: 42

-continued

```
<212> TYPE: DNA
<213> ORGANISM: Artificial Sequence
<220> FEATURE:
<223> OTHER INFORMATION: Synthetic nucleic acid

<400> SEQUENCE: 41
atgattacgc ttgcgaatcc gttccgtatt ttgcattgcg gc                        42

<210> SEQ ID NO 42
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 42
atgattacgc ttgcgaatcc ttttcgcatt ttgcattgcg gc                        42

<210> SEQ ID NO 43
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 43
atgattacgc ttgcgaatcc ttttcgtatt ttacattgcg gc                        42

<210> SEQ ID NO 44
<211> LENGTH: 42
<212> TYPE: DNA
<213> ORGANISM: Artificial Sequence
<220> FEATURE:
<223> OTHER INFORMATION: Synthetic nucleic acid

<400> SEQUENCE: 44
atgactacgc ttgcgaatcc ttttcgtatc ttgcattgcg gc                        42

<210> SEQ ID NO 45
<211> LENGTH: 539
<212> TYPE: PRT
<213> ORGANISM: Caenorhabditis elegans

<400> SEQUENCE: 45

Met Phe Val Ala Leu Gly Ala Gln Ile Tyr Arg Gln Tyr Phe Gly Arg
1               5                   10                  15

Arg Gly Met Ala Met Ala Asn Asn Ser Ser Val Ala Asn Lys Val Cys
            20                  25                  30

Leu Ile Val Ile Asp Gly Trp Gly Val Ser Glu Asp Pro Tyr Gly Asn
        35                  40                  45

Ala Ile Leu Asn Ala Gln Thr Pro Val Met Asp Lys Leu Cys Ser Gly
    50                  55                  60

Asn Trp Ala Gln Ile Glu Ala His Gly Leu His Val Gly Leu Pro Glu
65                  70                  75                  80

Gly Leu Met Gly Asn Ser Glu Val Gly His Leu Asn Ile Gly Ala Gly
                85                  90                  95

Arg Val Ile Tyr Gln Asp Ile Val Arg Ile Asn Leu Ala Val Lys Asn
            100                 105                 110

Asn Lys Phe Val Thr Asn Glu Ser Leu Val Asp Ala Cys Asp Arg Ala
        115                 120                 125

Lys Asn Gly Asn Gly Arg Leu His Leu Ala Gly Leu Val Ser Asp Gly
    130                 135                 140
```

```
Gly Val His Ser His Ile Asp His Met Phe Ala Leu Val Lys Ala Ile
145                 150                 155                 160

Lys Glu Leu Gly Val Pro Glu Leu Tyr Leu His Phe Tyr Gly Asp Gly
                165                 170                 175

Arg Asp Thr Ser Pro Asn Ser Gly Val Gly Phe Leu Glu Gln Thr Leu
            180                 185                 190

Glu Phe Leu Glu Lys Thr Thr Gly Tyr Gly Lys Leu Ala Thr Val Val
        195                 200                 205

Gly Arg Tyr Tyr Ala Met Asp Arg Asp Asn Arg Trp Glu Arg Ile Asn
210                 215                 220

Val Ala Tyr Glu Ala Met Ile Gly Gly Val Gly Glu Thr Ser Asp Glu
225                 230                 235                 240

Ala Gly Val Val Glu Val Val Arg Lys Arg Tyr Ala Ala Asp Glu Thr
                245                 250                 255

Asp Glu Phe Leu Lys Pro Ile Ile Leu Gln Gly Glu Lys Gly Arg Val
            260                 265                 270

Gln Asn Asp Asp Thr Ile Ile Phe Asp Tyr Arg Ala Asp Arg Met
        275                 280                 285

Arg Glu Ile Ser Ala Ala Met Gly Met Asp Arg Tyr Lys Asp Cys Asn
290                 295                 300

Ser Lys Leu Ala His Pro Ser Asn Leu Gln Val Tyr Gly Met Thr Gln
305                 310                 315                 320

Tyr Lys Ala Glu Phe Pro Phe Lys Ser Leu Phe Pro Pro Ala Ser Asn
                325                 330                 335

Lys Asn Val Leu Ala Glu Trp Leu Ala Glu Gln Lys Val Ser Gln Phe
            340                 345                 350

His Cys Ala Glu Thr Glu Lys Tyr Ala His Val Thr Phe Phe Phe Asn
        355                 360                 365

Gly Gly Leu Glu Lys Gln Phe Glu Gly Glu Glu Arg Cys Leu Val Pro
370                 375                 380

Ser Pro Lys Val Ala Thr Tyr Asp Leu Gln Pro Glu Met Ser Ala Ala
385                 390                 395                 400

Gly Val Ala Asp Lys Met Ile Glu Gln Leu Glu Ala Gly Thr His Pro
                405                 410                 415

Phe Ile Met Cys Asn Phe Ala Pro Pro Asp Met Val Gly His Thr Gly
            420                 425                 430

Val Tyr Glu Ala Ala Val Lys Ala Cys Glu Ala Thr Asp Ile Ala Ile
        435                 440                 445

Gly Arg Ile Tyr Glu Ala Thr Gln Lys His Gly Tyr Ser Leu Met Val
450                 455                 460

Thr Ala Asp His Gly Asn Ala Glu Lys Met Lys Ala Pro Asp Gly Gly
465                 470                 475                 480

Lys His Thr Ala His Thr Cys Tyr Arg Val Pro Leu Thr Leu Ser His
                485                 490                 495

Pro Gly Phe Lys Phe Val Asp Pro Ala Asp Arg His Pro Ala Leu Cys
            500                 505                 510

Asp Val Ala Pro Thr Val Leu Ala Ile Met Gly Leu Pro Gln Pro Ala
        515                 520                 525

Glu Met Thr Gly Val Ser Ile Val Gln Lys Ile
530                 535

<210> SEQ ID NO 46
<211> LENGTH: 515
```

<212> TYPE: PRT
<213> ORGANISM: Brugia malayi

<400> SEQUENCE: 46

```
Met Ala Glu Ala Lys Asn Arg Val Cys Leu Val Val Ile Asp Gly Trp
1               5                   10                  15

Gly Ile Ser Asn Glu Thr Lys Gly Asn Ala Ile Leu Asn Ala Lys Thr
            20                  25                  30

Pro Val Met Asp Glu Leu Cys Val Met Asn Ser His Pro Ile Gln Ala
        35                  40                  45

His Gly Leu His Val Gly Leu Pro Glu Gly Leu Met Gly Asn Ser Glu
    50                  55                  60

Val Gly His Leu Asn Ile Gly Ala Gly Arg Val Val Tyr Gln Asp Ile
65                  70                  75                  80

Val Arg Ile Asn Leu Ala Val Lys Asn Lys Thr Leu Val Glu Asn Lys
                85                  90                  95

His Leu Lys Glu Ala Ala Glu Arg Ala Ile Lys Gly Asn Gly Arg Met
            100                 105                 110

His Leu Cys Gly Leu Val Ser Asp Gly Gly Val His Ser His Ile Asp
        115                 120                 125

His Leu Phe Ala Leu Ile Thr Ala Leu Lys Gln Leu Lys Val Pro Lys
    130                 135                 140

Leu Tyr Ile Gln Phe Phe Gly Asp Gly Arg Asp Thr Ser Pro Thr Ser
145                 150                 155                 160

Gly Val Gly Phe Leu Gln Gln Leu Ile Asp Phe Val Asn Lys Glu Gln
                165                 170                 175

Tyr Gly Glu Ile Ser Thr Ile Val Gly Arg Tyr Tyr Ala Met Asp Arg
            180                 185                 190

Asp Lys Arg Trp Glu Arg Ile Arg Val Cys Tyr Asp Ala Leu Ile Gly
        195                 200                 205

Gly Val Gly Glu Lys Thr Thr Ile Asp Lys Ala Ile Asp Val Ile Lys
    210                 215                 220

Gly Arg Tyr Ala Lys Asp Glu Thr Asp Glu Phe Leu Lys Pro Ile Ile
225                 230                 235                 240

Leu Ser Asp Glu Gly Arg Thr Lys Asp Gly Asp Thr Leu Ile Phe Phe
                245                 250                 255

Asp Tyr Arg Ala Asp Arg Met Arg Glu Ile Thr Glu Cys Met Gly Met
            260                 265                 270

Glu Arg Tyr Lys Asp Leu Asn Ser Asn Ile Lys His Pro Lys Asn Met
        275                 280                 285

Gln Val Ile Gly Met Thr Gln Tyr Lys Ala Glu Phe Thr Phe Pro Ala
    290                 295                 300

Leu Phe Pro Pro Glu Ser His Lys Asn Val Leu Ala Glu Trp Leu Ser
305                 310                 315                 320

Val Asn Gly Leu Thr Gln Phe His Cys Ala Glu Thr Glu Lys Tyr Ala
                325                 330                 335

His Val Thr Phe Phe Phe Asn Gly Gly Val Glu Lys Gln Phe Ala Asn
            340                 345                 350

Glu Glu Arg Cys Leu Val Val Ser Pro Lys Val Ala Thr Tyr Asp Leu
        355                 360                 365

Glu Pro Pro Met Ser Ser Ala Ala Val Ala Asp Lys Val Ile Glu Gln
    370                 375                 380

Leu His Met Lys Lys His Pro Phe Val Met Cys Asn Phe Ala Pro Pro
385                 390                 395                 400
```

```
Asp Met Val Gly His Thr Gly Val Tyr Glu Ala Ala Val Lys Ala Val
            405                 410                 415

Glu Ala Thr Asp Ile Ala Ile Gly Arg Ile Tyr Glu Ala Cys Lys Lys
            420                 425                 430

Asn Asp Tyr Ile Leu Met Val Thr Ala Asp His Gly Asn Ala Glu Lys
            435                 440                 445

Met Met Ala Pro Asp Gly Ser Lys His Thr Ala His Thr Cys Asn Leu
            450                 455                 460

Val Pro Phe Thr Cys Ser Ser Met Lys Tyr Lys Phe Met Asp Lys Leu
465                 470                 475                 480

Pro Asp Arg Glu Met Ala Leu Cys Asp Val Ala Pro Thr Val Leu Lys
            485                 490                 495

Val Met Gly Val Pro Leu Pro Ser Glu Met Thr Gly Gln Pro Leu Val
            500                 505                 510

Asn Glu Ala
            515

<210> SEQ ID NO 47
<211> LENGTH: 515
<212> TYPE: PRT
<213> ORGANISM: Onchocerca volvulus

<400> SEQUENCE: 47

Met Ser Glu Val Lys Asn Arg Val Cys Leu Val Val Ile Asp Gly Trp
1               5                   10                  15

Gly Ile Ser Asn Glu Ser Lys Gly Asn Ala Ile Leu Asn Ala Lys Thr
            20                  25                  30

Pro Val Met Asp Glu Leu Cys Ala Leu Asn Ser His Pro Ile Glu Ala
            35                  40                  45

His Gly Leu His Val Gly Leu Pro Glu Gly Leu Met Gly Asn Ser Glu
        50                  55                  60

Val Gly His Leu Asn Ile Gly Ala Gly Arg Val Val Tyr Gln Asp Ile
65                  70                  75                  80

Val Arg Ile Asn Leu Ala Val Lys Asn Lys Thr Leu Val Glu Asn Lys
                85                  90                  95

His Leu Lys Glu Ala Ala Glu Arg Ala Ile Lys Gly Asn Gly Arg Ile
            100                 105                 110

His Leu Cys Gly Leu Val Ser Asp Gly Val His Ser His Ile Asp
            115                 120                 125

His Leu Phe Ala Leu Ile Thr Ala Leu Lys Gln Leu Lys Val Pro Gln
        130                 135                 140

Leu Tyr Ile His Phe Phe Gly Asp Gly Arg Asp Thr Ser Pro Thr Ser
145                 150                 155                 160

Gly Val Gly Phe Leu Gln Gln Leu Ile Asp Phe Val Asn Lys Glu Gln
                165                 170                 175

Tyr Gly Glu Ile Ala Thr Ile Val Gly Arg Tyr Ala Met Asp Arg
            180                 185                 190

Asp Lys Arg Trp Glu Arg Ile Arg Val Cys Tyr Asp Ala Leu Ile Ala
            195                 200                 205

Gly Val Gly Glu Lys Thr Thr Ile Asp Lys Ala Ile Asp Val Ile Lys
        210                 215                 220

Gly Arg Tyr Ala Lys Asp Glu Thr Asp Glu Phe Leu Lys Pro Ile Ile
225                 230                 235                 240

Leu Ser Asp Lys Gly Arg Thr Lys Asp Gly Asp Thr Leu Ile Phe Phe
```

```
                       245                 250                 255
Asp Tyr Arg Ala Asp Arg Met Arg Glu Ile Thr Glu Cys Met Gly Met
                260                 265                 270

Glu Arg Tyr Lys Asp Leu Lys Ser Asp Ile Lys His Pro Lys Asp Met
            275                 280                 285

Gln Val Ile Gly Met Thr Gln Tyr Lys Ala Glu Phe Thr Phe Pro Ala
        290                 295                 300

Leu Phe Pro Pro Glu Ser His Lys Asn Val Leu Ala Glu Trp Leu Ser
305                 310                 315                 320

Val Lys Gly Leu Thr Gln Phe His Cys Ala Glu Thr Glu Lys Tyr Ala
                325                 330                 335

His Val Thr Phe Phe Asn Gly Val Glu Lys Gln Phe Glu Asn
            340                 345                 350

Glu Glu Arg Cys Leu Val Pro Ser Pro Lys Val Ala Thr Tyr Asp Leu
        355                 360                 365

Glu Pro Ala Met Ser Ser Ala Gly Val Ala Asp Lys Met Ile Glu Gln
    370                 375                 380

Leu Asn Arg Lys Ala His Ala Phe Ile Met Cys Asn Phe Ala Pro Pro
385                 390                 395                 400

Asp Met Val Gly His Thr Gly Val Tyr Glu Ala Ala Val Lys Ala Val
                405                 410                 415

Glu Ala Thr Asp Ile Ala Ile Gly Arg Ile Tyr Glu Ala Cys Lys Lys
            420                 425                 430

Asn Asp Tyr Val Leu Met Val Thr Ala Asp His Gly Asn Ala Glu Lys
        435                 440                 445

Met Ile Ala Pro Asp Gly Gly Lys His Thr Ala His Thr Cys Asn Leu
    450                 455                 460

Val Pro Phe Thr Cys Ser Ser Leu Lys Phe Lys Phe Met Asp Lys Leu
465                 470                 475                 480

Pro Asp Arg Glu Met Ala Leu Cys Asp Val Ala Pro Thr Val Leu Lys
                485                 490                 495

Val Leu Gly Leu Pro Leu Pro Ser Glu Met Thr Gly Lys Pro Val Val
            500                 505                 510

Ile Glu Val
        515

<210> SEQ ID NO 48
<211> LENGTH: 515
<212> TYPE: PRT
<213> ORGANISM: Dirofilaria immitis

<400> SEQUENCE: 48

Met Ala Glu Ala Lys Asn Arg Val Cys Leu Val Val Ile Asp Gly Trp
1               5                   10                  15

Gly Ile Ser Asn Glu Ser Lys Gly Asn Ala Ile Leu Asn Ala Lys Thr
            20                  25                  30

Pro Ile Met Asp Glu Leu Cys Ala Leu Asn Ser His Pro Ile Glu Ala
        35                  40                  45

His Gly Leu His Val Gly Leu Pro Glu Gly Leu Met Gly Asn Ser Glu
    50                  55                  60

Val Gly His Leu Asn Ile Gly Ala Gly Arg Val Val Tyr Gln Asp Ile
65                  70                  75                  80

Val Arg Ile Asn Leu Ala Val Lys Asn Lys Thr Leu Val Glu Asn Lys
                85                  90                  95
```

```
His Leu Lys Glu Ala Ala Glu Arg Ala Ile Lys Gly Asn Gly Arg Ile
            100                 105                 110

His Leu Cys Gly Leu Val Ser Asp Gly Gly Val His Ser His Ile Asp
        115                 120                 125

His Leu Phe Ala Leu Val Thr Ala Leu Lys Gln Leu Lys Val Pro Gln
    130                 135                 140

Leu Phe Ile His Phe Phe Gly Asp Gly Arg Asp Thr Ser Pro Thr Ser
145                 150                 155                 160

Gly Val Gly Phe Leu Glu Gln Leu Ile Asp Phe Val Asn Lys Glu Gln
                165                 170                 175

Tyr Gly Val Ile Ala Thr Ile Val Gly Arg Tyr Tyr Ala Met Asp Arg
            180                 185                 190

Asp Lys Arg Trp Glu Arg Ile Arg Val Cys Tyr Asp Ala Leu Ile Ala
        195                 200                 205

Gly Val Gly Glu Lys Ala Thr Ile Asp Lys Ala Val Asp Val Ile Lys
    210                 215                 220

Ser Arg Tyr Ala Lys Asp Glu Thr Asp Glu Phe Leu Lys Pro Ile Ile
225                 230                 235                 240

Leu Ser Asp Glu Gly Arg Thr Lys Asp Gly Asp Thr Leu Ile Phe Phe
                245                 250                 255

Asp Tyr Arg Ala Asp Arg Met Arg Glu Ile Thr Glu Cys Met Gly Met
            260                 265                 270

Glu Arg Tyr Lys Asp Leu Lys Ser Asp Ile Lys His Pro Lys Asn Met
        275                 280                 285

Gln Val Ile Gly Met Thr Gln Tyr Lys Ala Glu Phe Thr Phe Pro Ala
    290                 295                 300

Leu Phe Pro Pro Glu Ser His Lys Asn Val Leu Ala Glu Trp Leu Ser
305                 310                 315                 320

Val Asn Gly Val Thr Gln Phe His Cys Ala Glu Thr Glu Lys Tyr Ala
                325                 330                 335

His Val Thr Phe Phe Phe Asn Gly Gly Val Glu Lys Gln Phe Glu Asn
            340                 345                 350

Glu Glu Arg Cys Leu Val Ala Ser Pro Lys Val Ala Thr Tyr Asp Leu
        355                 360                 365

Asp Pro Pro Met Ser Ser Ala Gly Val Ala Asp Lys Met Ile Glu Gln
    370                 375                 380

Leu Asp Arg Lys Ala His Ala Phe Val Met Cys Asn Phe Ala Pro Pro
385                 390                 395                 400

Asp Met Val Gly His Thr Gly Val Tyr Glu Ala Ala Val Lys Ala Val
                405                 410                 415

Glu Ala Thr Asp Ile Ala Ile Gly Arg Ile Tyr Glu Ala Cys Lys Lys
            420                 425                 430

Asn Asp Tyr Ile Leu Met Val Thr Ala Asp His Gly Asn Ala Glu Lys
        435                 440                 445

Met Met Ala Pro Asp Gly Ser Lys His Thr Ala His Thr Cys Asn Leu
    450                 455                 460

Val Pro Phe Thr Cys Ser Ser Met Lys Phe Lys Phe Met Asp Lys Leu
465                 470                 475                 480

Pro Asp Arg Glu Met Ala Leu Cys Asp Val Ala Pro Thr Val Leu Lys
                485                 490                 495

Val Met Gly Leu Pro Leu Pro Pro Glu Met Thr Gly Lys Pro Val Val
            500                 505                 510

Ile Glu Val
```

<210> SEQ ID NO 49
<211> LENGTH: 514
<212> TYPE: PRT
<213> ORGANISM: Escherichia coli

<400> SEQUENCE: 49

Met Leu Val Ser Lys Lys Pro Met Val Leu Val Ile Leu Asp Gly Tyr
1               5                   10                  15

Gly Tyr Arg Glu Glu Gln Asp Asn Ala Ile Phe Ser Ala Lys Thr
            20                  25                  30

Pro Val Met Asp Ala Leu Trp Ala Asn Arg Pro His Thr Leu Ile Asp
        35                  40                  45

Ala Ser Gly Leu Glu Val Gly Leu Pro Asp Arg Gln Met Gly Asn Ser
    50                  55                  60

Glu Val Gly His Val Asn Leu Gly Ala Gly Arg Ile Val Tyr Gln Asp
65                  70                  75                  80

Leu Thr Arg Leu Asp Val Glu Ile Lys Asp Arg Ala Phe Phe Ala Asn
                85                  90                  95

Pro Val Leu Thr Gly Ala Val Asp Lys Ala Lys Asn Ala Gly Lys Ala
            100                 105                 110

Val His Ile Met Gly Leu Leu Ser Ala Gly Gly Val His Ser His Glu
        115                 120                 125

Asp His Ile Met Ala Met Val Glu Leu Ala Ala Glu Arg Gly Ala Glu
    130                 135                 140

Lys Ile Tyr Leu His Ala Phe Leu Asp Gly Arg Asp Thr Pro Pro Arg
145                 150                 155                 160

Ser Ala Glu Ser Ser Leu Lys Lys Phe Glu Glu Lys Phe Ala Ala Leu
                165                 170                 175

Gly Lys Gly Arg Val Ala Ser Ile Ile Gly Arg Tyr Tyr Ala Met Asp
            180                 185                 190

Arg Asp Asn Arg Trp Asp Arg Val Glu Lys Ala Tyr Asp Leu Leu Thr
        195                 200                 205

Leu Ala Gln Gly Glu Phe Gln Ala Asp Thr Ala Val Ala Gly Leu Gln
    210                 215                 220

Ala Ala Tyr Ala Arg Asp Glu Asn Asp Glu Phe Val Lys Ala Thr Val
225                 230                 235                 240

Ile Arg Ala Glu Gly Gln Pro Asp Ala Ala Met Glu Asp Gly Asp Ala
                245                 250                 255

Leu Ile Phe Met Asn Phe Arg Ala Asp Arg Ala Arg Glu Ile Thr Arg
            260                 265                 270

Ala Phe Val Asn Ala Asp Phe Asp Gly Phe Ala Arg Lys Lys Val Val
        275                 280                 285

Asn Val Asp Phe Val Met Leu Thr Glu Tyr Ala Ala Asp Ile Lys Thr
    290                 295                 300

Ala Val Ala Tyr Pro Pro Ala Ser Leu Val Asn Thr Phe Gly Glu Trp
305                 310                 315                 320

Met Ala Lys Asn Asp Lys Thr Gln Leu Arg Ile Ser Glu Thr Glu Lys
                325                 330                 335

Tyr Ala His Val Thr Phe Phe Phe Asn Gly Gly Val Glu Glu Ser Phe
            340                 345                 350

Lys Gly Glu Asp Arg Ile Leu Ile Asn Ser Pro Lys Val Ala Thr Tyr
        355                 360                 365

```
Asp Leu Gln Pro Glu Met Ser Ser Ala Glu Leu Thr Glu Lys Leu Val
    370                 375                 380

Ala Ala Ile Lys Ser Gly Lys Tyr Asp Thr Ile Ile Cys Asn Tyr Pro
385                 390                 395                 400

Asn Gly Asp Met Val Gly His Thr Gly Val Met Glu Ala Ala Val Lys
                405                 410                 415

Ala Val Glu Ala Leu Asp His Cys Val Glu Val Ala Lys Ala Val
            420                 425                 430

Glu Ser Val Gly Gly Gln Leu Leu Ile Thr Ala Asp His Gly Asn Ala
        435                 440                 445

Glu Gln Met Arg Asp Pro Ala Thr Gly Gln Ala His Thr Ala His Thr
450                 455                 460

Asn Leu Pro Val Pro Leu Ile Tyr Val Gly Asp Lys Asn Val Lys Ala
465                 470                 475                 480

Val Glu Gly Gly Lys Leu Ser Asp Ile Ala Pro Thr Met Leu Ser Leu
                485                 490                 495

Met Gly Met Glu Ile Pro Gln Glu Met Thr Gly Lys Pro Leu Phe Ile
                500                 505                 510

Val Glu

<210> SEQ ID NO 50
<211> LENGTH: 505
<212> TYPE: PRT
<213> ORGANISM: Staphylococcus aureus

<400> SEQUENCE: 50

Met Ala Lys Lys Pro Thr Ala Leu Ile Ile Leu Asp Gly Phe Ala Asn
1               5                   10                  15

Arg Glu Ser Glu His Gly Asn Ala Val Lys Leu Ala Asn Lys Pro Asn
                20                  25                  30

Phe Asp Arg Tyr Tyr Asn Lys Tyr Pro Thr Thr Gln Ile Glu Ala Ser
            35                  40                  45

Gly Leu Asp Val Gly Leu Pro Glu Gly Gln Met Gly Asn Ser Glu Val
        50                  55                  60

Gly His Met Asn Ile Gly Ala Gly Arg Ile Val Tyr Gln Ser Leu Thr
65                  70                  75                  80

Arg Ile Asn Lys Ser Ile Glu Asp Gly Asp Phe Phe Glu Asn Asp Val
                85                  90                  95

Leu Asn Asn Ala Ile Ala His Val Asn Ser His Asp Ser Ala Leu His
                100                 105                 110

Ile Phe Gly Leu Leu Ser Asp Gly Gly Val His Ser His Tyr Lys His
            115                 120                 125

Leu Phe Ala Leu Leu Glu Leu Ala Lys Lys Gln Gly Val Glu Lys Val
        130                 135                 140

Tyr Val His Ala Phe Leu Asp Gly Arg Asp Val Asp Gln Lys Ser Ala
145                 150                 155                 160

Leu Lys Tyr Ile Glu Glu Thr Glu Ala Lys Phe Asn Glu Leu Gly Ile
                165                 170                 175

Gly Gln Phe Ala Ser Val Ser Gly Arg Tyr Tyr Ala Met Asp Arg Asp
            180                 185                 190

Lys Arg Trp Glu Arg Glu Glu Lys Ala Tyr Asn Ala Ile Arg Asn Phe
        195                 200                 205

Asp Ala Pro Thr Tyr Ala Thr Ala Lys Glu Gly Val Glu Ala Ser Tyr
    210                 215                 220
```

```
Asn Glu Gly Leu Thr Asp Glu Phe Val Val Pro Phe Ile Val Glu Asn
225                 230                 235                 240

Gln Asn Asp Gly Val Asn Asp Gly Asp Ala Val Ile Phe Tyr Asn Phe
            245                 250                 255

Arg Pro Asp Arg Ala Ala Gln Leu Ser Glu Ile Phe Ala Asn Arg Ala
        260                 265                 270

Phe Glu Gly Phe Lys Val Glu Gln Val Lys Asp Leu Phe Tyr Ala Thr
    275                 280                 285

Phe Thr Lys Tyr Asn Asp Asn Ile Asp Ala Ala Ile Val Phe Glu Lys
290                 295                 300

Val Asp Leu Asn Asn Thr Ile Gly Glu Ile Ala Gln Asn Asn Asn Leu
305                 310                 315                 320

Thr Gln Leu Arg Ile Ala Glu Thr Glu Lys Tyr Pro His Val Thr Tyr
            325                 330                 335

Phe Met Ser Gly Gly Arg Asn Glu Glu Phe Lys Gly Glu Arg Arg Arg
        340                 345                 350

Leu Ile Asp Ser Pro Lys Val Ala Thr Tyr Asp Leu Lys Pro Glu Met
    355                 360                 365

Ser Ala Tyr Glu Val Lys Asp Ala Leu Leu Glu Glu Leu Asn Lys Gly
370                 375                 380

Asp Leu Asp Leu Ile Ile Leu Asn Phe Ala Asn Pro Asp Met Val Gly
385                 390                 395                 400

His Ser Gly Met Leu Glu Pro Thr Ile Lys Ala Ile Glu Ala Val Asp
            405                 410                 415

Glu Cys Leu Gly Glu Val Val Asp Lys Ile Leu Asp Met Asp Gly Tyr
        420                 425                 430

Ala Ile Ile Thr Ala Asp His Gly Asn Ser Asp Gln Val Leu Thr Asp
    435                 440                 445

Asp Asp Gln Pro Met Thr Thr His Thr Thr Asn Pro Val Pro Val Ile
450                 455                 460

Val Thr Lys Glu Gly Val Thr Leu Arg Glu Thr Gly Arg Leu Gly Asp
465                 470                 475                 480

Leu Ala Pro Thr Leu Leu Asp Leu Leu Asn Val Glu Gln Pro Glu Asp
            485                 490                 495

Met Thr Gly Glu Ser Leu Ile Lys His
            500                 505

<210> SEQ ID NO 51
<211> LENGTH: 509
<212> TYPE: PRT
<213> ORGANISM: Bacillus anthracis

<400> SEQUENCE: 51

Met Arg Lys Pro Thr Ala Leu Ile Ile Leu Asp Gly Phe Gly Leu Arg
1               5                   10                  15

Glu Glu Thr Tyr Gly Asn Ala Val Ala Gln Ala Lys Lys Pro Asn Phe
            20                  25                  30

Asp Gly Tyr Trp Asn Lys Phe Pro His Thr Thr Leu Thr Ala Cys Gly
        35                  40                  45

Glu Ala Val Gly Leu Pro Glu Gly Gln Met Gly Asn Ser Glu Val Gly
    50                  55                  60

His Leu Asn Ile Gly Ala Gly Arg Ile Val Tyr Gln Ser Leu Thr Arg
65                  70                  75                  80

Val Asn Val Ala Ile Arg Glu Gly Glu Phe Asp Lys Asn Glu Thr Phe
            85                  90                  95
```

```
Gln Ser Ala Ile Lys Ser Val Lys Glu Lys Gly Thr Ala Leu His Leu
            100                 105                 110

Phe Gly Leu Leu Ser Asp Gly Val His Ser His Met Asn His Met
        115                 120                 125

Phe Ala Leu Leu Arg Leu Ala Ala Lys Glu Gly Val Glu Lys Val Tyr
        130                 135                 140

Ile His Ala Phe Leu Asp Gly Arg Asp Val Gly Pro Lys Thr Ala Gln
145                 150                 155                 160

Ser Tyr Ile Asp Ala Thr Asn Glu Val Ile Lys Glu Thr Gly Val Gly
                165                 170                 175

Gln Phe Ala Thr Ile Ser Gly Arg Tyr Tyr Ser Met Asp Arg Asp Lys
                180                 185                 190

Arg Trp Asp Arg Val Glu Lys Cys Tyr Arg Ala Met Val Asn Gly Glu
        195                 200                 205

Gly Pro Thr Tyr Lys Ser Ala Glu Glu Cys Val Glu Asp Ser Tyr Ala
        210                 215                 220

Asn Gly Ile Tyr Asp Glu Phe Val Leu Pro Ser Val Ile Val Asn Glu
225                 230                 235                 240

Asp Asn Thr Pro Val Ala Thr Ile Asn Asp Asp Ala Val Ile Phe
                245                 250                 255

Tyr Asn Phe Arg Pro Asp Arg Ala Ile Gln Ile Ala Arg Val Phe Thr
                260                 265                 270

Asn Gly Asp Phe Arg Glu Phe Asp Arg Gly Glu Lys Val Pro His Ile
            275                 280                 285

Pro Glu Phe Val Cys Met Thr His Phe Ser Glu Thr Val Asp Gly Tyr
        290                 295                 300

Val Ala Phe Lys Pro Met Asn Leu Asp Asn Thr Leu Gly Glu Val Val
305                 310                 315                 320

Ala Gln Ala Gly Leu Lys Gln Leu Arg Ile Ala Glu Thr Glu Lys Tyr
                325                 330                 335

Pro His Val Thr Phe Phe Ser Gly Gly Arg Glu Ala Glu Phe Pro
            340                 345                 350

Gly Glu Glu Arg Ile Leu Ile Asn Ser Pro Lys Val Ala Thr Tyr Asp
            355                 360                 365

Leu Lys Pro Glu Met Ser Ile Tyr Glu Val Thr Asp Ala Leu Val Asn
        370                 375                 380

Glu Ile Glu Asn Asp Lys His Asp Val Ile Leu Asn Phe Ala Asn
385                 390                 395                 400

Cys Asp Met Val Gly His Ser Gly Met Met Glu Pro Thr Ile Lys Ala
                405                 410                 415

Val Glu Ala Thr Asp Glu Cys Leu Gly Lys Val Val Gly Ala Ile Leu
                420                 425                 430

Ala Lys Asp Gly Val Ala Leu Ile Thr Ala Asp His Gly Asn Ala Asp
        435                 440                 445

Glu Glu Leu Thr Ser Glu Gly Glu Pro Met Thr Ala His Thr Thr Asn
        450                 455                 460

Pro Val Pro Phe Ile Val Thr Lys Asn Asp Val Glu Leu Arg Glu Asp
465                 470                 475                 480

Gly Ile Leu Gly Asp Ile Ala Pro Thr Met Leu Thr Leu Leu Gly Val
                485                 490                 495

Glu Gln Pro Lys Glu Met Thr Gly Lys Thr Ile Ile Lys
            500                 505
```

<210> SEQ ID NO 52
<211> LENGTH: 553
<212> TYPE: PRT
<213> ORGANISM: Leishmania mexicana

<400> SEQUENCE: 52

Met Ser Ala Leu Leu Lys Pro His Lys Asp Leu Pro Arg Arg Thr
1               5                   10                  15

Val Leu Ile Val Val Met Asp Gly Leu Gly Ile Gly Pro Glu Asp Asp
            20                  25                  30

Tyr Asp Ala Val His Met Ala Ser Thr Pro Phe Met Asp Ala His Arg
                35                  40                  45

Arg Asp Asn Arg His Phe Arg Cys Val Arg Ala His Gly Thr Ala Val
    50                  55                  60

Gly Leu Pro Thr Asp Ala Asp Met Gly Asn Ser Glu Val Gly His Asn
65                  70                  75                  80

Ala Leu Gly Ala Gly Arg Val Ala Leu Gln Gly Ala Ser Leu Val Asp
                85                  90                  95

Asp Ala Ile Lys Ser Gly Glu Ile Tyr Thr Gly Glu Gly Tyr Arg Tyr
            100                 105                 110

Leu His Gly Ala Phe Ser Lys Glu Gly Ser Thr Leu His Leu Ile Gly
        115                 120                 125

Leu Leu Ser Asp Gly Gly Val His Ser Arg Asp Asn Gln Ile Tyr Ser
    130                 135                 140

Ile Ile Glu His Ala Val Lys Asp Gly Ala Lys Arg Ile Arg Val His
145                 150                 155                 160

Ala Leu Tyr Asp Gly Arg Asp Val Pro Asp Gly Ser Ser Phe Arg Phe
                165                 170                 175

Thr Asp Glu Leu Glu Ala Val Leu Ala Lys Val Arg Gln Asn Gly Cys
            180                 185                 190

Asp Ala Ala Ile Ala Ser Gly Gly Arg Met Phe Val Thr Met Asp
        195                 200                 205

Arg Tyr Asp Ala Asp Trp Ser Ile Val Glu Arg Gly Trp Arg Ala Gln
    210                 215                 220

Val Leu Gly Asp Ala Arg His Phe His Ser Ala Lys Glu Ala Ile Thr
225                 230                 235                 240

Thr Phe Arg Glu Glu Asp Pro Lys Val Thr Asp Gln Tyr Tyr Pro Pro
                245                 250                 255

Phe Ile Val Val Asp Glu Gln Asp Lys Pro Leu Gly Thr Ile Glu Asp
            260                 265                 270

Gly Asp Ala Val Leu Cys Val Asn Phe Arg Gly Asp Arg Val Ile Glu
        275                 280                 285

Met Thr Arg Ala Phe Glu Asp Glu Asp Phe Asn Lys Phe Asp Arg Val
    290                 295                 300

Arg Val Pro Lys Val Arg Tyr Ala Gly Met Met Arg Tyr Asp Gly Asp
305                 310                 315                 320

Leu Gly Ile Pro Asn Asn Phe Leu Val Pro Pro Lys Leu Thr Arg
                325                 330                 335

Val Ser Glu Glu Tyr Leu Cys Ser Gly Leu Asn Ile Phe Ala Cys
            340                 345                 350

Ser Glu Thr Gln Lys Phe Gly His Val Thr Tyr Phe Trp Asn Gly Asn
        355                 360                 365

Arg Ser Gly Lys Ile Asp Glu Lys His Glu Thr Phe Lys Glu Val Pro
    370                 375                 380

```
Ser Asp Arg Val Gln Phe Asn Glu Lys Pro Arg Met Gln Ser Ala Ala
385                 390                 395                 400

Ile Thr Glu Ala Ala Ile Glu Ala Leu Lys Ser Gly Met Tyr Asn Val
            405                 410                 415

Val Arg Ile Asn Phe Pro Asn Gly Asp Met Val Gly His Thr Gly Asp
        420                 425                 430

Leu Lys Ala Thr Ile Thr Gly Val Glu Ala Val Asp Glu Ser Leu Ala
        435                 440                 445

Lys Leu Lys Asp Ala Val Asp Ser Val Asn Gly Val Tyr Ile Val Thr
450                 455                 460

Ala Asp His Gly Asn Ser Asp Met Ala Gln Arg Asp Lys Lys Gly
465                 470                 475                 480

Lys Pro Met Lys Asp Gly Asn Gly Asn Val Leu Pro Leu Thr Ser His
                485                 490                 495

Thr Leu Ser Pro Val Pro Val Phe Ile Gly Gly Ala Gly Leu Asp Pro
            500                 505                 510

Arg Val Ala Met Arg Thr Asp Leu Pro Ala Ala Gly Leu Ala Asn Val
            515                 520                 525

Thr Ala Thr Phe Ile Asn Leu Leu Gly Phe Glu Ala Pro Glu Asp Tyr
        530                 535                 540

Glu Pro Ser Leu Ile Tyr Val Glu Lys
545                 550
```

<210> SEQ ID NO 53
<211> LENGTH: 551
<212> TYPE: PRT
<213> ORGANISM: Trypanosoma brucei

<400> SEQUENCE: 53

```
Met Ala Leu Thr Leu Ala Ala His Lys Thr Leu Pro Arg Arg Lys Leu
1               5                   10                  15

Val Leu Val Val Leu Asp Gly Val Gly Ile Gly Pro Arg Asp Glu Tyr
                20                  25                  30

Asp Ala Val His Val Ala Lys Thr Pro Leu Met Asp Ala Leu Phe Asn
            35                  40                  45

Asp Pro Lys His Phe Arg Ser Ile Cys Ala His Gly Thr Ala Val Gly
        50                  55                  60

Leu Pro Thr Asp Ala Asp Met Gly Asn Ser Glu Val Gly His Asn Ala
65                  70                  75                  80

Leu Gly Ala Gly Arg Val Val Leu Gln Gly Ala Ser Leu Val Asp Asp
                85                  90                  95

Ala Leu Glu Ser Gly Glu Ile Phe Thr Ser Glu Gly Tyr Arg Tyr Leu
            100                 105                 110

His Gly Ala Phe Ser Gln Pro Gly Arg Thr Leu His Leu Ile Gly Leu
        115                 120                 125

Leu Ser Asp Gly Gly Val His Ser Arg Asp Asn Gln Val Tyr Gln Ile
    130                 135                 140

Leu Lys His Ala Gly Ala Asn Gly Ala Lys Arg Ile Arg Val His Ala
145                 150                 155                 160

Leu Tyr Asp Gly Arg Asp Val Pro Asp Lys Thr Ser Phe Lys Phe Thr
                165                 170                 175

Asp Glu Leu Glu Glu Val Leu Ala Lys Leu Arg Glu Gly Gly Cys Asp
            180                 185                 190

Ala Arg Ile Ala Ser Gly Gly Gly Arg Met Phe Val Thr Met Asp Arg
```

```
            195                 200                 205
Tyr Glu Ala Asp Trp Ser Ile Val Glu Arg Gly Trp Arg Ala Gln Val
210                 215                 220

Leu Gly Glu Gly Arg Ala Phe Lys Ser Ala Arg Glu Ala Leu Thr Lys
225                 230                 235                 240

Phe Arg Glu Glu Asp Ala Asn Ile Ser Asp Gln Tyr Tyr Pro Pro Phe
                245                 250                 255

Val Ile Ala Gly Asp Asp Gly Arg Pro Ile Gly Thr Ile Glu Asp Gly
                260                 265                 270

Asp Ala Val Leu Cys Phe Asn Phe Arg Gly Asp Arg Val Ile Glu Met
                275                 280                 285

Ser Arg Ala Phe Glu Glu Glu Phe Asp Lys Phe Asn Arg Val Arg
290                 295                 300

Leu Pro Lys Val Arg Tyr Ala Gly Met Met Arg Tyr Asp Gly Asp Leu
305                 310                 315                 320

Gly Ile Pro Asn Asn Phe Leu Val Pro Pro Lys Leu Thr Arg Thr
                325                 330                 335

Ser Glu Glu Tyr Leu Ile Gly Ser Gly Cys Asn Ile Phe Ala Leu Ser
                340                 345                 350

Glu Thr Gln Lys Phe Gly His Val Thr Tyr Phe Trp Asn Gly Asn Arg
                355                 360                 365

Ser Gly Lys Leu Ser Glu Arg Glu Thr Phe Cys Glu Ile Pro Ser
370                 375                 380

Asp Arg Val Gln Phe Asn Gln Lys Pro Leu Met Lys Ser Lys Glu Ile
385                 390                 395                 400

Thr Asp Ala Ala Val Asp Ala Ile Lys Ser Gly Lys Tyr Asp Met Ile
                405                 410                 415

Arg Ile Asn Tyr Pro Asn Gly Asp Met Val Gly His Thr Gly Asp Leu
                420                 425                 430

Lys Ala Thr Ile Thr Ser Leu Glu Ala Val Asp Gln Ser Leu Gln Arg
                435                 440                 445

Leu Lys Glu Ala Val Asp Ser Val Asn Gly Val Phe Leu Ile Thr Ala
450                 455                 460

Asp His Gly Asn Ser Asp Asp Met Val Gln Arg Asp Lys Lys Gly Lys
465                 470                 475                 480

Pro Val Arg Asp Ala Glu Gly Asn Leu Met Pro Leu Thr Ser His Thr
                485                 490                 495

Leu Ala Pro Val Pro Val Phe Ile Gly Gly Ala Gly Leu Asp Pro Arg
                500                 505                 510

Val Gln Met Arg Thr Asp Leu Pro Arg Ala Gly Leu Ala Asn Val Thr
                515                 520                 525

Ala Thr Phe Ile Asn Leu Met Gly Phe Glu Ala Pro Ser Asp Tyr Glu
                530                 535                 540

Pro Ser Leu Ile Glu Val Ala
545                 550

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
```

```
<400> SEQUENCE: 54

Tyr Asp Tyr Pro Gly Asp His Cys Tyr Leu Tyr
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (9)..(9)
<223> OTHER INFORMATION: METHYLATION

<400> SEQUENCE: 55

Tyr Asp Tyr Pro Gly Asp Tyr Cys Tyr Leu Tyr Gly Thr Cys Gly
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (10)..(10)
<223> OTHER INFORMATION: METHYLATION

<400> SEQUENCE: 56

Tyr Asp Tyr Pro Gly Asp Tyr Cys Tyr Leu Tyr Gly Thr Cys Gly
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (11)..(11)
<223> OTHER INFORMATION: METHYLATION

<400> SEQUENCE: 57

Tyr Asp Tyr Pro Gly Asp Tyr Cys Tyr Leu Tyr Gly Thr Cys Gly
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
```

```
<223> OTHER INFORMATION: cyclic linkage
<220> FEATURE:
<221> NAME/KEY: MOD_RES
<222> LOCATION: (12)..(12)
<223> OTHER INFORMATION: METHYLATION

<400> SEQUENCE: 58

Tyr Asp Tyr Pro Gly Asp Tyr Cys Tyr Leu Tyr Gly Thr Cys Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (13)..(13)
<223> OTHER INFORMATION: METHYLATION

<400> SEQUENCE: 59

Tyr Asp Tyr Pro Gly Asp Tyr Cys Tyr Leu Tyr Gly Thr Cys Gly
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (14)..(14)
<223> OTHER INFORMATION: METHYLATION

<400> SEQUENCE: 60

Tyr Asp Tyr Pro Gly Asp Tyr Cys Tyr Leu Tyr Gly Thr Cys Gly
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (15)..(15)
<223> OTHER INFORMATION: METHYLATION

<400> SEQUENCE: 61

Tyr Asp Tyr Pro Gly Asp Tyr Cys Tyr Leu Tyr Gly Thr Cys Gly
1               5                   10                  15

<210> SEQ ID NO 62
<211> LENGTH: 15
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cylcic linkage
<220> FEATURE:
<221> NAME/KEY: MOD_RES
<222> LOCATION: (13)..(15)
<223> OTHER INFORMATION: METHYLATION

<400> SEQUENCE: 62

Tyr Asp Tyr Pro Gly Asp Tyr Cys Tyr Leu Tyr Gly Thr Cys Gly
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (14)..(15)
<223> OTHER INFORMATION: METHYLATION

<400> SEQUENCE: 63

Tyr Asp Tyr Pro Gly Asp Tyr Cys Tyr Leu Tyr Gly Thr Cys Gly
1               5                   10                  15

<210> SEQ ID NO 64
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (15)..(15)
<223> OTHER INFORMATION: METHYLATION

<400> SEQUENCE: 64

Tyr Asp Tyr Pro Gly Asp Tyr Cys Tyr Leu Tyr Gly Met Glu Thr Cys
1               5                   10                  15

Met Glu Gly

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (13)..(14)
<223> OTHER INFORMATION: METHYLATION
```

<400> SEQUENCE: 65

Tyr Asp Tyr Pro Gly Asp Tyr Cys Tyr Leu Tyr Gly Thr Cys Gly
1               5                   10                  15

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (11)..(11)
<223> OTHER INFORMATION: METHYLATION

<400> SEQUENCE: 66

Tyr Asp Tyr Pro Gly Asp Tyr Cys Tyr Leu Tyr
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (13)..(13)
<223> OTHER INFORMATION: METHYLATION

<400> SEQUENCE: 67

Tyr Asp Tyr Pro Gly Asp Tyr Cys Tyr Leu Tyr Gly Thr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: cyclic linkage
<220> FEATURE:
<221> NAME/KEY: MOD_RES
<222> LOCATION: (11)..(11)
<223> OTHER INFORMATION: METHYLATION

<400> SEQUENCE: 68

Tyr Asp Tyr Pro Gly Asp Tyr Cys Tyr Leu Tyr Gly Thr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)

```
<223> OTHER INFORMATION: cyclic linkage
<220> FEATURE:
<221> NAME/KEY: MOD_RES
<222> LOCATION: (11)..(11)
<223> OTHER INFORMATION: METHYLATION
<220> FEATURE:
<221> NAME/KEY: MOD_RES
<222> LOCATION: (13)..(13)
<223> OTHER INFORMATION: METHYLATION

<400> SEQUENCE: 69

Tyr Asp Tyr Pro Gly Asp Tyr Cys Tyr Leu Tyr Gly Thr
1               5                   10
```

US 10,808,010 B2

PEPTIDE INHIBITORS OF PHOSPHOGLYCERATE MUTASE AND METHODS OF USE

CROSS REFERENCE TO RELATED APPLICATIONS

This application is the § 371 U.S. National Stage of International Application No. PCT/US2017/046228, filed Aug. 10, 2017, which was published in English under PCT Article 21(2), which in turn claims the benefit of U.S. Provisional Application No. 62/373,835, filed Aug. 11, 2016, which is herein incorporated by reference in its entirety.

FIELD

This disclosure relates to peptide inhibitors of phosphoglycerate mutase, particularly peptide inhibitors, and methods of their use for treating or inhibiting microbial infection or disease.

BACKGROUND

Nematode worms are the most abundant animal on earth and are found in widely different environments. They can be free-living or parasitic, infecting plants, animals, and humans. Parasitic nematode infection in humans can lead to a number of devastating diseases. Lymphatic filariasis and onchocerciasis are neglected tropical diseases caused by filarial nematode parasites that are transmitted to humans by insects. Collectively, they afflict 150 million people in over 80 countries and threaten the health of over 1.5 billion people. These infections are responsible for extreme infirmity, social stigma and severe economic consequences. The lymphatic dwelling parasites such as *Wuchereria bancrofti* and *Brugia malayi* are the cause of lymphedema, hydrocele, and in the most extreme cases, elephantiasis. Infection with *Onchocerca volvulus* can result in severe dermatitis and/or blindness. The mainstay of filarial disease control for several years has been a limited number of drugs, predominantly ivermectin together with albendazole (where onchocerciasis is endemic) or diethylcarbamazine citrate (where onchocerciasis is not present). These compounds mainly target the larval stages and require annual or semi-annual administration. Furthermore, there are reports of drug resistance emerging (Churcher et al., *Proc. Natl. Acad. Sci. USA* 106:16716-16721, 2009; Osei-Atweneboana et al., *PLoS Negl. Trop. Dis.* 5:e998, 2011). Therefore, new drugs with a novel mode of action are needed.

SUMMARY

Disclosed herein are compounds and compositions for inhibiting phosphoglycerate mutase (PGM) activity. In some examples, the compounds selectively inhibit cofactor-independent PGM (iPGM). In particular embodiments, the compounds include one or more cyclic peptides.

In some embodiments, the compounds or compositions include an isolated peptide (such as a linear or cyclic peptide) that selectively or specifically inhibits activity of an iPGM compared to a cofactor-dependent PGM (dPGM). In some examples, the isolated peptide is 6-20 amino acids long and includes the amino acid sequence of any one of SEQ ID NOs: 1-22 and 54-69, an analog or derivative thereof, or a pharmaceutically acceptable salt or ester thereof. In some examples, the peptide is a cyclic peptide with an N-terminal ring structure of 6-15 amino acids (for example, 6-10 amino acids) and a C-terminal linear portion of 1-9 amino acids (for example, 3-8 amino acids). In particular examples, the isolated peptide includes a peptide having the structure of any one of the peptides in Tables 2, 6, 8, or 9 or FIG. 12A, 12B, or 21, or an analog or derivative thereof, or a pharmaceutically acceptable salt or ester thereof.

Also disclosed herein are methods of treating or inhibiting an infection in a subject, including administering to the subject an effective amount of a composition including one of more of the disclosed peptides or analogs or derivatives thereof, or pharmaceutically acceptable salts or esters thereof. In some examples, the methods including treating infection with a nematode (for example, treating a filarial disease), infection with *Leishmania*, or infection with a bacterium (for example, treating infection with *Staphylococcus aureus*, *Bacillus anthracis*, or *Streptococcus pneumoniae*).

The foregoing and other features of the disclosure will become more apparent from the following detailed description, which proceeds with reference to the accompanying figures.

BRIEF DESCRIPTION OF THE DRAWINGS

FIGS. 1A-1C are a series of panels showing PGM coupled-enzyme assays. FIG. 1A is a graph showing a reaction time course (1 hour) as measured by a continuous NADH-dependent absorbance assay. The absorbance measured at 340 nm decreases as NADH is oxidized to NAD and is dependent on the pyruvic acid formed in the prior enzymatic reactions. FIG. 1B is a graph showing that the linear phase of assays occurs over the initial 15 minutes. FIG. 1C is a graph showing calibration of bioluminescent end-point HTS assays for seven PGM orthologs and pyruvate kinase (PK)-FLuc control. The light generated in the bioluminescence assay is based on the oxidation of luciferin by ATP and oxygen, and is dependent on the ATP generated in the prior enzymatic reactions. Enzyme concentrations (Bm iPGM, 5 nM; Ce iPGM, 5 nM; Di iPGM, 10 nM; Ec iPGM, 10 nM; Ov iPGM, 20 nM; Hs dPGM, 5 nM; Ec dPGM, 4 nM) were adjusted to give approximately equivalent RLU after a 5 min assay time. Open bars are 'no PGM' controls for background measurements. Error bars are SD from 24 replicates.

FIG. 2A is a schematic diagram showing isomerization catalyzed by PGMs illustrating the phosphohistidine enzyme/2,3-phosphoglycerate intermediate of human cofactor-dependent PGM (dPGM, top) and the phosphoserine enzyme intermediate of *C. elegans* cofactor independent PGM (iPGM, bottom). FIG. 2B is a schematic diagram showing coupling enzymes used in kinetic NADH absorbance (from generated pyruvate) and endpoint bioluminescence (from generated ATP) assays. Coupling enzymes and substrates for the absorbance assay are enolase, 2-PG, pyruvate kinase, phosphoenolpyruvic acid (PEP), ADP, lactate dehydrogenase, pyruvic acid, and NADH. Coupling enzymes and substrates for the bioluminescence assay are enolase, 2-PG, pyruvate kinase, phosphoenolpyruvic acid (PEP), ADP, luciferase, ATP, and luciferin (LH2). The products of the absorbance assay are lactate and $NAD^+$. The products of the bioluminescence assay are oxyluciferin (L), $CO_2$ and light (hv). FIG. 2C is a schematic of gradient elution moving boundary capillary electrophoresis (GEMBE) device used in the direct detection of 2-PG/3-PG (left) and 1$^{st}$ derivative of current detected for phosphoglycerate isomers (right).

FIGS. 3A and 3B are a series of panels showing separation of phosphoglycerates with GEMBE. FIG. 3A shows current (top) and 1$^{st}$ derivative (bottom) plots for the elution of 2- and 3-PG FIG. 3B shows time courses for the conversion of 3-PG to 2-PG measured with GEMBE, for the *C. elegans* iPGM (top) and the *B. malayi* iPGM (bottom). Left axis, % conversion of (●) 2-PG, (○) 3-PG; right axis, ratio (+) 2-PG to 3-PG.

Figures 4A, 4B, 4C:
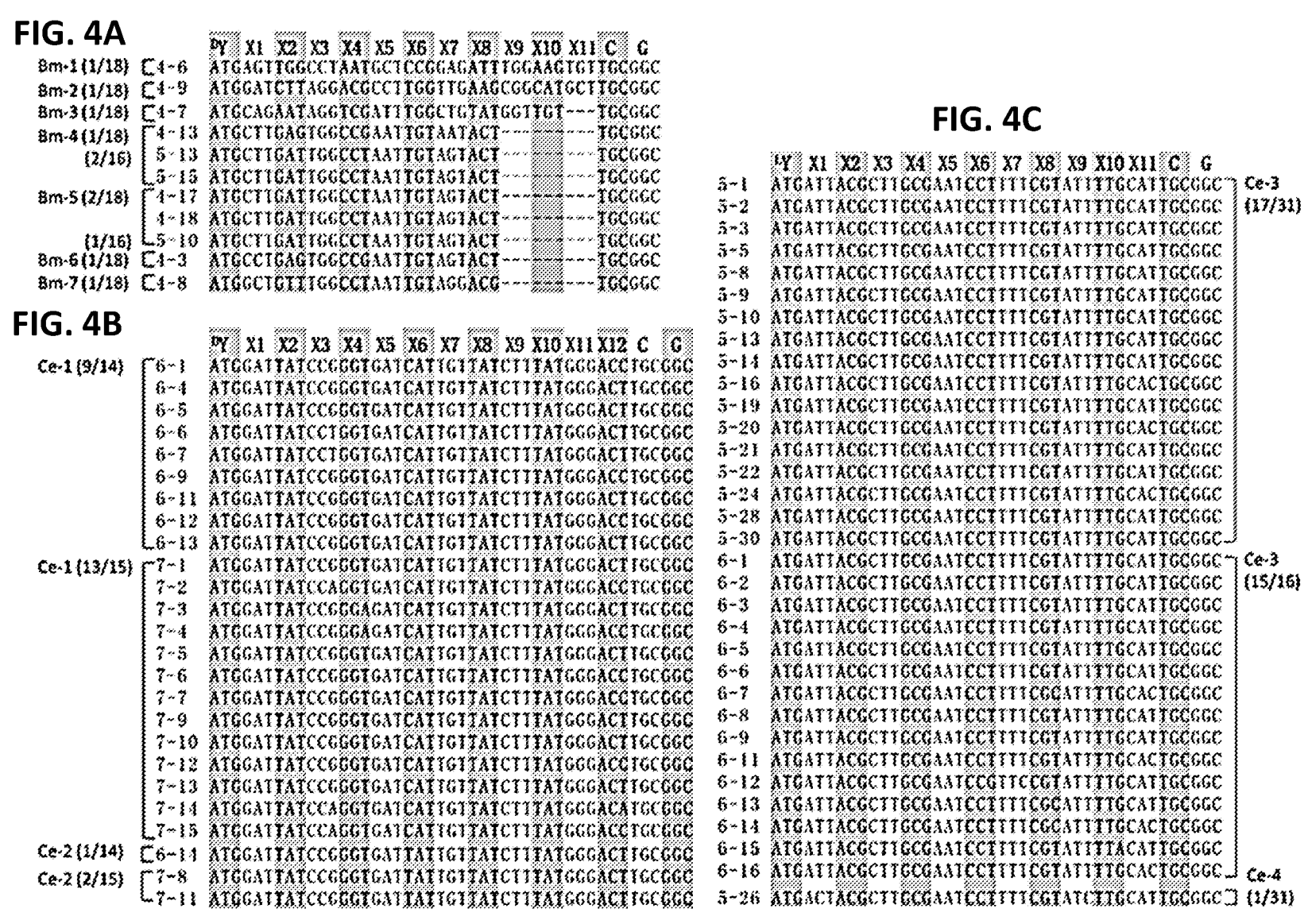

FIGS. 4A-4C are a series of panels showing sequence alignments of DNA sequences from RaPID selections. FIG. 4A is an alignment of DNA sequences identified from 4th and 5th rounds of selection with $^D$Y library against *B. malayi* iPGM. Sequence 4-6, SEQ ID NO: 23; 4-9, SEQ ID NO: 24; 4-7, SEQ ID NO: 25; 4-13, SEQ ID NO: 26; 5-13, 5-15, 4-17, 4-18, and 5-10, SEQ ID NO: 27; 4-3, SEQ ID NO: 28; 4-8, SEQ ID NO: 29. FIG. 4B is an alignment of DNA sequences identified from 6th and 7th rounds of selection with $^D$Y library against *C. elegans* iPGM. Sequence 6-1, SEQ ID NO: 30; 6-4 and 6-5, SEQ ID NO: 31; 6-6 and 6-7, SEQ ID NO: 32; 6-9, SEQ ID NO: 30; 6-11, SEQ ID NO: 31, 6-12, SEQ ID NO: 30; 6-13 and 7-1, SEQ ID NO: 31; 7-2, SEQ ID NO: 33; 7-3, SEQ ID NO: 34; 7-4, SEQ ID NO: 35; 7-5, SEQ ID NO: 31; 7-6 and 7-7, SEQ ID NO: 30; 7-9 and 7-10, SEQ ID NO: 31; 7-12, SEQ ID NO: 30; 7-13, SEQ ID NO: 31; 7-14, SEQ ID NO: 36; 7-15, SEQ ID NO: 33; 6-14, 7-8, and 7-11, SEQ ID NO: 37. FIG. 4C is an alignment of DNA sequences identified from 5th and 6th rounds of selection with $^L$Y library against *C. elegans* iPGM. Sequences 5-1, 5-2, 5-3, 5-5, 5-8, 5-9, 5-10, 5-13, 5-14, SEQ ID NO: 38; 5-16, SEQ ID NO: 39; 5-19, SEQ ID NO: 38; 5-20, SEQ ID NO: 39; 5-21 and 5-22, SEQ ID NO: 38; 5-24, SEQ ID NO: 39; 5-28, 5-30, 6-1, 6-2, 6-3, 6-4, 6-5, and 6-6, SEQ ID NO: 38; 6-7, SEQ ID NO: 40; 6-8 and 6-9, SEQ ID NO: 38; 6-11, SEQ ID NO: 39; 6-12, SEQ ID NO: 41; 6-13, SEQ ID NO: 42; 6-14, SEQ ID NO: 40; 6-15, SEQ ID NO: 43; 6-16, SEQ ID NO: 39; 5-26, SEQ ID NO: 44. Mutations at second or third codon base are colored in purple or red, respectively.

FIG. 6A is a digital image of an initial sample of monoclinic P iPGM (iPGM-m) obtained from Wizard 3-4 D11 and FIG. 6B is a digital image showing crystals observed from the Hampton Additive HT screen D7. FIG. 6C is a digital image of crystals of an orthorhombic P iPGM (iPGM-o) obtained from Index HT F7. FIG. 6D is a digital image of crystals of a co-complex with Ce-2d.

FIG. 7A is a diagram of asymmetric unit of *C. elegans* iPGM-m showing subunit A (magenta) and B (cyan). The Mn$^{2+}$ and Zn$^{2+}$ ions are represented as blue spheres. FIG. 7B is a diagram showing a comparison of the NCS dimer subunits of *C. elegans* apo iPGM-m showing subunit A (magenta) and B (cyan) superimposed (top) and the same diagram rotated 90° in the horizontal direction (bottom). FIG. 7C is a diagram showing superposition of *C. elegans* iPGM-m (magenta) and *C. elegans* iPGM-o (cyan).

FIG. 8A shows a superposition of *C. elegans* apo iPGM-m showing subunit A (magenta) and iPGM from *Bacillus anthracis* (gray, PDB: 2IFY) superimposed. Mn$^{2+}$ and Zn$^{2+}$ ions are represented as spheres. FIG. 8B shows a superposition of *C. elegans* iPGM-m showing subunit A (magenta) and iPGM from *Bacillus stearothermophilus* (green, PDB: 1098) superimposed. FIG. 8C shows the same diagram as FIG. 8B, but rotated 90° in the horizontal direction. The arrow indicates the conformational difference in the transferase domain.

FIG. 9A shows phased anomalous difference map (mesh) at the metal binding sites of the *C. elegans* iPGM•Ce-2d complex contoured at 3σ. FIG. 9B shows metal coordination in the *C. elegans* iPGM•Ce-2d complex. Contacts between the protein and Mn$^{2+}$ (large dark sphere) ion, Zn$^{2+}$ (large light sphere) ion, and water (small spheres) are shown. FIG. 9C shows the Mg$^{2+}$ binding site for iPGM•Ce-2d. Mg$^{2+}$ ion is depicted as a large sphere and water molecules as small spheres.

FIG. 10A is a diagram of the structure of the Ce-2 macrocycle obtained from affinity selection and showing truncation to give Ce-2d and position of Cys14Ser substitution. The thioether bond and D-tyrosine are highlighted. FIGS. 10B-10D are a series of graphs showing IC$_{50}$ concentration-response curves for characterization of Ce-2 (FIG. 10B), Ce-2d (FIG. 10C) and Ce-2S (FIG. 10D) on the iPGM orthologs and dPGM isozymes using the enzyme coupled bioluminescent assay. Plots are representatives from individual experiments (N≥3), error bars are standard deviations values of technical replicates. Inset, titration of 0.5 nM, 5 nM, 50 nM, 0.5 μM and 5 μM *C. elegans* iPGM with Ce-2. FIG. 10E is a phylogenetic tree constructed for amino acid sequence alignments of seven species orthologs of PGM. Percentage bootstrap values based on 1,000 replicates are indicated at branch nodes.

FIG. 11A is a series of CRCs for Bm-1 (top), Bm-4 (middle), and Ce-3 (bottom). FIG. 11B shows CRCs for Ce-2. Significant deviation from a hyperbolic response required a 5 parameter Hill equation to fit the iPGM data in this plot. Data from the iPGM orthologs and dPGM isozymes determined from the enzyme-coupled bioluminescent assay. The iPGM concentrations for *C. elegans, B. malayi* was 5 nM, for *D. immitis, E. coli* 10 nM, *O. volvulus* 20 nM, and *E. coli, H. sapiens* dPGM, 5 nM. Plots are representative from experimental replicates listed in Table 3, error bars are defined as described in Table 3. FIG. 11C is a graph showing GEMBE analysis of macrocyclic peptides Ce-2 and Ce-2d. Green: *B. malayi* iPGM, blue: *C. elegans* iPGM, amber: *E. coli* iPGM, black: *H. sapiens* dPGM, treated with inhibitor Ce-2 (squares) or Ce-2d (diamonds). pEC$_{50}$ values from experimental replicates (N): Ce-2–(Bm iPGM) 8.37±0.04 (2); (Ce iPGM) 8.36±0.03 (1); (Ec iPGM) 8.49±0.03 (3); (Hs dPGM) no apparent activity; Ce-2d–(Bm iPGM) 7.21±0.19 (1); (Ce iPGM) 8.49±0.02 (1); (Ec iPGM) 8.50±0.02 (3); (Hs dPGM) no apparent activity. Error bars are standard deviation values of experimental replicates.

FIG. 12A shows a series of cyclic peptides and FIG. 12B shows a series of linear peptides. Hydroxyl groups and methyl groups are shaded to indicate substitutions.

FIG. 12A is a series of graphs showing activity of Ce-2S (a Cys14Ser substitution) and Ce-2a-g (C-terminal amino acid truncation analogs). FIG. 13B is a series of graphs showing activity of linear peptides Ce-L2, Ce-L2d, and Ce-2tail. *B. malayi* iPGM (■), *C. elegans* iPGM (▲), *O. volvulus* iPGM (▼), *D. immitis* iPGM (◆), *E. coli* iPGM (●), *H. sapiens* dPGM (□), *E. coli* dPGM (Δ) and PK-FLuc (●). Plots are representative from experimental replicates listed in Table 3, error bars are standard deviations values of technical two replicates.

FIG. 14 is a sequence alignment of iPGM orthologs from *C. elegans* (SEQ ID NO: 45), *B. malayi* (SEQ ID NO: 46), *O. volvulus* (SEQ ID NO: 47), *D. immitis* (SEQ ID NO: 48), *E. coli* (SEQ ID NO: 49), *S. aureus* (SEQ ID NO: 50), *B. anthracis* (SEQ ID NO: 51), *L. mexicana* (SEQ ID NO: 52), and *T. brucei* (SEQ ID NO: 53). Residues within 5 Å of Ce-2d are colored orange. Residues identical between *C. elegans* and *E. coli* iPGM are colored yellow; grey indicates hinge regions, green and blue are amino acids that ligand metal ions.

FIG. 15A shows asymmetric unit of iPGM•Ce-2d showing subunit A (magenta) and B (cyan). The $Mn^{2+}$ and $Zn^{2+}$ ions are represented as blue and tan spheres, respectively, and the cyclic peptides bound to each subunit are drawn as gray spheres. FIG. 15B shows an electron density map (mesh, Fo-Fc omit) contoured at 3σ for the peptide associated with subunit A (magenta) with numbering for the Ce-2d peptide. Residue Tyr11 is capped as an amide. FIG. 15C shows the α-helical structure of Ce-2d C-terminus Backbone trace with side chains involved in α-helix formation shown.

FIG. 16A shows one subunit of the asymmetric unit showing the binding mode of the Ce-2d macrocycle to *C. elegans* iPGM. The $Mn^{2+}$ and $Zn^{2+}$ ions are represented as blue and tan spheres, respectively, and the bound macrocycle is drawn as CPK space-filling spheres in a cavity defined by iPGM residues within 5 Å (transparent spheres). FIG. 16B shows superposition of *C. elegans* iPGM-o (cyan), *C. elegans* iPGM-m (tan) and *C. elegans* iPGM•Ce-2d (aquamarine). The Ce-2d peptide is represented as cylinders. FIG. 16C shows the macrocycle (cylinders) positioned within a cleft of iPGM represented as an electrostatic surface. FIG. 16D shows CPK space-filling representations of Ce-2d illustrating the 'capping' orientation of the five tyrosine residues (1, 3, 7, 9 and 11) and FIG. 16E shows the edge-to-face interaction of Tyr1 and Tyr9. Additional residues are indicated.

FIGS. 17A-17E are a series of panels showing Ce-2d•iPGM interactions. FIG. 17A shows hydrogen bond interactions (black dashed lines) between *C. elegans* iPGM and Ce-2d. FIG. 17B shows direct interactions and water (spheres)-mediated contacts. FIG. 17C shows the distance between the C-terminal amide of Tyr11 and the $Zn^{2+}$ and $Mn^{2+}$ ion centers. FIG. 17D shows superimposed structure of *C. elegans* iPGM_Ce-2d with that of *Staphylococcus aureus* iPGM in 2-phosphoglyceric acid bound form (PDB: 4NWX). The following S. *Aureus*: *C. elegans* residue pairs were used for alignment: 123His147, 153-154Asp177-178, 191Arg216, 185Arg210, 257Arg284, and 260Arg287. Ce-2d and 2-PG are shown as CPK space filling models. The purple spheres are the $Mn^{2+}$ ions of *S. aureus* iPGM and the blue and tan spheres are the $Mn^{2+}$ and $Zn^{2+}$ ion, respectively of *C. elegans* iPGM. FIG. 17E is an enlarged region from FIG. 17D, showing the relative locations of the 2-PG and Ce-2d as cylinder models with transparent van der Waals surfaces and alignment residue side chains clustering around 2-PG.

FIG. 18A shows *C. elegans* iPGM residues (light blue chain under transparent spheres) within 5 Å of the Ce-2d macrocycle, shown as B-factor α-chain (gold) with Leu10 and thioether linkage in green. The iPGM Ala334 residue is shown as a CPK space fill and the $Mn^{2+}$ and $Zn^{2+}$ ions are represented as blue and tan spheres, respectively. FIG. 18B shows FIG. 18A without transparent spheres, for clearer view of iPGM side chains.

FIGS. 19A-19C are a series of panels showing the structural basis underlying the pharmacologic-phylogenetic Ce-2 macrocycle series-iPGM ortholog relationship. FIG. 19A is a graph showing relationship between Ce-2 macrocycle truncation series $IC_{50}$s and iPGM orthologs. Analogs with no detectable inhibitory activity are indicated as inactive. Values are from Table 3, converted from $pIC_{50}$ where $IC_{50}=10^{-pIC50}$. Error bars represent the SD values of the log normal distributed $IC_{50}$s determined for the given peptide. FIG. 19B shows select amino acid sequence alignments of portions of iPGM orthologs (SEQ ID NOs: 45-49; full alignment shown in FIG. 14). iPGM residues within 5 Å of Ce-2d are colored orange. Residues identical between *C. elegans* and *E. coli* iPGM are colored yellow; grey indicated hinge regions; green and blue are amino acids that ligand metal ions. FIG. 19C is a diagram showing the cavity formed from *C. elegans* iPGM residues (light blue chain under transparent spheres) within 5 Å of the Ce-2d macrocycle shown as a worm α-chain (gold) representation scaled by B-factor with select side chains (Tyr3, Pro4, thioether linkage, and C-terminal Tyr11 amide) shown. The iPGM Ala334 residue is shown as a CPK space fill. Electrostatic surface of the Ce-2d binding cavity is also shown.

FIG. 20A shows the Ce-2d macrocycle as worm α-chain (gold) representation scaled by B-factor within a cavity of *C. elegans* iPGM residues (transparent spheres) formed from residues within 5 Å of cyclic peptide. The C-terminal residues, -Gly12-Thr13-Cys14-Gly15 of Ce-2 were modeled onto the iPGM•Ce-2d complex and are shown as tan sticks extending from Ce-2d. Electrostatic surface of the binding cavity is also shown. FIG. 20B shows Ce-2 van der Waals radii using a CPK model. The Cys14 sulfhydryl is shown in yellow.

SEQUENCE LISTING

Figure 1A:
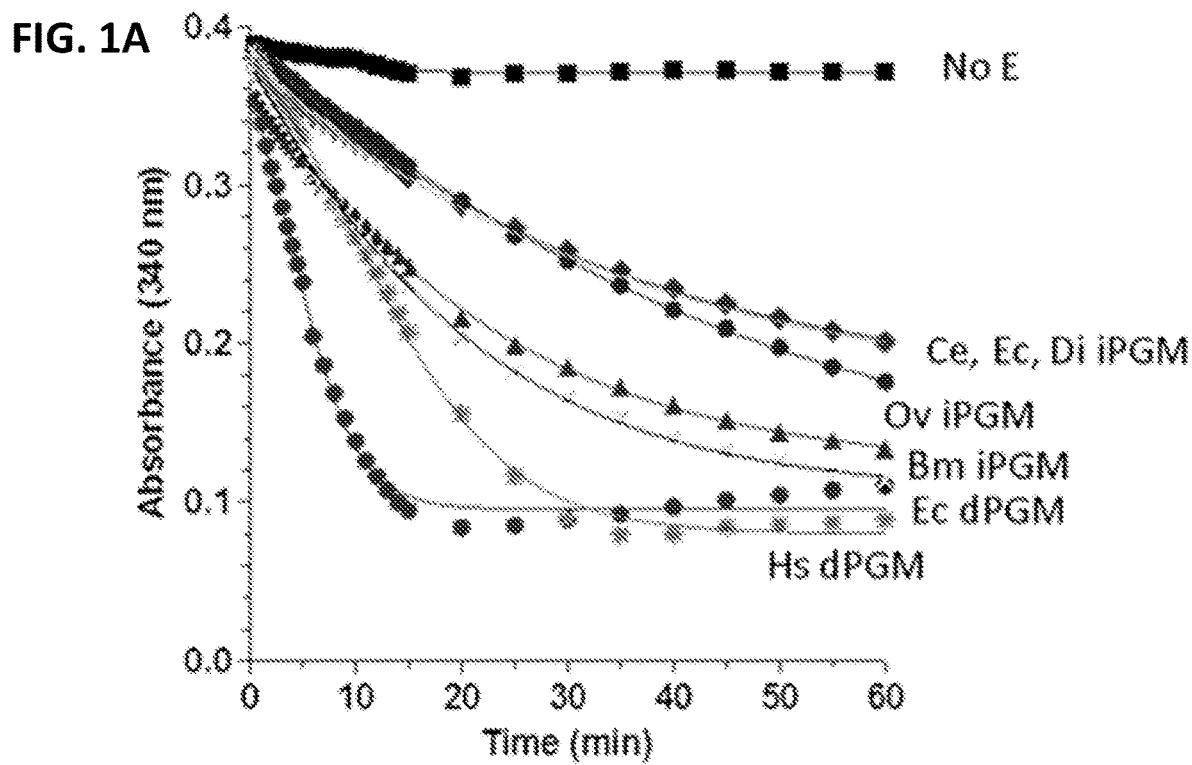

The nucleic acid and amino acid sequences provided herein and in the accompanying sequence listing are shown using standard letter abbreviations for nucleotide bases and amino acids, as defined in 37 C.F.R. 1.822. Only one strand of each nucleic acid sequence is shown, but the complementary strand is understood as included by any reference to the displayed strand.

The Sequence Listing is submitted as an ASCII text file in the form of the file named Sequence_Listing.txt, which was created on Feb. 8, 2019, and is 57 kilobytes, which is incorporated by reference herein.

SEQ ID NOs: 1-4 are amino acid sequences of cyclic peptides identified in RaPID screening with *C. elegans* iPGM.

SEQ ID NOs: 5 and 6 are amino acid sequences of modified cyclic peptides based on SEQ ID NO: 2.

SEQ ID NOs: 7-9 are amino acid sequences of linear peptides based on SEQ ID NO: 2.

SEQ ID NOs: 10-16 are amino acid sequences of cyclic peptides identified in RaPID screening with *B. malayi* iPGM.

SEQ ID NOs: 17-22 are amino acid sequences of modified cyclic peptides based on SEQ ID NO: 2.

SEQ ID NOs: 23-29 are nucleic acid sequences identified by RaPID selection against *B. malayi* iPGM.

SEQ ID NOs: 30-44 are nucleic acid sequences identified by RaPID selection against *C. elegans* iPGM.

SEQ ID NOs: 45-53 are amino acid sequences of iPGM orthologs.

SEQ ID NOs: 54-69 are the amino acid sequences of additional modified cyclic peptides based on SEQ ID NO: 2.

DETAILED DESCRIPTION

Enzymes essential for nematode survival but absent from humans represent potential targets for intervention. Essential nematode genes have been identified using comparative genomic studies of the free-living nematode *Caenorhabditis elegans*. As a result, several novel drug targets in filarial parasites have been proposed. Among the highest ranking is cofactor-independent phosphoglycerate mutase (iPGM) (EC 5.4.2.1). Silencing of ipgm in *C. elegans* and *B. malayi* leads to nematode death (Zhang et al., *J. Biol. Chem.* 279:37185-37190, 2004; Singh et al., *Infect. Dis. Poverty* 2:5, 2013), demonstrating the importance of this enzyme in nematode viability and, therefore, its potential as an anthelmintic drug target.

PGMs catalyze the interconversion of 2- and 3-phosphoglycerate (PG) in the glycolytic and gluconeogenic pathways. Although these pathways are highly conserved among different organisms, two distinct PGM isoenzymes are known to exist, namely iPGM and co-factor-dependent phosphoglycerate mutase (dPGM). The enzymes have no amino acid sequence similarity and differ in their mechanism of catalysis. iPGM is comprised of approximately 510 amino acids and catalyzes the intramolecular transfer of the phosphoryl group on the monophosphoglycerates through a phosphoserine intermediate and is the sole PGM in nematode (Jedrzej as et al., *EMBO J.* 19:1419-1431, 2000; Jedrzejas et al., *J. Biol. Chem.* 275:23146-23153, 2000). In contrast, dPGM is the form of enzyme in human that is composed of approximately 250 amino acids, and catalyzes the intermolecular transfer of the phosphoryl group between the monophosphoglycerates and the cofactor (2,3-diphosphoglycerate) through a phosphorylhistidine intermediate (Rigden et al., *J. Mol. Biol.* 315:1129-1143, 2002). While the two forms of PGM are distinct isozymes, the amino acid sequence of each isozyme family is conserved, when present, from bacteria to higher eukaryotes (Jedrzejas et al., *Prog. Biophys. Mol. Biol.* 73:263-287, 2000). The completely distinct structures and catalytic mechanism of iPGM and dPGM enzymes offer great promise for the discovery of inhibitors with high selectivity for the nematode enzymes. Furthermore, the high similarity in primary sequence and catalytic properties among the iPGMs indicates that a single inhibitor could be effective against a range of parasitic and microbial enzymes. However, iPGMs have been considered to be "undruggable," as high throughput screening (HTS) has to date identified only two low potency inhibitors of this enzyme (Crowther et al., *PLoS Neglected Tropical Diseases* 8:e2628, 2014).

Disclosed herein are a series of cyclic peptides and analogs that exhibit potent and isozyme-selective inhibition against iPGMs. The identification of the disclosed inhibitors of iPGM overturns the designation of this target as "undruggable" and provides novel anti-microbial therapeutics. The parental peptides, referred to in some instances herein as "ipglycermides," were identified from a library containing a trillion cyclic peptide members, each of which was displayed on a cognate mRNA template. These peptides have a unique lariat structure. In some examples the ring peptide consists of eight amino acid residues, one of which is D-tyrosine, closed by a thioether bond and the tail peptide consists of seven residues, one of which is L-cysteine (Cys) at the C-terminal region. Study of structure-activity relationships revealed that the ring peptide is involved in binding to iPGM orthologs, while the tail peptide region is involved in the nature of the inhibitory pharmacology and ortholog selectivity.

I. Abbreviations dPGM cofactor-dependent phosphoglycerate mutase
GEMBE gradient elution moving boundary capillary electrophoresis
HTS high throughput screening
iPGM cofactor-independent phosphoglycerate mutase
PEP phosphoenolpyruvate
PG phosphoglycerate
PGM phosphoglycerate mutase
PK pyruvate kinase
RaPID Random non-standard Peptides Integrated Discovery II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Sequences or structures associated with database accession numbers are herein incorporated by reference as present in the indicated database on Aug. 11, 2016, unless otherwise noted. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Analog or derivative: Compounds that differ from the disclosed peptides at one or more positions. An analog includes a molecule that differs in chemical structure from a parent compound, for example, differing by an increment in chemical structure (such as a difference in the length of an alkyl chain), a molecular fragment, a structure that differs by one or more functional groups, or a change in ionization. A derivative includes a biologically active molecule derived from the parent structure, for example, if one atom or group of atoms is replaced with another atom or group of atoms.

Cyclic peptide: A peptide with at least a portion forming a ring structure. In some examples, a cyclic peptide is fully cyclic, for example, having a head to tail cyclization. In other examples, a cyclic peptide includes both a ring structure and a linear peptide structure, such as formed by side chain to N-terminus, side chain to C-terminus, side chain to side chain, or backbone to backbone cyclization. In particular non-limiting examples, a cyclic peptide includes an N-terminal ring structure (e.g., formed by side chain to N-terminus cyclization) and a C-terminal linear portion (also referred to as a "tail").

Effective amount: A quantity of a specified agent sufficient to achieve a desired effect, such as an amount of an agent sufficient to inhibit or treat a disease without causing a substantial cytotoxic effect in a subject. For example, this may be the amount of an iPGM inhibitor useful for example, for reducing infection by, symptoms of, or transmission of microorganisms (such as parasites or bacteria).

Inhibiting or treating a disease: "Inhibiting" refers to reducing or delaying (or even preventing) the full development of a disease, disorder or condition, for example, in a subject who is at risk for a disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters known to one of ordinary skill in the art that are specific to the particular disease.

Isolated: An "isolated" biological component (such as a nucleic acid, protein, peptide, or pathogen) has been substantially separated or purified away from other biological components (such as cell debris, or other proteins or nucleic acids). Biological components that have been "isolated" include those components purified by standard purification methods. The term also embraces recombinant nucleic acids, peptides, or pathogens, as well as chemically synthesized nucleic acids or peptides. The term "isolated" (or "enriched" or "purified") does not require absolute purity, and can include molecules (such as peptides) that are at least 50% isolated, such as at least 75%, 80%, 90%, 95%, 98%, 99% or even 100% isolated.

Microorganism: An organism that can be seen only through a microscope. Microorganisms include bacteria, protozoa, algae, and fungi, as well as microscopic multicellular organisms, such as nematodes.

Nematode: A member of the phylum Nematoda, commonly referred to as roundworms. Nematodes include free-living species (such as the soil nematode *C. elegans*) and parasitic species. Species parasitic on humans include ascarids (e.g., *Ascaris lumbricoides*), filarias, hookworms (e.g., *Ancylostoma duodenale* or *Necator americanus*), pinworms, and whipworms. Exemplary species include *Brugia malayi*, *Wuchereria bancrofti*, and *Brugia timori*, which cause lymphedema, hydrocele, and in extreme cases, elephantiasis in humans *Onchocerca volvulus* causes onchocerciasis ("river blindness") and severe dermatitis. Parasitic nematodes also infect companion animals and livestock, including dogs and cats (e.g., *Dirofilaria immitis*; heartworm), pigs (*Trichinella spiralis*), and sheep (e.g., *Haemonchus contortus*). There are also nematode species which are parasitic on insects and plants.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compounds or molecules, such as one or more iPGM inhibitor peptides alone or in combination with additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents, and the like, for example sodium acetate or sorbitan monolaurate.

Phosphoglycerate mutase (PGM): An enzyme that catalyzes the reversible conversion of 3-phosphoglycerate to 2-phosphoglycerate. There are two classes of PGM. Cofactor-independent PGM (iPGM) (EC 5.4.2.12) and cofactor-dependent PGM (dPGM) (EC 5.4.2.11). iPGM is found in organisms including, but not limited to plants, algae, fungi, nematodes, and some bacteria (such as some Gram-positive bacteria). This enzyme catalyzes isomerization of 2-PG and 3-PG through a phosphoserine intermediate. dPGM is found in organisms including, but not limited to vertebrates, mollusks, crustaceans, insects, algae, fungi, and some bacteria (such as some Gram-negative bacteria). dPGM catalyzes isomerization of 2-PG and 3-PG through a phosphohistidine intermediate.

PGM nucleic acid and amino acid sequences are publicly available. Exemplary PGM amino acid sequences include GenBank Accession Nos. NP_871851 (*Caenorhabditis elegans*), AAQ97626 (*Brugia malayi*), AAV33247 (*Onchocerca volvulus*), AEA91534 (*Dirofilaria immitis*), NP_002620 (*H. sapiens*), and P37689 and P62707 (*E. coli*), all of which are incorporated herein by reference as present in GenBank on Aug. 11, 2016. One of ordinary skill in the art can identify additional PGM sequences and variants thereof.

Subject: Living multi-cellular vertebrate organisms, a category that includes, for example, mammals and birds. The term mammal includes both human and non-human mammals. Similarly, the term "subject" includes both human and veterinary or laboratory subjects, for example, humans, non-human primates, mice, rats, dogs, cats, sheep, pigs, horses, and cows.

III. Peptide Inhibitors of PGM

Disclosed herein are peptides that inhibit activity of PGM (for example, iPGM). In some examples, the peptides selectively or specifically inhibit activity of iPGM compared to dPGM. In some examples, an agent that selectively or specifically inhibits (for example, decreases activity of) iPGM is a compound that decreases activity of iPGM, but does not substantially decrease activity of dPGM. For example, a selective inhibitor of iPGM may decrease activity of iPGM, but not show any appreciable activity against dPGM. In other examples, a selective inhibitor of iPGM is an agent that decreases activity of iPGM by at least 2-fold more (for example, at least 5-fold more, at least 10-fold more, at least 20-fold more, 50-fold more, 100-fold more, 500-fold more, 1000-fold more, 2000-fold more, 5000-fold more, 10,000-fold more, or more) than it decreases activity of dPGM. The determination that a particular agent selectively or specifically inhibits iPGM may readily be made by using or adapting routine procedures for determining PGM activity. Exemplary methods of measuring iPGM and dPGM activity are described in Example 1, below.

In some embodiments, the disclosed peptides inhibit activity of iPGM with an $IC_{50}$ of 100 µM or less, such as 50 µM or less, 10 µM or less, 5 µM or less, 1 µM or less, 500 nM or less, 100 nM or less, 50 nM or less, 10 nM or less, 5 nM or less, 1 nM or less, or 100 µM or less. In other examples, the disclosed peptides inhibit activity of iPGM with an $IC_{50}$ of about 1 pM to 100 µM, for example, about 5 pM to 10 nM, about 10 pM to 50 nM, about 100 pM to 100 nM, about 1 nM to 100 nM, about 10 nM to 1 µM, about 100 nM to 10 µM, or about 1 µM to 100 µM.

In particular examples, the peptides are cyclic peptides; however, in some examples, linear peptides that inhibit iPGM activity are also disclosed herein. In some embodiments, the peptides are 6-20 amino acids long (such as 6-15, 8-20, or 10-20 amino acids long, for example, 6, 7, 8, 9, 10, 11, 12, 13, 14, 15, 16, 17, 18, 19, or 20 amino acids long). In some examples, the iPGM inhibitor peptide has a ring portion of 6-15 amino acids (such as 7-13, 8-12, 9-11, or 10-15 amino acids, for example, 6, 7, 8, 9, 10, 11, 12, 13, 14, or 15 amino acids) and a linear portion of 1-9 amino acids (such as 1-5, 2-7, or 4-8 amino acids, for example, 1, 2, 3, 4, 5, 6, 7, 8, or 9 amino acids). In specific non-limiting examples, the iPGM inhibitor peptide has a cyclic portion of 8 amino acids and a linear portion of 3-7 amino acid. As discussed below, analogs or derivatives of the peptides (such as peptides with modified amino acid sequence and/or modifications at the N-terminus, C-terminus, peptide backbone, or side chains) are also disclosed herein. In some embodiments, the peptides or analogs or derivatives thereof include pharmaceutically acceptable salts or esters.

In some embodiments, the PGM inhibitors include or consist of the following cyclic peptides:

YDYPG[DHCYLYGTCG] (SEQ ID NO: 1)

YDYPG[DYCYLYGTCG] (SEQ ID NO: 2)

YI[TLANPFRILHCG] (SEQ ID NO: 3)

YT[TLANPFRILHCG] (SEQ ID NO: 4)

YDYPG[DYCYLY] (SEQ ID NO: 5)

YDYPG[DYCYLYGTSG] (SEQ ID NO: 6)

[YSWPNAPEIWKCCG] (SEQ ID NO: 10)

YDL[RTPWLKRHACG] (SEQ ID NO: 11)

YQN[RSIWLYGCCG] (SEQ ID NO: 12)

Y[LEWPNCNTCG] (SEQ ID NO: 13)

Y[LDWPNCSTCG] (SEQ ID NO: 14)

Y[PEWPNCSTCG] (SEQ ID NO: 15)

Y[AVWPNCRTCG] (SEQ ID NO: 16)

YDYPG[DYCYLYGTC] (SEQ ID NO: 17)

YDYPG[DYCYLYGT] (SEQ ID NO: 18)

YDYPG[DYCYLYG] (SEQ ID NO: 19)

YDYPG[DYCYL] (SEQ ID NO: 20)

YDYPG[DHCYLY] (SEQ ID NO: 54)

YDYPG[DYC$^{Me}$YLYGTCG] (SEQ ID NO: 55)

YDYPG[DYCY$^{Me}$LYGTCG] (SEQ ID NO: 56)

-continued

YDYPGDYCYL^Me YGTCG  (SEQ ID NO: 57)
(cyclized between bracketed residues)

YDYPGDYCYLY^Me GTCG  (SEQ ID NO: 58)

YDYPGDYCYLYG^Me TCG  (SEQ ID NO: 59)

YDYPGDYCYLYGT^Me CG  (SEQ ID NO: 60)

YDYPGDYCYLYGTC^Me G  (SEQ ID NO: 61)

YDYPGDYCYLYG^Me T^Me C^Me G  (SEQ ID NO: 62)

YDYPGDYCYLYGT^Me C^Me G  (SEQ ID NO: 63)

YDYPGDYCYLYG^Me TC^Me G  (SEQ ID NO: 64)

YDYPGDYCYLYG^Me T^Me CG  (SEQ ID NO: 65)

YDYPGDYCYL^Me Y  (SEQ ID NO: 66)

YDYPGDYCYLYG^Me T  (SEQ ID NO: 67)

YDYPGDYCYL^Me YGT  (SEQ ID NO: 68)

YDYPGDYCYL^Me YG^Me T  (SEQ ID NO: 69)

In other embodiments, the PGM inhibitors include or consist of the following linear peptide:

YDYPGDYSYLYGTCG  (SEQ ID NO: 7)

Figure 12A:
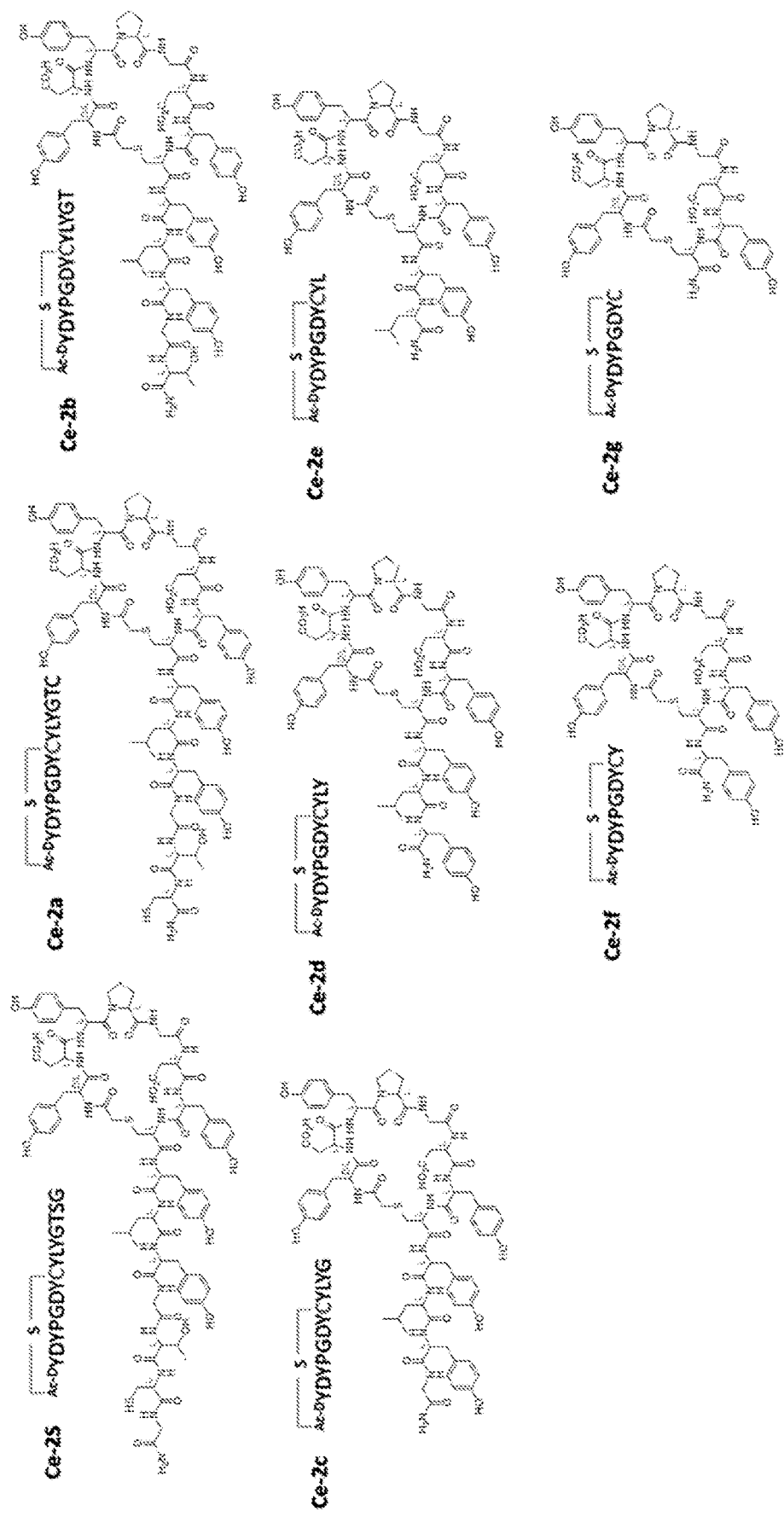
FIGS. 12A and 12B are a series of diagrams of macrocyclic peptide analogs.
Figure 21:
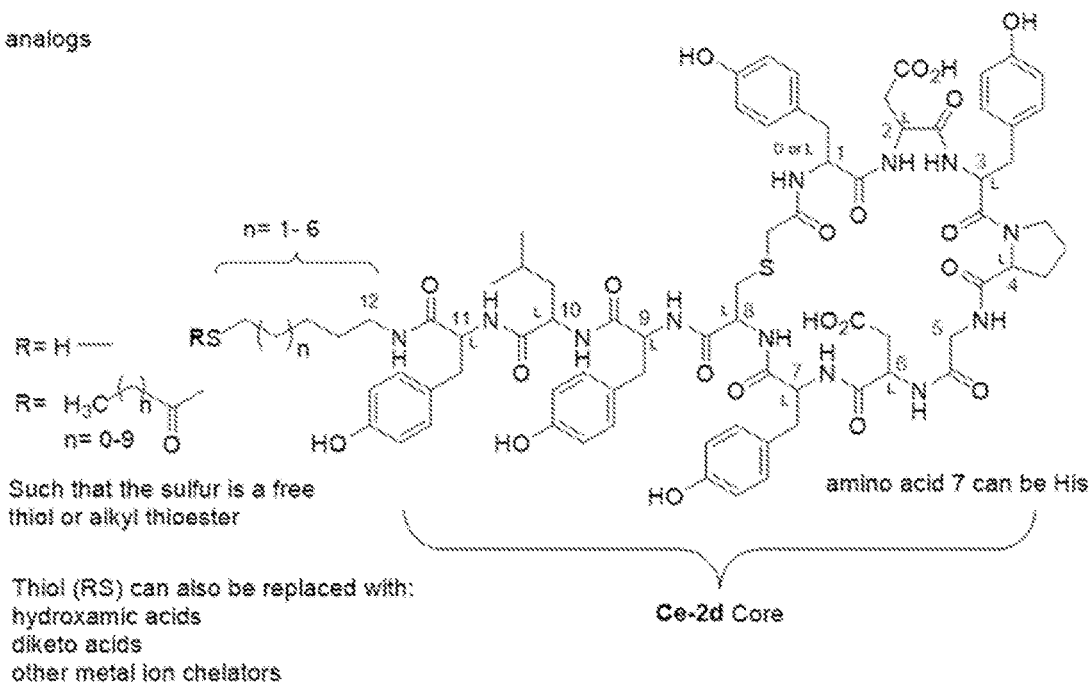
FIG. 21 is a schematic showing exemplary cyclic iPGM inhibitor peptides and analogs, based on the Ce-2d core structure.
Figure 21:
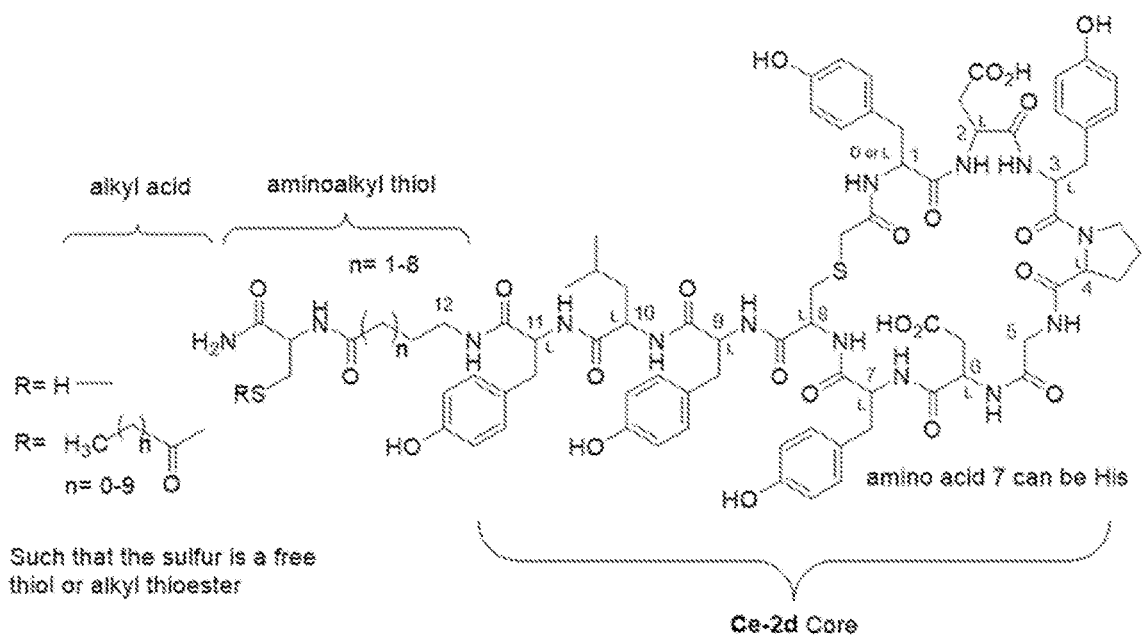

In specific examples disclosed herein, the ring portion of the cyclic peptide is produced by forming a thioether linkage between a cysteine residue in the peptide and an N-terminal chloroacetyl group (for example, as shown in Tables 2, 6, 8, and 9 and FIGS. 12A and 21). However, additional linkers can be utilized to form the cyclic peptides. For example, in some examples, the ring portion of the peptide is formed using an aromatic or aliphatic linker. For example, the cyclic portion of the peptide can be formed using an aliphatic linker, such as a 1-6 carbon chain. In other examples, the linkage may include an aromatic group.

In addition, in specific examples disclosed herein, the cyclic peptides are formed by side chain to N-terminus cyclization (for example, as shown in Tables 2, 6, 8, and 9 and FIGS. 12A and 21). However, one of ordinary skill in the art will recognize that additional types of cyclization (such as head to tail, side chain to side chain, side chain to C-terminus, or backbone to backbone cyclization) can also be utilized to form cyclic iPGM inhibitor peptides.

Also disclosed are analogs or derivatives of iPGM inhibitors, such as those described herein. An analog includes a molecule that differs in chemical structure from a parent compound, for example, differing by an increment in chemical structure (such as a difference in the length of an alkyl chain), a molecular fragment, a structure that differs by one or more functional groups, or a change in ionization. A derivative includes a biologically active molecule derived from the parent structure, for example, if one atom or group of atoms is replaced with another atom or group of atoms. Thus, in some examples, analogs or derivatives include compounds that differ from the disclosed peptides by substitution, deletion, and/or addition of one or more amino acids. Analogs or derivatives also include compounds that differ from the disclosed peptides by one or more modifications, such as substitution, addition, and/or deletion of one or more atom or group of atoms at the N-terminus, C-terminus, peptide backbone, and/or amino acid side chain of the peptide. In addition, an analog or derivative may include a combination of one or more amino acids changes and one or more changes of an atom or group of atoms of the peptide.

In some examples, analogs of the disclosed peptides include modifications to allow cyclization of the peptide. Thus, in one non-limiting example, an analog includes an N-terminal acetyl group (for example, an N-terminal chloroacetyl), which permits peptide cyclization through a thioether bond to a cysteine residue in the peptide. In other examples, the peptides (such as any one of SEQ ID NOs: 1-22 or 54-69) include a C-terminal amide modification. In some examples, the peptides include all L-amino acids, while in other examples, analogs include one or more D-amino acids. In particular, non-limiting examples, analogs include D-tyrosine (e.g., D-N-chloroacetyl tyrosine) as the N-terminal amino acid, such as Ce2 or Ce-2d.

In still further examples, an analog of the disclosed peptides includes a peptide with one or more amino acid substitutions, deletion of one or more amino acids (including, but not limited to truncation mutants), and/or addition of one or more amino acids. In another example, a derivative of the disclosed peptides includes substitution of the sulfhydryl group of a cysteine residue (such as the cysteine residue in the linear portion of any one of the disclosed peptides) with a hydroxamic acid, diketo acid, or a metal ion chelator. In further examples the peptides include a modification to increase stability (for example, resistance to proteolysis), such as one or more N-methyl amides in the linear portion of the peptide (exemplified by those shown in Table 9). In yet further examples, a carbon chain (such as a 1-8 carbon chain) is added at the C-terminus of any of the cyclic peptides disclosed herein. In still further examples, an aminoalkyl thiol (such as a C1-C8 alkyl) is added to the C-terminus of any of the cyclic peptides disclosed herein. In some examples, the C-terminal carbon chain or aminoalkyl thiol includes a free thiol, an alkyl thioester (C1-C9) or an alkyl acid at the C-terminus. Exemplary analogs are shown in FIG. 21. These are illustrated with respect to the Ce-2d core structure, but corresponding modifications may be made to any of the peptides disclosed herein. Any combination of modifications or substitutions is contemplated herein.

In additional examples, an analog of the disclosed peptides includes replacing one or more (such as 1, 2, 3, 4, or 5) tyrosine residues with either 4-F-Phe or 4-MeO-Phe. In some examples, the tyrosine residue corresponds to Tyr1, Tyr3, Tyr9, or Tyr11 of a disclosed peptide (such as SEQ ID NO: 1). In an additional example, the tyrosine residue corresponds to Tyr7 of a disclosed peptide (such as SEQ ID NO: 2). The corresponding tyrosine residues in other peptides disclosed herein can be identified by one of ordinary skill in the art. Other modifications include increasing the basicity of the molecule by reducing negative charge, for example by replacing Asp2 with Asn or His and/or by including positive charges in the alkyl linker, such as tertiary amines.

The disclosed peptides and analogs or derivatives may be in the form of one or more pharmaceutically acceptable salts or esters. Pharmaceutically acceptable salts of the disclosed peptides include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts may be prepared by standard procedures, for example by reacting the free acid with a suitable organic or inorganic base. Representative bases include ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of compounds to be used is chosen to provide the ratio desired for any particular salts. In some examples, the peptides can be treated with approximately one equivalent of pharmaceutically acceptable base to yield a neutral salt. Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH (2002).

Pharmaceutically acceptable esters include, but are not limited to, methyl, ethyl, propyl, butyl, pentyl, hexyl, cyclopropyl, cyclobutyl, cyclopentyl, cyclohexyl, cycloheptyl, cyclopentenyl, cyclopentadienyl, cyclohexenyl, cyclohexadienyl, phenyl, pyridinyl, benzyl, and the like. Pharmaceutically acceptable esters can be prepared by, for example, by treating the compound with an appropriate amount of carboxylic acid, ester, acid chloride, acid anhydride, or mixed anhydride agent that will provide the corresponding pharmaceutically acceptable ester. Typical agents that can be used to prepare pharmaceutically acceptable esters include, for example, acetic acid, acetic anhydride, acetyl chloride, benzylhalide, benzaldehyde, benzoylchloride, methyl ethylanhydride, methyl phenylanhydride, methyl iodide, and the like. In one non-limiting example, a pharmaceutically acceptable ester of the disclosed peptides is a cysteine ester (such as a cysteine alkyl ester, cysteine ethyl ester, or N-acetyl cysteine ester) or the esters shown in FIG. 21.

IV. Methods of Treating or Inhibiting Disorders

Disclosed herein are methods of treating or inhibiting disorders (such as infection) using the inhibitors of PGM described herein. In some embodiments, the methods include treating or inhibiting infection with and/or disease caused by organisms that express a PGM, such as iPGM. Organisms that express iPGM include, but are not limited to nematodes, fungi, bacteria (including Gram-positive and Gram-negative bacteria), trypanosomes, protozoan parasites, helminths, plants, and algae. In some non-limiting examples, the methods include treating or inhibiting infection with nematodes (including but not limited to *Brugia malayi, Brugia timori, Wuchereria bancrofti, Onchocerca volvulus, Ascaris lumbricoides, Ancylostoma duodenale, Necator americanus, Loa loa, Mansonella streptocerca, Mansonella perstans, Mansonella ozzardi, Dirofilaria immitis, Trichinella, Parafilaria bovicola, Onchocerca dermatan, Onchocerca ochengi, Onchocerca dukei, Stenofilaria assamensis*, and *Parafilaria multipapillosa*). In other non-limiting examples, the methods include treating or inhibiting infection with Gram-positive bacteria expressing an iPGM (including, but not limited to *Staphylococcus aureus, Streptococcus pneumoniae*, and *Bacillus anthracis*). In other examples, the methods include treating or inhibiting an infection and/or disease caused by an organism expressing an iPGM, for example, trypanosomes (such as *Trypanosoma brucei* or *Trypanosoma cruzi*) or protozoan parasites (such as *Leishmania mexicana, L. major, L. tropica, L. aethiopica, L. braziliensis, L. donovani, Plasmodium falciparum, P. vivax, P. ovale, P. malariae*, or *P. knowlesi*), *Babesia*, or *Giardia*. In another example, the methods include treating or inhibiting infection with Gram-negative bacteria that express iPGM, including *Escherichia coli*. In some examples, the infection and/or disease is caused by an organism expressing only iPGM, while in other examples, the infection and/or disease is caused by an organism expressing both iPGM and dPGM.

In particular examples, the methods include administering to a subject an effective amount of a composition that includes one or more iPGM inhibitor peptides disclosed herein. In some examples, subject is infected with one or more of a nematode, helminth, trypanosome, protozoan parasite, or bacteria. In particular examples, the subject has a disease caused by a nematode, including but not limited to lymphatic filariasis (for example, lymphedema, hydrocele, and/or elephantiasis), subcutaneous filariasis (such as dermatitis and/or blindness), or serous cavity filariasis. In other examples, the subject has heart filariasis (heartworm, for example, in dogs or cats), verminous hemorrhagic dermatitis (cattle), intradermal onchocercosis (cattle), "summer bleeding" (horses, cause by *Parafilaria multipapillosa*), or trichnosis. In other examples, the subject has a disease caused by a protozoan parasite, including but not limited to sleeping sickness (or Nagana, in cattle), Chagas' disease, leishmaniasis, giardiasis, babesiosis, or malaria. In still further examples, the subject has a bacterial infection, including but not limited to infection with *Staphylococcus aureus, Bacillus anthracis*, or *Streptococcus pneumoniae*.

Figure 12B:
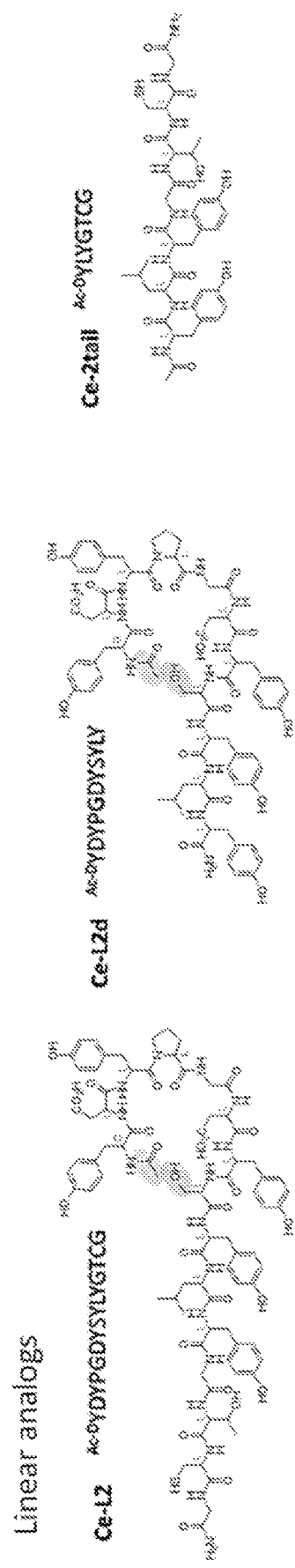

In some embodiments, the subject is administered an effective amount of a composition including one or more cyclic peptide inhibitors of iPGM, for example one or more cyclic peptides having the amino acid sequence of any one of SEQ ID NOs: 1-6, 10-22, and 54-69 (for example, one or more of the cyclic peptides shown in Tables 2, 6, 8, or 9, or FIG. 12A-12B or 21) or an analog or derivative thereof, or a pharmaceutically acceptable salt or ester thereof. In other examples, the subject is administered an effective amount of a composition including one or more linear peptide inhibitors of iPGM, for example, one or more peptides having the amino acid sequence of SEQ ID NOs: 7-9 or an analog or derivative thereof, or a pharmaceutically acceptable salt or ester thereof. In other examples, the subject is administered an effective amount of a composition including one or more cyclic peptide iPGM inhibitors and one or more linear peptide iPGM inhibitors, such as those disclosed herein. In particular non-limiting examples, the subject is administered an effective amount of a composition including peptide Ce-2

(SEQ ID NO: 2 with a cyclization between the N-terminus and Cys8) or an analog or derivative thereof, or a pharmaceutically acceptable salt or ester thereof.

The disclosed peptides can be administered by any means known to one of skill in the art, such as by intramuscular, subcutaneous, intraperitoneal, or intravenous injection, but even oral, nasal, or anal administration is contemplated. The disclosed peptides can also be administered topically, transdermally, or by local injection. In some embodiments, administration is orally, by intravenous injection, or topically. To extend the time during which the peptide is available to inhibit or treat an infection, the peptide can be provided as an implant, an oily injection, or as a particulate system. The particulate system can be a microparticle, a microcapsule, a microsphere, a nanoparticle, a nanocapsule, or similar particle. One of ordinary skill in the art is aware of methods of administering peptides to a subject. See, e.g., Banga, "Parenteral Controlled Delivery of Therapeutic Peptides and Proteins," in *Therapeutic Peptides and Proteins*, Technomic Publishing Co., Inc., Lancaster, Pa., 1995.

In some examples, the provided peptides are combined with a pharmaceutically acceptable carrier or vehicle for administration to human or animal subjects. In some embodiments, more than one disclosed peptide (for example, 1, 2, 3, 4, 5, or more peptides) can be combined to form a single preparation. Examples of suitable pharmaceutically acceptable carriers, vehicles, or excipients include sterile aqueous or non-aqueous solutions, suspensions, and/or emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The peptides and pharmaceutical compositions provided herein may be administered through different routes, such as oral, including buccal and sublingual, rectal, parenteral, aerosol, nasal, intravenous, intramuscular, subcutaneous, intradermal, and topical. They may be administered in different forms, including but not limited to solutions, emulsions and suspensions, microspheres, particles, microparticles, nanoparticles, and liposomes.

In another embodiment, it may be desirable to administer the peptides or pharmaceutical compositions locally to the area in need of treatment. This may be achieved by, for example, and not by way of limitation, local or regional infusion or perfusion, topical application, injection, catheter, suppository, or implant (e.g., implants formed from porous, non-porous, or gelatinous materials, including membranes, such as sialastic membranes or fibers), and the like.

In a specific embodiment, one or more of the disclosed peptides may be associated either by coating or impregnating an implant. In an example, the implant can be partially or completely coated with the peptide. The peptide may be attached to the implant by any chemical or mechanical bond or force, including linking agents. Alternatively, the coating may be directly linked (tethered) to the surface, such as through silane groups. In other examples, the implant may be impregnated with at least one peptide by methods known to those of skill in the art so that multiple surfaces (such as the outer and inner surfaces) of the implant include the peptide. In an additional embodiment, the implant may be coated or impregnated with materials in addition to the disclosed peptides to further enhance their bio-utility. Examples of suitable coatings are medicated coatings, drug-eluting coatings, hydrophilic coatings, or smoothing coatings.

In one embodiment, administration can be by direct injection at the site of a tissue that is to be treated. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the pharmaceutical compositions can be delivered in a controlled release system. In one embodiment, a pump can be used (see, e.g., Langer *Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., *Ann. Neurol.* 25:351-356, 1989; and Howard et al., *J. Neurosurg.* 71:105-112, 1989). Other controlled release systems, such as those discussed in the review by Langer (*Science* 249:1527-1533, 1990), can also be used.

Pharmaceutical compositions for oral use can also be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

The peptides can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostatic agents, and/or solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The amount of the peptide(s) that will be effective depends on the nature of the disorder or condition to be treated, as well as the stage of the disorder or condition. Effective amounts can be determined by standard clinical techniques. The precise dose of the peptide(s) to be employed in the formulation will also depend on the route of administration, and should be decided according to the judgment of the health care practitioner and each subject's circumstances. An example of such a dosage range is 1 µg/kg to 200 mg/kg body weight (for example, about 5 µg/kg to 1 mg/kg, about 10 µg/kg to 5 mg/kg, about 100 µg/kg to 20 mg/kg, about 0.2 to 100 mg/kg, about 0.5 to 50 mg/kg, about 1 to 25 mg/kg, about 5 to 75 mg/kg, about 50 to 150 mg/kg, or about 100 to 200 mg/kg) in single or divided doses. Another example of a dosage range is 1 µg/kg to 100 mg/kg body weight (for example, about 1 to 100 µg/kg, 10 µg/kg to 1 mg/kg, 100 µg/kg to 5 mg/kg, 1 to 10 mg/kg, about 5 to 25 mg/kg, about 20 to 50 mg/kg, about 40 to 80 mg/kg, or about 60 to 100 mg/kg) in single or divided doses. For example, a suitable dose is about 0.1 mg/kg, about 0.2 mg/kg, about 0.5 mg/kg, about 0.75 mg/kg, about 1 mg/kg, about 2 mg/kg, about 5 mg/kg, about 7.5 mg/kg, about 10 mg/kg, about 15 mg/kg, about 25 mg/kg, about 50 mg/kg, about 75 mg/kg, or about 100 mg/kg. Unit dosage forms are also possible, for example 0.01 mg, 0.05 mg, 0.1 mg, 0.25 mg, 0.5 mg, 1 mg, 2 mg, 5 mg, 10 mg, 15 mg, 20 mg, 25 mg, 50 mg, 100 mg, 150 mg, 200 mg, 500 mg, or up to 1000 mg per dose. However, other higher or lower dosages also could be used, as can be determined by in vitro and/or in vivo testing.

The specific dose level and frequency of dosage for any particular subject may be varied and will depend upon a variety of factors, including the activity of the specific compound, the metabolic stability and length of action of that compound, the particular disease or disorder to be treated, the age, body weight, general health, sex, diet, mode and time of administration, rate of excretion, and/or any drug combinations administered. Treatment can involve daily or multi-daily, weekly, bi-monthly, or monthly doses of compound(s) over a period of a few days or weeks to months, or even years.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art.

The disclosed peptides can be used alone or in combination therapy with other compositions or drugs used to treat the described conditions. Such combination therapies include, but are not limited to simultaneous or sequential administration of the drugs involved. For example, in the treatment of nematodes, the peptide formulations can be administered in combination with any one or more of the anti-filarial therapies currently in use, for example, diethylcarbamazine, albendazole, levamisole, doxycycline, and/or ivermectin. Similarly, in the treatment of bacterial infection, the peptide formulations can be administered in combination with one or more antibiotics. One of ordinary skill in the art can identify appropriate combination therapies based on the infection or disease being treated.

EXAMPLES

The following examples are provided to illustrate certain particular features and/or embodiments. These examples should not be construed to limit the disclosure to the particular features or embodiments described.

Example 1

Materials and Methods

Preparation of PGM Enzymes:

All PGM enzymes were cloned into pET21a(+) and expressed in the *Escherichia coli* strain C2566/T7 Express (fhuA2 lacZ::T7 gene1 [lon] ompT gal sulA11 R(mcr-73::miniTn10-TetS)2[dcm] R(zgb-210::Tn10-TetS) endA1 Δ(mcrC-mrr)114::IS10) (New England Biolabs) and expressed and purified as previously described (Raverdy et al., *Mol. Biochem. Parasitol.* 156:210-216, 2007; Zhang et al., *J. Biol. Chem.* 279:37185-37190, 2004). Briefly, optimum conditions for production of soluble recombinant iPGM involved growth of cultures at 37° C. to 0.60600, induction with 0.1 mM IPTG overnight at 16° C. The His-tagged proteins were purified on a 5 ml HiTrap™ chelating HP column (GE Healthcare; Pittsburgh, Pa.) using an AKTA FPLC following manufacturer's instructions. After application of the sample, the column was washed with five column volumes of buffer A (20 mM NaPO$_4$, 300 mM NaCl, 10 mM imidazole, pH 7.4) followed by 10 column volumes of 92% buffer A:8% buffer B (20 mM NaPO$_4$, 300 mM NaCl, 400 mM imidazole, pH 7.4). Protein was then eluted using a linear gradient (8-100%) of buffer B equivalent to 40-400 mM imidazole.

Fractions containing iPGM-His6× were pooled, dialyzed against dialysis buffer (40 mM Tris-HCl, 200 mM NaCl and 50% glycerol, pH 7.5) and stored at −20° C. prior to use. Purity of the protein was estimated by 4-20% SDS-PAGE and the protein concentration was determined using the Bradford assay. Protein concentrations were 10 mg/ml or higher.

The sequences encoding the PGMs used in this study have the following NCBI (GenBank) Accession numbers: *C. elegans* iPGM, long form NP_871851.1; *C. elegans* iPGM, short form NP_491896.1; *B. malayi* iPGM AAQ97626.1; *O. volvulus* iPGM, AAV33247.1; *Dirofilaria immitis* iPGM, AEA91534.1; *Homo sapiens* dPGM, NP_002620.1; *E. coli* iPGM, P37689.1; and *E. coli* dPGM, P62707.2, all of which are incorporated by reference herein as present in GenBank on Aug. 11, 2016.

iPGM and dPGM Assays:

Phosphoglycerate mutase activity was measured either as a continuous or endpoint output assay. The continuous assay was based on lactate dehydrogenase oxidation of NADH as monitored at an absorbance of 340 nm using pyruvate supplied through a series of coupling enzymes as previously described for *C. elegans* and *B. malayi* iPGMs (Zhang et al., *J. Biol. Chem.* 279:37185-37190, 2004; White et al., *Eur. J. Biochem.* 207:709-714, 1992), adapted here in 1536-well microtiter plate format for the PGM orthologs and isozymes used in this study. Initial rate conditions determined from the continuous assay were used to calibrate an end-point bioluminescent assay format for a PGM profiling panel to evaluate the inhibitors.

Figure 1B:
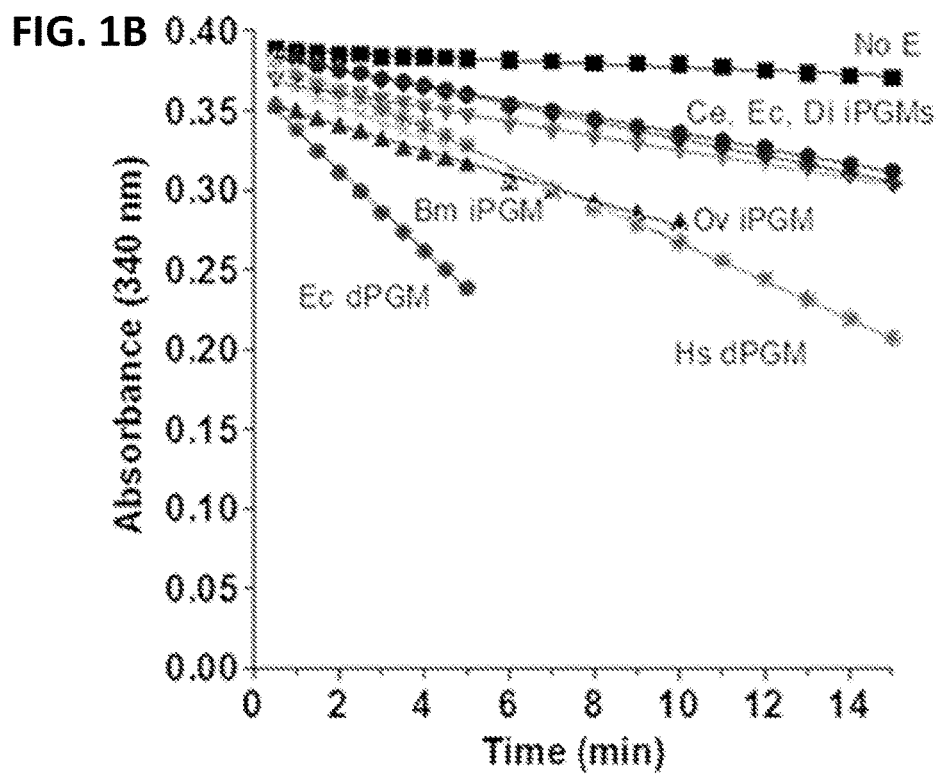

1536-Well Format Kinetic Assay:

Briefly, the forward glycolytic PGM catalyzed conversion of 3-phosphoglycerate (3-PG) to 2-phosphoglycerate (2-PG) was measured indirectly by monitoring the consumption of NADH through a coupled enzyme reaction. Four μL of the respective PGM enzyme was dispensed into black clear-bottom 1536 well plates (Cat #789092-F, Greiner Bio-One North America) in a pH 8.0 assay buffer with the BioRaptr™ FRD microfluidic workstation (Beckman Coulter, Brea, Calif.), for a final concentration of 30 mM Tris-HCl, 5 mM $MgSO_4$, 20 mM KCl and 0.08% BSA. Two μl of 3-PG substrate was added to each enzyme solution in a coupled enzyme assay buffer using the BioRaptr™ FRD, for a final assay concentration of 3 mM ADP, 500 μM NADH, 0.3 units enolase, 0.3 units pyruvate kinase, and 0.3 units lactate dehydrogenase. To confirm the 3-PG apparent $K_m$ for several PGMs, 4 μL of *B. malayi* iPGM, *C. elegans* iPGM, or *H. sapiens* dPGM enzymes were dispensed as above at a final concentration of 1 nM in pH 8.0 assay buffer. Two μl of an 11-point titration series of 3-PG substrate ranging from 0.083-2.0 mM was added to each enzyme solution in the coupled enzyme assay buffer. A 60 min time course was read for each enzyme-substrate solution at an absorbance of 340 nm on an Infinite® M1000 PRO microplate reader (Tecan Group Ltd), as shown in FIG. 1A. NADH consumption was plotted as absorbance (340 nm) vs. time (seconds) in GraphPad Prism software (GraphPad Software, Inc.) for each of the enzyme-substrate titrations and the slope of the linear phase for each substrate concentration was calculated for the respective enzymes (FIG. 1B). The initial rate ($v_i$) for each enzyme-substrate reaction was determined and plotted against molar substrate concentration to generate Michaelis-Menton curves, while the reciprocal of the rate and molar substrate concentrations were re-plotted as Lineweaver-Burk graphs in GraphPad Prism and apparent $K_m$ values were estimated for each respective enzyme.

1536-Well Format Luminescence Assay:

ATP generated from the pyruvate kinase (PK) catalyzed conversion of phosphoenolpyruvate (PEP) to pyruvate was utilized to configure a luminescence output for the PGM enzyme panel. Various concentrations of *B. malayi* iPGM, *C. elegans* iPGM, and *H. sapiens* dPGM enzymes ranging from 1-5 nM final concentrations were dispensed in a total volume of 4 μl of the above assay buffer into respective wells of 1536-well white/solid bottom plates (Cat #789173-F, Greiner Bio-One North America) using the BioRaptr™ FRD workstation. Two μl of 3-PG substrate solution prepared at the estimated $K_m$ concentration was added to each enzyme solution as described above, for a final assay concentration of 0.4 mM 3-PG, 3 mM ADP, 0.3 units enolase, and 0.3 units PK. Enzyme-substrate solutions were incubated at room temperature for 5 min, 4 μl Kinase-Glo® Plus reagent (Promega Corporation, Madison, Wis.) was added to each reaction with the BioRaptr™ FRD workstation, plates were incubated at room temperature for 10 min protected from light, and a luciferase-based ATP detection read-out was measured by a ViewLux® plate reader (PerkinElmer, Waltham, Mass.). To expand the PGM enzyme selectivity panel to additional PGMs, luminescence measurements for *O. volvulus* iPGM, *D. immitis* iPGM, *E. coli* iPGM, and *E. coli* dPGM enzymes were measured as described above for each enzyme titrated from 1-20 nM in the presence of 0.4 mmol/L substrate. The enzyme concentration for each PGM that generated relatively equivalent luminescence RLU across the panel was selected for macrocyclic peptide and peptide analog profiling.

The pyruvate kinase (PK) coupling enzyme was included as an additional specificity control in the enzyme panel. PK concentrations of 0.3 units (~930 nM) or 0.15 units (~460 nM) were dispensed in a total volume of 4 μl of the above assay buffer into respective wells of 1536-well white/solid bottom plates as previously described. Two μl of PEP substrate solution prepared at an equivalent concentration to 3-PG substrate were added to the PK enzyme solution as described above, for a final assay concentration of 0.4 mM PEP and 3 mM ADP. The protocol for this assay profile is given in Table 1.

SPPS cyclic peptides were tested under initial assay conditions described in Table 1 designed to give robust and uniform signal to background across the 7 enzyme PGM panel. Concentration response curves (CRCs) were fit using a 4 or 5 parameter Hill equation (below). Model selection was determined by an extra-sum-of-squares F test for each ortholog condition. The majority of cyclic peptides displayed hyperbolic responses; those with steep Hill slopes or requiring a 5 parameter fit were revaluated at assay conditions employing lower iPGM concentrations.

5 Parameter Hill Equation:

$$Y = \frac{(S_{max} - S_0)}{[1 + 10^{(n(LogXb)-X)}]^S}$$

Where $$LogXb = LogEC50 + \frac{1}{n}Log(2^{(\frac{1}{S})} - 1)$$

Where S0 is the signal at zero concentration, Smax is the signal at infinite concentration, n is the Hill slope, Log $EC_{50}$ is the log of the concentration at half-maximal signal, X is the log of the concentration, and S is the asymmetry parameter.

Figure 2A:
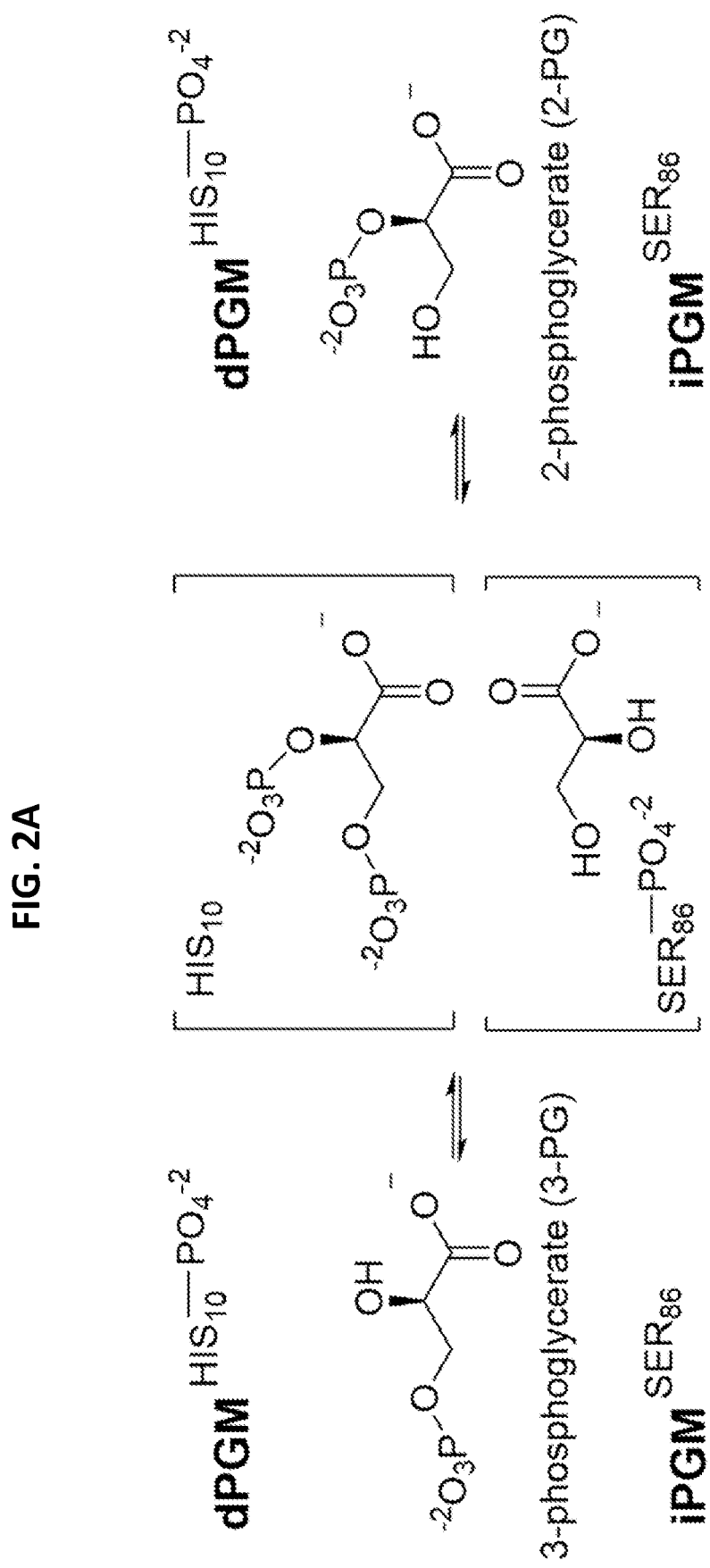
FIGS. 2A-2C are a series of panels showing species-dependent PGM catalytic mechanisms and assay methods to detect 2- and 3-phosphoglycerate (2-PG, 3-PG).
Figure 2B:
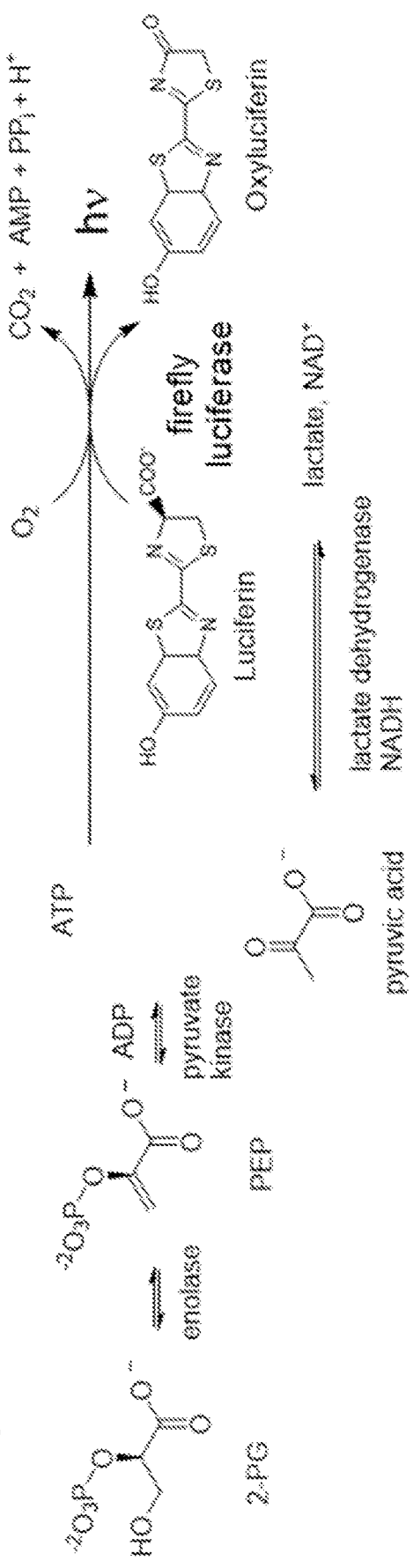
Figure 2C:
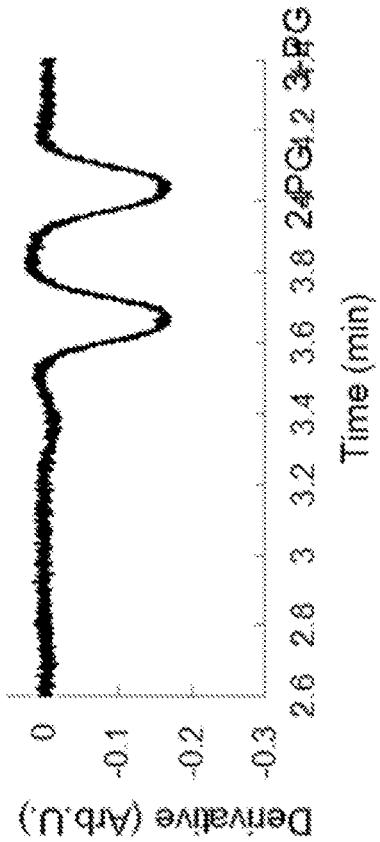
Figure 2C:
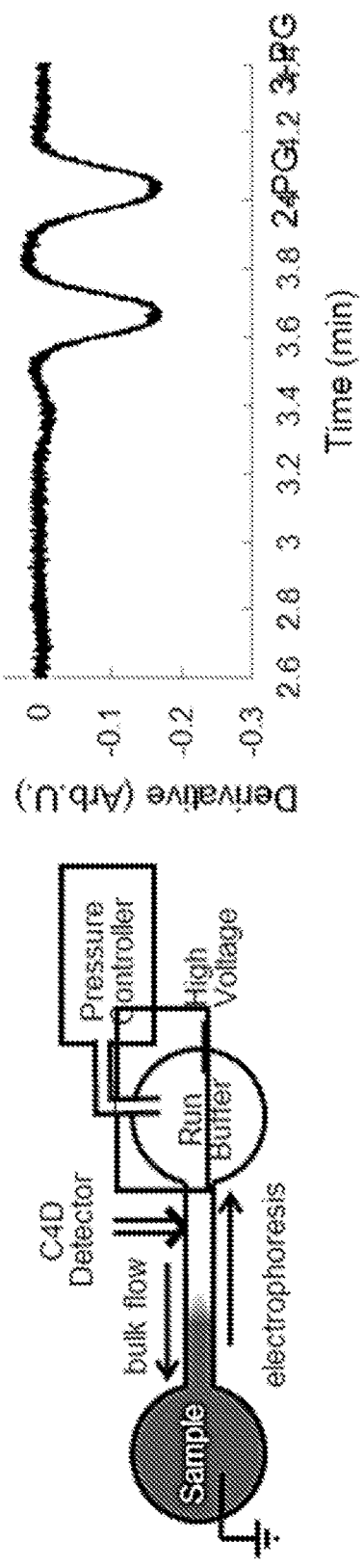

*C. elegans* iPGM Titration:

The 1536-well format luminescence assay (above) was adapted to evaluate enzyme concentration on IC50 of Ce-2. *C. elegans* iPGM 10 nM to 50 pM concentration range was tested across a 16-pt 1:3 dilution of Ce-2 from 3.83 μM to 0.27 pM final concentration, while 1 μM to 50 nM enzyme concentration range was tested across a 16-pt 1:2 dilution of Ce-2 from 3.83 μM to 117 pM final concentration. *C. elegans* iPGM concentrations of 1 nM-50 pM were incubated with 0.4 mM 3PG substrate solution for 15 min at room temperature and read on the ViewLux plate reader with standard assay settings (1 sec exp, medium gain, slow speed, 2× binning). 100 nM-5 nM enzyme concentrations were incubated with 0.4 m 3PG substrate solution for 5 min at room temperature and read on the ViewLux with standard assay settings. Enzyme concentrations of 500 nM and 1 μM were incubated with substrate for 5 min as above, but ViewLux plate reader settings were reduced to eliminate overexposure (1 sec exp, medium gain, medium speed, 2× binning). For the assay, 23 nL of the peptide titration series from a 16-point compound dispense plate were simultaneously transferred to 1536-well assay plates (Cat #789092-F, Greiner Bio-One North America) using a 1536-pin tool (Wako) for a final concentration range of 3.8 µM-0.27 pM.

with electrophoresis buffer (30 mM Tris-HCl pH 8.0, 20 mM $MgCl_2$), and enzyme reactions were mixed and run directly in the sample reservoir. The magnesium concentration in the electrophoresis buffer was chosen to optimize the resolution between the 2-PG and 3-PG signals (Schaeper et al., *J. Capillary Electrophor.* 3:215-221, 1996) in the GEMBE electropherogram (FIG. 2C and FIGS. 3A-3B).

TABLE 1

PGM ortholog and isozyme 1536-well plate assay protocol

| Step | Parameter | Value | Target | Description |
|---|---|---|---|---|
| 1a | Reagent | 4 µL | *B. malayi* iPGM | No Enzyme control and Enzyme |
| 1b | Reagent | 4 µL | *C. elegans* iPGM | solutions (5 nM *B. malayi* iPGM, 5 |
| 1c | Reagent | 4 µL | *H. sapiens* iPGM | nM *C. elegans* iPGM, 5 nM |
| 1d | Reagent | 4 µL | *O. volvulus* iPGM | *H. sapiens* dPGM, 20 nM *O. volvulus* |
| 1e | Reagent | 4 µL | *D. immitis* iPGM | iPGM, 10 nM *D. immitis* iPGM, 10 |
| 1f | Reagent | 4 µL | *E. coli* iPGM | nM *E. coli* iPGM, and 4 nM *E. coli* |
| 1g | Reagent | 4 µL | *E. coli* dPGM | dPGM final concentrations); white/ solid bottom base plate (Greiner) |
| 1h | Reagent | 4 µL | PK-Fluc ctrl | 0.15 U PK final concentrations; white/solid bottom high base plate (Greiner) |
| 2 | Cyclic peptides | 23 nL | | Cyclic Peptides profiled across iPGM orthologs and dPGM isozymes (5 mM-84.7 nM; 19.1 µM-324.6 pM; 11-pt 1:3 titration series) or vehicle (DMSO) control; Peptides transfer by Pintool; Control = No Enzyme |
| 3 | Incubation | 20-30 min | | Peptide interaction with enzyme |
| 4 | Reagent | 2 µL | | 3-phoshoglycerate (3PG) and PEP; PEP only for PK control |
| 5 | Incubation | 10 min | | Ambient temperature; dark |
| 6 | Reagent | 3 µL | | Kinase-Glo Plus reagent |
| 7 | Incubation | 20-30 min | | Ambient temperature; dark |
| 8 | Measurement | ViewLux | | Luminescence mode, 1 sec exposure; gain = med; speed = slow; binning = 2X |

| Step | Notes |
|---|---|
| 1 | Assay buffer: 30 mM Tris-HCl, pH 8.0, 5 mM $MgSO_4$, 20 mM KCl, 0.12% BSA + 6-30 nM enzyme or 0.0375 units/µL pyruvate kinase<br>5X Assay Buffer: 150 mM Tris-HCl, pH 8, 25 mM $MgSO_4$, 100 mM KCl, 0.6% BSA |
| 4 | Substrate buffer for PGM enzymes: 30 mM Tris-HCl, pH 8.0, 5 mM $MgSO_4$, 20 mM KCl, 9 mM ADP, and 0.15 units/µL each of enolase and pyruvate kinase + 1.2 mM 3PG<br>Substrate buffer for PK enzyme: 30 mM Tris-HCl, pH 8.0, 5 mM $MgSO_4$, 20 mM KCl + 1.2 mM PEP<br>5X Assay buffer: 150 mM Tris-HCl, pH 8, 25 mM $MgSO_4$, 100 mM KCl<br>Final PGM assay buffer concentrations: 30 mM Tris-HCl, pH 8.0, 5 mM $MgSO_4$, 20 mM KCl, 3 mM ADP, and 0.3 units each of enolase and pyruvate kinase + 4-20 nM PGM enzyme and 0.4 mM 3PG (or 0.15 units PK + 0.4 mM PEP) |

Gradient Elution Moving Boundary Electrophoresis (GEMBE):

GEMBE was used for the direct monitoring of the activity of the enzyme iPGMs via label-free measurement of the substrate and product, 2-PG and 3-PG. A custom built apparatus was used to perform gradient elution moving boundary electrophoresis (Strychalski et al., *Anal. Chem.* 83:6316-6322, 2011). The separation channel consisted of a 5 cm length of capillary (360 µm OD, 15 µm ID) joining a custom machined 200 µL sample reservoir and 2000 µL buffer reservoir. Pressure in the headspace of the buffer reservoir was controlled using a Series 600 automated pressure calibrator (Mensor, San Marcos, Tex.). Platinum electrodes were inserted into the reservoirs to apply voltage across the separation channel. The capillary passed through a TraceDec® capacitively-coupled contactless conductivity detector (Innovative Sensor Technologies, Strasshof, Austria) with the detection spot located approximately 2 cm from the sample reservoir. The buffer reservoir was filled The equilibrium ratio of 2-PG to 3-PG predicted from the standard free energy is approximately 1:7 at room temperature (Clarke et al., *Biochem. J.* 139:491-497, 1974). Consequently, with the GEMBE assay, the typical change in signal is approximately 11× larger for the reaction starting with 2-PG and converting to 3-PG than for the reaction starting with 3-PG and converting to 2-PG. For the cofactor independent enzymes (*B. malayi* iPGM, *C. elegans* iPGM, and *E. coli* iPGM), the mutase reaction was found to be reversible in the GEMBE assay. Therefore, reactions with those enzymes were run starting with pure 2-PG and monitoring the conversion of 2-PG to 3-PG to maximize signal. For the cofactor dependent enzyme, *H. sapiens* dPGM, the mutase reaction was found to be irreversible in the GEMBE assay, with much faster reaction rates found for the conversion of 3-PG to 2-PG. Reactions with that enzyme were therefore started with pure 3-PG and the conversion of 3-PG to 2-PG was monitored.

The analytical separation of the product and substrate was carried out as follows. The buffer reservoir pressure was maintained at 30 kPa between separations and during sample loading. Once a sample was loaded and the GEMBE separation initiated (as described below), the pressure was reduced to 20 kPa for 30 s with the high voltage off. The high voltage (+2 kV) was then turned on, and the pressure was further reduced to a starting pressure of between 750 Pa and 2500 Pa and held constant for approximately 14 seconds. These results were obtained over several months using different capillaries with nominally identical properties. Because of slight differences in the electro-osmotic properties and inner diameter of the capillaries, the optimal starting pressure varied between sets of analyses. The pressure was then reduced at a rate of 12.5 Pa/s until both 2-PG and 3-PG had been detected (216 s to 240 s). The pressure was then increase to 20 kPa and held constant for 10 s. The high voltage was turned off, and the pressure was increased to 30 kPa for at least 30 s before the start of the next GEMBE separation. The GEMBE separation was repeated 5 or 6 times for each sample, to monitor the conversion of substrate to product over a period of approximately 25 minutes.

Stock solutions of 2-PG and 3-PG were prepared at concentrations of 4 mM in electrophoresis buffer (30 mM Tris-HCl pH 8.0, 20 mM $MgCl_2$). Enzyme dilution buffer was prepared with 30 mM Tris-HCl pH 8.0, 20 mM $MgCl_2$, 6.4 mg/mL BSA. Inhibitor solutions were prepared in DMSO by 2-fold serial dilution to cover a range of at least 100-fold in concentration. PGM enzyme stock solutions were in 50% glycerol and were stored at −20° C. Final enzyme concentrations used were chosen to give similar reaction rates for the GEMBE assays. Before each enzyme reaction mixture was loaded, the sample reservoir was rinsed with electrophoresis buffer.

For the GEMBE measurements with Ce-2 and Ce-2d, the enzyme reactions were mixed and initiated according to the following: working solutions of *C. elegans*, *B. malayi*, *E. coli* iPGM, and *H. sapiens* dPGM were prepared by volumetric dilution from 93, 136, 62 and 125 μM stocks with enzyme dilution buffer to enzyme concentration of 47, 34, 250 and 21 nM respectively. To initiate a reaction, 159 μL of electrophoresis buffer was added to the sample reservoir, followed by 1 μL of inhibitor solution in DMSO (or pure DMSO for no-inhibitor controls) and 20 μL of the enzyme working solution. Mixing was achieved with vigorous pipetting. Five minutes after addition of the enzyme, 20 μL of substrate (2-PG or 3-PG) stock solution was added, and the sample was again mixed with pipetting. Forty-five seconds after addition of the substrate, the first analytical separation was started. The final concentrations of all components in the reaction were: 30 mM Tris HCl, 20 mM $MgCl_2$, 0.64 mg/mL BSA, 400 μM substrate, 0.5% v/v DMSO, inhibitor ranging from 195 pM to 2.5 μM, and either 3.4 nM *B. malayi* iPGM, 4.6 nM *C. elegans* iPGM, 25 nM *E. coli* iPGM, or 2.1 nM *H. sapiens* dPGM.

Analysis of the GEMBE data and calculation of reaction rates was similar to that previously reported (Ross et al., *Anal. Chem.* 80:9467-9474, 2008). Briefly, the detector signal vs. time data for each electropherogram (see FIG. 3A, for example) was fit to a functional form consisting of the sum of three complementary error functions and a quadratic baseline:

$$\text{signal}(t) = A_0 + A_1 t + A_2 t^2 + \frac{C_1}{2}\text{erfc}\left(\frac{t-t_1}{\sqrt{2}\,\sigma_1}\right) + \frac{C_2}{2}\text{erfc}\left(\frac{t-t_2}{\sqrt{2}\,\sigma_2}\right) + \frac{C_3}{2}\text{erfc}\left(\frac{t-t_3}{\sqrt{2}\,\sigma_3}\right)$$

The three error functions correspond to 2-PG, 3-PG, and an unknown species present in the enzyme stock solutions. Calibration measurements indicated that the resulting best fit values for C2 and C3 were proportional to the concentration of the analytes, 2-PG and 3-PG, respectively. The percent conversion was then calculated from:

$$\text{percent conversion} = \frac{C_3}{C_2 + C_3} \cdot 100$$

The reaction rate was determined by the slope of a linear fit to the percent conversion vs. reaction time data for the first four GEMBE separations with each sample. The reaction rate was normalized by the rate of reaction from a no inhibitor control. Data were modeled to a four parameter Hill equation for determination of $IC_{50}$s using Prism Graph-Pad.

Macrocyclic Library Design:

Two thioether-macrocyclic peptide libraries were constructed with either N-(2-chloroacetyl)-L-tyrosine ($ClAc^LY$) or N-(2-chloroacetyl)-D-tyrosine ($ClAc^DY$) as an initiator by using the Flexible in vitro Translation (FIT) system (Goto et al., *Nat. Protoc.* 6:779-790, 2011). The corresponding mRNA library is designed to have an AUG ($ClAc^{L/D}Y$) initiator codon followed by 4-12 NNK random codons (N=G, C, A or U; K=G or U), which code random proteinogenic amino acid residues, followed by a fixed UGC codon that assigns Cys. The theoretical diversity of the macrocycles based on the quantitative assessment of efficiencies of the individual transformation steps (see below) is at least $10^{12}$. After in vitro translation, a thioether bond formed spontaneously between the N-terminal ClAc group of the initiator$^{L/D}$Tyr residue and the sulfhydryl group of a downstream Cys residue.

Affinity Selection and Enrichment:

Affinity selections were independently performed with $^DY$ library against *B. malayi* iPGM (His10-tagged) and $^{D/L}Y$ libraries against *C. elegans* iPGM (His10-tagged) by employing the Random non-standard Peptides Integrated Discovery (RaPID) system. The mRNA library, $ClAc-_L$-Tyr-tRNA$^{fMet}_{CAU}$ and $ClAc-_D$-Tyr-tRNA$^{fMet}_{CAU}$ were prepared as reported (Hayashi et al., *ACS Chem. Biol.* 7:607-613, 2012; Hipolito et al., *Molecules* 18:10514-10530, 2013). One μM mRNAs library were ligated with 1.5 μM puromycin linker using a T4 RNA ligase at 25° C. for 30 min and purified. Then, 1.4 μM mRNA-puromycin conjugate and 50 μM ClAc-L-Tyr-tRNA$^{fMet}_{CAU}$ or $ClAc-_D$-Tyr-tRNA$^{fMet}_{CAU}$ were used in a methionine-deficient FIT system to generate respective peptide libraries. The in vitro translation reaction were performed at 37° C. for 30 min with an extra incubation at 25° C. After an addition of EDTA solution (200 mM, 15 μL), the reaction solution was incubated at 37° C. for 30 min to facilitate macrocyclization and subject to pre-washed Sephadex G-25 columns to remove salts. The desalted solution of peptide-mRNA was applied to Dynabeads® His-tag Isolation & Pulldown magnetic beads (Thermo-Fisher Scientific) to remove undesired beads binders. This process is called pre-clearance and was repeated trice. After the pre-clearance, the peptide-mRNA solution was incubated with *B. malayi* iPGM- or *C. elegans* iPGM-immobilized Dynabeads for 30 min at 4° C. to obtain iPGM-binders. This process is referred to as positive selection. The selected fused peptide-mRNAs on the beads were reverse transcribed by M-MLV reverse transcriptase (Promega, Madison, Wis.) for 1 h at 42° C. The fused peptide-cDNAs were isolated from the beads by using in 1×PCR reaction buffer and heated 5 min at 95° C. The amount of eluted cDNAs were measured by quantitative PCR. The remaining cDNAs were amplified by PCR, purified and transcribed into mRNAs as a library for the next round of selection. The library preparation, preclearance and positive selection were one round of the enrichment processes. Significant cDNAs enrichments were observed at the sixth round and seventh round for *B. malayi* iPGM and *C. elegans* iPGM, respectively. The recovered cDNAs were ligated into the pGEM-T-Easy vector (Promega), using TA-cloning. The vectors were cloned into DH5a competent cells; individual clones were picked and sequenced (FIGS. 4A-4C).

Figure 5:
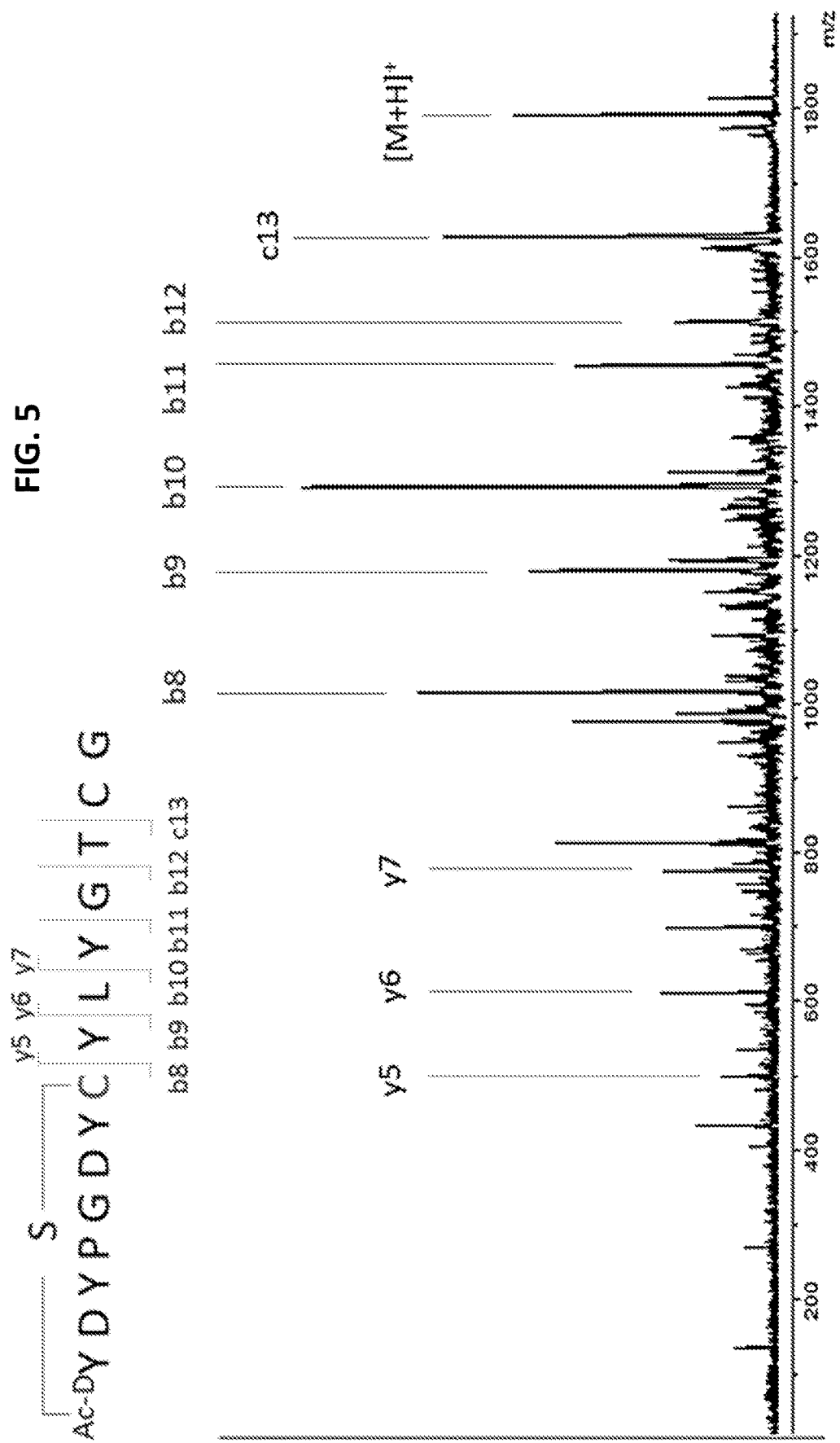
FIG. 5 is a MSMS spectrum and fragment analysis of Ce-2 by MALDI-TOF/TOF. b-type, y-type and c-type fragment ions are indicated by number. The parent ion [1\4+H]$^+$ of Ce-2 is 1790.66. Ce-2 peptide sequence (SEQ ID NO: 2) is shown.

Chemical Synthesis of Macrocycles and Analogs:

Macrocycles were chemically synthesized using a Syro Wave™ automated peptide synthesizer (Biotage, Charlotte, N.C.) by Fmoc solid-phase peptide synthesis as previously described (Morimoto et al., *Angew Chem. Int. Ed. Engl.* 51:3423-3427, 2012; Yamagata et al., *Structure* 22:345-352, 2012). Briefly, the chloroacetyl group or acetyl group was coupled onto the N-terminal amide group for the formation of cyclic or linear peptide analogs respectively after the automated synthesis. Peptides were cleaved by a solution of 92.5% trifluoroacetic acid (TFA), 2.5% water, 2.5% triisopropylsilane, and 2.5% ethanedithiol and precipitated by diethyl ether. To conduct the cyclization reaction, peptide pellet was dissolved in 10 mL DMSO/0.1% TFA in water (1:1), adjusted the pH>8 by addition of triethylamine and incubated for 1 h at 25° C. This cyclization reaction was quenched by addition of TFA to acidify the peptide suspensions. Then peptides were purified by reverse-phase HPLC (RP-HPLC) and molecular masses were verified by MALDI-TOF mass spectrometry, using a microflex or ultraflex instrument (Bruker Daltonics, Billerica, Mass.) (FIG. 5 and Table 2).

All peptides were chemically synthesized on a 25 μmole scale using a Syro Wave automated peptide synthesizer (Biotage) by Fmoc solid phase peptide chemical synthesis (SPPS). Firstly, NovaPEG Rink Amide resins were incubated with N,N-dimethylformamide (DMF) with rotation at ambient temperature for 30 min and washed 5 times with DMF. Coupling of each Fmoc-protected amino acid was performed on the engorged resin with a solution of 300 μL 0.5 M Fmoc-protected amino acid, 300 μL 0.5 M 2-(1H-Benzotriazole-1-yl)-1,1,3,3-tetramethyluronium hexafluorophosphate (HBTU) and 1-hydroxybenzotriazole (HOBt), and 150 μL 0.5 M N,N-diisopropylethylamine (DIPEA) in DMF and reacted for 1 hour at ambient temperature. After washing the resins with 1 mL DMF five times, Fmoc-deprotection was performed by incubating the resin with 600 μL 40% piperidine in DMF (vol/vol) and reacted for 30 min at ambient temperature. Each peptide was synthesized using the appropriately protected amino acid monomers corresponding to sequences in Tables 6 and 8 by repeating the Fmoc-protected amino acid coupling and Fmoc-deprotection steps accordingly. The N-terminal α-amino group of the synthesized peptides on the resin was chloroacetylated by incubating with a solution of 500 μL 0.5 M chloroacetyl N-hydroxysuccinimide (NHS) ester in N-methylpyrrolidone (NMP) with rotation for 60 min at ambient temperature. For the synthesis of Ce-L2 and Ce-L2d, the N-terminal α-amino group was acetylated by incubating with a solution of 500 μL 0.5 M acetic anhydride and 0.25 M DIPEA in NMP with rotation for 60 min at ambient temperature. After washing the resin with 5×1 mL DMF, peptides were fully deprotected and cleaved from resin by incubating with a solution of 2 mL trifluoroacetic acid (TFA), water, triisopropylsilane (TIS) and ethanedithiol (EDT) (92.5:2.5:2.5:2.5) with rotation for 3 hours at ambient temperature and precipitated with diethyl ether. The peptide pellet was dissolved in 10 mL DMSO/ 0.1% TFA in water (1:1), and the pH adjusted to >8 by addition of triethylamine (TEA), and incubated at ambient temperature for 1 h to enhance the cyclization via a thioether bond formation between N-terminal chloroacetamide group and cysteine sulfhydryl group. Peptide mass and cyclization was confirmed by MALDI-TOF MS analysis. The cyclization reaction was quenched by addition of TFA to acidify the peptide suspensions. Peptides were then purified by reverse-phase HPLC (Table 4), molecular masses were verified by MALDI-TOF MS analysis (Table 4), using a microflex or autoflex instrument (Bruker Daltonics). Ring junction confirmed by MSMS spectrum and fragment analysis (FIG. 5).

TABLE 2

LC-MS of representative peptide analogs chemically synthesized

| Peptide ID | Sequence* | Purity (%) | Retention time (min) | MALDI-TOF analysis (Calc./Obs.) |
|---|---|---|---|---|
| Ce-1 | \|⎯⎯s⎯⎯\|<br>$^{Ac-D}$YDYPGDHCYLYGTCG<br>(SEQ ID NO: 1) | >90 | 20.3 | 1764.65/1764.09 |
| Ce-2 | \|⎯⎯s⎯⎯\|<br>$^{Ac-D}$YDYPGDYCYLYGTCG<br>(SEQ ID NO: 2) | >90 | 21.9 | 1790.66/1790.10 |
| Ce-3 | \|⎯⎯⎯s⎯⎯⎯\|<br>$^{Ac-L}$YITLANPFRILHCG<br>(SEQ ID NO: 3) | >85 | 25.3 | 1655.86/1657.20 |
| Ce-4 | \|⎯⎯⎯s⎯⎯⎯\|<br>$^{Ac-L}$YTTLANPFRILHCG<br>(SEQ ID NO: 4) | >90 | 23.9 | 1643.82/1645.16 |

TABLE 2-continued

LC-MS of representative peptide analogs chemically synthesized

| Peptide ID | Sequence* | Purity (%) | Retention time (min) | MALDI-TOF analysis (Calc./Obs.) |
|---|---|---|---|---|
| Ce-2a | Ac-DYDYPGDYCYLYGTC (disulfide) (SEQ ID NO: 17) | >90 | 20.8 | 1734.62/1733.22 |
| Ce-2b | Ac-DYDYPGDYCYLYGT (disulfide) (SEQ ID NO: 18) | >95 | 21.4 | 1631.61/1630.15 |
| Ce-2c | Ac-DYDYPGDYCYLYG (disulfide) (SEQ ID NO: 19) | >95 | 21.5 | 1530.56/1529.05 |
| Ce-2d | Ac-DYDYPGDYCYLY (disulfide) (SEQ ID NO: 5) | >95 | 21.7 | 1472.56/1472.70 |
| Ce-2e | Ac-DYDYPGDYCYL (disulfide) (SEQ ID NO: 20) | >90 | 20.4 | 1310.48/1308.75 |
| Ce-2f | Ac-DYDYPGDYCY (disulfide) (SEQ ID NO: 21) | >90 | 19.0 | 1197.40/1195.72 |
| Ce-2g | Ac-DYDYPGDYC (disulfide) (SEQ ID NO: 22) | >90 | 20.9 | 1034.33/1032.62 |
| Ce-2S | Ac-DYDYPGDYCYLYGTSG (disulfide) (SEQ ID NO: 6) | >95 | 20.9 | 1774.68/1775.06 |
| Ce-L2 | Ac-DYDYPGDYSYLYGTCG (SEQ ID NO: 7) | >95 | 21.5 | 1776.70/1776.47 |
| Ce-L2d | Ac-DYDYPGDYSYLY (SEQ ID NO: 8) | >95 | 21.4 | 1458.60/1458.70 |
| Ce-2tail | Ac-DYLYGTCG (SEQ ID NO: 9) | >95 | 18.8 | 816.35/815.94 |
| Bm-1 | Ac-DYSWPNAPEIWKCCG (disulfide) (SEQ ID NO: 10) | >95 | 21.9 | 1692.71/1693.56 |
| Bm-2 | Ac-DYDLRTPWLKRHACG (disulfide) (SEQ ID NO: 11) | >90 | 21.8 | 1754.87/1755.95 |
| Bm-3 | Ac-DYQNRSIWLYGCCG (disulfide) (SEQ ID NO: 12) | >90 | 24.4 | 1601.68/1602.53 |
| Bm-4 | Ac-DYLEWPNCNTCG (disulfide) (SEQ ID NO: 13) | >90 | 22.1 | 1338.50/1339.27 |
| Bm-5 | Ac-DYLDWPNCSTCG (disulfide) (SEQ ID NO: 14) | >90 | 24.2 | 1297.47/1298.65 |
| Bm-6 | Ac-DYPEWPNCSTCG (disulfide) (SEQ ID NO: 15) | >90 | 21.9 | 1295.46/1296.39 |
| Bm-7 | Ac-DYAVWPNCRTCG (disulfide) (SEQ ID NO: 16) | >95 | 21.6 | 1308.54/1309.70 |

*Each peptide had a C-terminal amide

Macrocyclic Peptide Characterization Across PGM Orthologs:

Macrocyclic peptide solutions were prepared in DMSO at a concentration of 5 mM and titrated as an 11-point 1:3, or 16-point 1:2 series. For the 11-point titration series, compound dispense plates were prepared by NCATS compound management in 1536-well polypropylene deep well, v-bottom plates (Greiner Bio-One, #782270) in a single interweaved row-wise pattern per macrocyclic peptide resulting in a concentration range of 5 mM to 84.7 nM. For the 16-point titration series, compound dispense plate were prepared by hand down a single column per peptide of 384-well polypropylene deep well, v-bottom plates (Greiner Bio-One, #781270), and transferred to 1536-well polypropylene deep well, v-bottom plates with a multichannel pipette in duplicate for a concentration range of 5 mM to 152.6 nM. Each macrocyclic peptide was characterized across five iPGM orthologs, two dPGM isozymes, and the PK-FLuc control in the Kinase-Glo Plus coupled-enzyme assay described above. For the assay, 23 nL of the peptide titration series from either the 11-point or 16-point compound dispense plate were simultaneously transferred to 1536-well assay plates (Cat #789092-F, Greiner Bio-One North America) using a 1536-pin tool (Wako) for a final concentration range of 19.2 µM-0.33 nM or 19.2 µM-0.58 nM, respectively.

Curve Fitting:

All concentration response curves reporter were generated using GraphPad Prism 5 employing the sigmoidal dose-response (variable slope) curve fitting function:

$$Y = \text{Bottom} + \frac{(\text{Top} - \text{Bottom})}{1 + 10^{(LogEC50-X) + Hill\ Slope}}$$

Error Analysis:

The concentration of cyclic peptide or cyclic peptide analogs resulting in an inhibition of 50% of the indicated PGM activity tested are reported as $pIC_{50}$ values in Table 3. The number of independent experiments each peptide was tested in is indicated in the last column of Table 3 under 'N.' Inactive peptides were tested once. All experiments with reported standard deviation (SD) for error bars in FIG. 10B were conducted with two technical replicates and are representative plots from N≥3 independent experiments. The data used to construct FIG. 19A were from Table 3 converted from $pIC_{50}$ where $IC_{50}=10^{-pIC50}$. Error bars represent the SD values of the log normal distributed $IC_{50}$s determined for the given peptide, such that $IC_{50low}=10^{-(pIC50+SD)}$ and $IC_{50high}=10^{-(pIC50-SD)}$.

TABLE 3

Activity ($pIC_{50}$ and Max response) of macrocyclic peptides on PGM panel

| | IPGM Ortholog | | | | | | |
|---|---|---|---|---|---|---|---|
| | B. malayi iPGM | | | C. elegans iPGM | | | O. volvulus iPGM |
| Compound ID | Max Inhibition | pIC50, M | N | Max Inhibition | pIC50, M | N | Max Inhibition |
| Bm-1 | −82.8 ± 0.9 | 5.89 ± 0.27 | 2 | −60.5 ± 2.8 | 5.30 ± 0.08 | 2 | −82.1 ± 5.4 |
| Bm-2 | −0.1 ± 1.3 | NA | 2 | −7.9 ± 6.2 | NA | 2 | −15.2 ± 26.6 |
| Bm-3 | −86.4 ± 0.6 | 5.56 ± 0.29 | 2 | −66.1 ± 7.5 | 5.05 ± 0.14 | 2 | −89.2 ± 2.0 |
| Bm-4 | −86.3 ± 1.4 | 6.24 ± 0.41 | 2 | −75.5 ± 4.3 | 5.61 ± 0.29 | 2 | −85.7 ± 6.5 |
| Bm-5 | −84.7 ± 1.2 | 6.16 ± 0.36 | 2 | −73.9 ± 4.8 | 5.60 ± 0.29 | 2 | −83.1 ± 7.3 |
| Bm-6 | −86.8 ± 0.6 | 6.16 ± 0.30 | 2 | −76.4 ± 1.8 | 5.58 ± 0.25 | 2 | −86.0 ± 3.2 |
| Bm-7 | −74.0 ± 10.1 | 5.28 ± 0.39 | 2 | −78.0 ± 2.0 | 5.13 ± 0.18 | 2 | −78.0 ± 19.9 |
| Bm-4a | −88.0 ± 0.4 | 6.31 ± 0.29 | 2 | −79.0 ± 0.1 | 5.61 ± 0.23 | 2 | −87.8 ± 4.1 |
| Bm-4b | 3.1 ± 2.5 | NA | 2 | 2.1 ± 5.6 | NA | 2 | −4.1 ± 19.1 |
| Bm-4c | 4.2 ± 7.0 | NA | 2 | 2.1 ± 10.6 | NA | 2 | 8.7 ± 11.6 |
| Bm-4d | 11.2 | NA | 1 | 22.7 | NA | 1 | 16.9 |
| Bm-4e | −5.9 ± 4.1 | NA | 2 | −33.6 ± 33.8 | 2.50 ± 3.53 | 2 | −14.9 ± 30.9 |
| Ce-1 | −94 ± 3.4 | 7.92 ± 0.38 | 2 | −95.8 ± 3.5 | 8.40 ± 0.07 | 2 | −95.4 ± 2.6 |
| Ce-2 | −98.8 ± 3.9 | 8.27 ± 0.47 | 9 | −100.2 ± 6.6 | 8.65 ± 0.55 | 9 | −98.2 ± 3.4 |
| Ce-2* | −101.7 ± 1.0 | 9.02 ± 0.04 | 4 | −100.9 ± 2.4 | 9.60 ± 0.15 | 4 | −101.5 ± 3.4 |
| Ce-3 | −13.3 ± 2.0 | NA | 2 | −92.3 ± 0.4 | 6.33 ± 0.18 | 2 | −22.9 ± 30.8 |
| Ce-4 | −2.9 ± 3.3 | NA | 2 | −57.0 ± 17.1 | 5.22 ± 0.17 | 2 | −23.0 ± 35.7 |
| Ce-2a | −99.2 ± 5.3 | 8.07 ± 0.10 | 3 | −100.7 ± 6.9 | 8.39 ± 0.11 | 3 | −97.7 ± 4.4 |
| Ce-2a* | −100.3 ± 0.8 | 9.49 ± 0.08 | 4 | −99.6 ± 3.9 | 9.76 ± 0.05 | 4 | −97.5 ± 2.7 |
| Ce-2b | −91.8 ± 5.4 | 6.16 ± 0.14 | 2 | −97.9 ± 8.0 | 7.80 ± 0.20 | 2 | −80.1 ± 2.1 |
| Ce-2c | −88.2 | 5.93 ± 0.06 | 1 | −92.4 | 7.64 ± 0.03 | 1 | −78.4 |
| Ce-2d | −98.9 ± 4.6 | 7.17 ± 0.42 | 6 | −102.6 ± 6.6 | 8.56 ± 0.39 | 6 | −97.0 ± 5.4 |
| Ce-2d* | −100.2 ± 1.4 | 7.29 ± 0.04 | 4 | −100.4 ± 4.0 | 9.03 ± 0.06 | 4 | −99.1 ± 3.8 |
| Ce-2e | −82.7 ± 6.1 | 5.53 ± 0.23 | 2 | −97.2 ± 8.2 | 7.16 ± 0.26 | 2 | 55.5 ± 1.4 |
| Ce-2f | −14.8 | NA | 1 | −79.6 | 4.29 ± 0.13 | 1 | 4.3 |
| Ce-2g | 6.9 | NA | 1 | −18.7 | NA | 1 | 7.4 |
| Ce-L2 | −48.2 ± 18.2 | 4.89 ± 0.21 | 1 | −95.4 ± 8.7 | 5.94 ± 0.36 | 3 | −40.2 ± 27.6 |
| Ce-L2d | −7.3 ± 2.0 | NA | 3 | −20.9 ± 9.2 | NA | 3 | −15.7 ± 8.3 |
| Ce-2tail | −10.2 ± 3.3 | NA | 3 | −8.1 ± 13.9 | NA | 3 | −11.6 ± 5.3 |
| Ce-2S | −97.7 ± 0.6 | 6.28 ± 0.17 | 3 | −105 ± 4.7 | 8.08 ± 0.04 | 3 | −97.0 ± 1.6 |
| Ce-2S* | −77.1 ± 7.5 | 6.39 ±0.04 | 4 | −98.6 ± 4.9 | 7.92 ± 0.08 | 4 | −69.8 ± 9.3 |

TABLE 3-continued

Activity (pIC$_{50}$ and Max response) of macrocyclic peptides on PGM panel

| | IPGM Ortholog | | | | | |
|---|---|---|---|---|---|---|
| | O. volvulus iPGM | | D. immitis iPGM | | E. coli iPGM | |
| Compound ID | pIC50, M | N | Max Inhibition | pIC50, M | N | Max Inhibition | pIC50, M | N |

| Compound ID | pIC50, M | N | Max Inhibition | pIC50, M | N | Max Inhibition | pIC50, M | N |
|---|---|---|---|---|---|---|---|---|
| Bm-1 | 5.88 ± 0.53 | 2 | −85.9 ± 0.2 | 5.99 ± 0.41 | 2 | −60.6 ± 9.0 | 5.31 ± 0.06 | 2 |
| Bm-2 | NA | 2 | −10.5 ± 20.0 | NA | 2 | −12.3 ± 10.6 | NA | 2 |
| Bm-3 | 5.62 ± 0.45 | 2 | −89.4 ± 2.8 | 5.73 ± 0.47 | 2 | −60.0 ± 3.5 | 5.03 ± 0.04 | 2 |
| Bm-4 | 6.10 ± 0.63 | 2 | −88.1 ± 0.8 | 6.21 ± 0.44 | 2 | −76.3 ± 8.3 | 5.56 ± 0.16 | 2 |
| Bm-5 | 5.99 ± 0.69 | 2 | −87.1 ± 3.2 | 6.10 ± 0.56 | 2 | −74.3 ± 9.5 | 5.54 ± 0.20 | 2 |
| Bm-6 | 6.08 ± 0.53 | 2 | −90.2 ± 1.2 | 6.26 ± 0.43 | 2 | −77.4 ± 4.3 | 5.55 ± 0.07 | 2 |
| Bm-7 | 5.37 ± 0.52 | 2 | −83.1 ± 9.7 | 54.2 ± 0.46 | 2 | −69.7 ± 12.3 | 5.12 ± 0.09 | 2 |
| Bm-4a | 6.14 ± 0.62 | 2 | −90.5 ± 1.5 | 6.28 ± 0.40 | 2 | −78.3 ± 3.4 | 5.58 ± 0.19 | 2 |
| Bm-4b | NA | 2 | 3.9 ± 10.9 | NA | 2 | 13.6 ± 2.3 | NA | 2 |
| Bm-4c | NA | 2 | 6.5 ± 10.0 | NA | 2 | 6.5 ± 8.2 | NA | 2 |
| Bm-4d | NA | 1 | 0.7 | NA | 1 | −5.7 | NA | 1 |
| Bm-4e | NA | 2 | −21.4 ± 37.3 | 4.67 | 2 | −20.9 ± 4.5 | 5.2 | 2 |
| Ce-1 | 7.61 ± 0.65 | 2 | −95.0 ± 6.0 | 8.04 ± 0.41 | 2 | −96.5 ± 4.2 | 8.38 ± 0.10 | 2 |
| Ce-2 | 7.72 ± 0.69 | 9 | −101.1 ± 5.5 | 8.21 ± 0.60 | 9 | −101.7 ± 5.9 | 8.78 ± 0.43 | 9 |
| Ce-2* | 9.18 ± 0.08 | 4 | −98.9 ± 5.8 | 9.36 ± 0.11 | 4 | −105.7 ± 15.1 | 9.26 ± 0.04 | 4 |
| Ce-3 | 5.26 ± 0.18* | 2 | −30.1 ± 32.2 | 5.18 ± 0.03 | 2 | −91.4 ± 1.3 | 6.27 ± 0.10 | 2 |
| Ce-4 | 5.37 ± 0.14 | 2 | −22.1 ± 35.5 | 5.28 ± 0.06 | 2 | −44.3 ± 1.9 | 5.28 ± 0.02 | 2 |
| Ce-2a | 7.31 ± 0.09 | 3 | −100.1 ± 5.6 | 7.82 ± 0.29 | 3 | −99.2 ± 8.5 | 8.51 ± 0.14 | 3 |
| Ce-2a* | 9.68 ± 0.09 | 4 | −92.5 ± 4.0 | 9.68 ± 0.09 | 4 | −84.1 ± 9.5 | 9.58 ± 0.02 | 4 |
| Ce-2b | 5.61 ± 0.02 | 2 | −90.8 ± 4.9 | 5.96 ± 0.10 | 2 | −95.3 ± 9.0 | 7.98 ± 0.13 | 2 |
| Ce-2c | 5.41 ± 0.05 | 1 | −85.3 | 5.70 ± 0.05 | 1 | −89.1 | 7.98 ± 0.12 | 1 |
| Ce-2d | 6.72 ± 0.60 | 6 | −101.7 ± 6.0 | 7.04 ± 0.44 | 6 | −102.0 ± 6.9 | 8.71 ± 0.31 | 6 |
| Ce-2d* | 7.13 ± 0.05 | 4 | −94.0 ± 8.2 | 6.20 ± 1.13 | 4 | −99.4 ± 13.3 | 7.98 ± 0.27 | 4 |
| Ce-2e | 4.72 ± 0.26 | 2 | −76.4 ± 7.4 | 5.32 ± 0.05 | 2 | −94.5 ± 9.0 | 7.27 ± 0.16 | 2 |
| Ce-2f | NA | 1 | −3.9 | NA | 1 | −79.6 | 4.59 ± 0.10 | 1 |
| Ce-2g | NA | 1 | 7.4 | NA | 1 | −27.0 | NA | 1 |
| Ce-L2 | 5.18 | 3 | −44 ± 22.6 | 5.18 ± 0.17 | 1 | 95.1 ± 5.2 | 5.88 ± 0.39 | 3 |
| Ce-L2d | NA | 3 | −5.2 ± 4.9 | NA | 3 | −21.1 ± 2.4 | NA | 3 |
| Ce-2tail | NA | 3 | −1.9 ± 10.3 | NA | 3 | −21.1 ± 2.7 | NA | 3 |
| Ce-2S | 5.99 ± 0.28 | 3 | −98.5 ± 0.6 | 6.01 ± 0.28 | 3 | −104.6 ± 2.5 | 8.00 ± 0.10 | 3 |
| Ce-2S* | 6.35 ± 0.08 | 4 | −63.7 ± 11.4 | 6.24 ± 0.23 | 4 | −68.1 ± 8.9 | 7.98 ± 0.27 | 4 |

| | PGM Isozyme | | | | | | Control | | |
|---|---|---|---|---|---|---|---|---|---|
| | H. sapiens dPGM | | | E. coli dPGM | | | PK-Fluc | | |
| Compound ID | Max Inhibition | pIC50, M | N | Max Inhibition | pIC50, M | N | Max Inhibition | pIC50, M | N |
| Bm-1 | 3.0 ± 0.2 | NA | 2 | 7.8 ± 4.3 | NA | 2 | 10.4 ± 9.0 | NA | 2 |
| Bm-2 | −0.1 ± 1.3 | NA | 2 | −0.1 ± 1.3 | NA | 2 | −0.1 ± 1.3 | NA | 2 |
| Bm-3 | 5.1 ± 0.9 | NA | 2 | 8.4 ± 1.0 | NA | 2 | 7.9 ± 7.9 | NA | 2 |
| Bm-4 | 6.1 ± 2.2 | NA | 2 | 7.3 ± 3.1 | NA | 2 | 9.6 ± 6.4 | NA | 2 |
| Bm-5 | 5.5 ± 0.8 | NA | 2 | 3.8 ± 4.4 | NA | 2 | 7.3 ± 9.7 | NA | 2 |
| Bm-6 | 1.4 ± 3.8 | NA | 2 | 7.6 ± 1.1 | NA | 2 | 5.7 ± 2.8 | NA | 2 |
| Bm-7 | 7.1 ± 2.6 | NA | 2 | 9.3 ± 2.2 | NA | 2 | 2.7 ± 3.2 | NA | 2 |
| Bm-4a | 5.8 ± 0.4 | NA | 2 | 8.8 ± 0.7 | NA | 2 | 10.7 ± 2.2 | NA | 2 |
| Bm-4b | 6.1 ± 3.1 | NA | 2 | 9.8 ± 0.4 | NA | 2 | 9.9 ± 0.4 | NA | 2 |
| Bm-4c | 8.2 ± 0.2 | NA | 2 | 8.1 ± 4.6 | NA | 2 | 6.1 ± 10.0 | NA | 2 |
| Bm-4d | −1.1 | NA | 1.0 | −1.8 | NA | 1 | 4.4 | NA | 1 |
| Bm-4e | 3.2 ± 2.9 | NA | 2 | 8.1 ± 4.4 | NA | 2 | 11.5 ± 5.2 | NA | 2 |
| Ce-1 | 4.0 ± 1.1 | NA | 2 | 5.0 ± 10.4 | NA | 2 | 7.6 ± 17.6 | NA | 2 |
| Ce-2 | −0.3 ± 6.3 | NA | 9 | −5.9 ± 6.9 | NA | 9 | −1.4 ± 3.6 | NA | 9 |
| Ce-2* | 1.9 ± 2.7 | NA | 4 | 2.7 ± 0.7 | NA | 4 | NT | NT | 0 |
| Ce-3 | 1.6 ± 0.7 | NA | 2 | 9.1 ± 0.8 | NA | 2 | 9.5 ± 5.5 | NA | 2 |
| Ce-4 | 5.6 ± 3.5 | NA | 2 | 8.5 ± 3.3 | NA | 2 | 4.7 ± 3.7 | NA | 2 |
| Ce-2a | −1.6 ± 4.4 | NA | 3 | −0.9 ± 8.3 | NA | 3 | 4.8 ± 7.5 | NA | 3 |
| Ce-2a* | 20.8 ± 1.7 | NA | 4 | 9.0 ± 2.0 | NA | 4 | NT | NT | 0 |
| Ce-2b | 3.0 ± 3.9 | NA | 2 | 3.4 ± 8.1 | NA | 2 | 7.2 ± 12.8 | NA | 2 |
| Ce-2c | 9.6 | NA | 1 | 9.7 | NA | 1 | 13.4 | NA | 1 |
| Ce-2d | −1.2 ± 5.6 | NA | 6 | −6.3 ± 9.9 | NA | 6 | 0.0 ± 7.1 | NA | 6 |
| Ce-2d* | 7.9 ± 5.6 | NA | 4 | 2.3 ± 1.0 | NA | 4 | NT | NT | 0 |
| Ce-2e | 5.3 ± 3.5 | NA | 2 | 3.8 ± 5.9 | NA | 2 | 8.9 ± 11.2 | NA | 2 |
| Ce-2f | 7.5 | NA | 1 | 10.0 | NA | 1 | 18.1 | NA | 1 |
| Ce-2g | 7.4 | NA | 1 | 10.2 | NA | 1 | 15.8 | NA | 1 |
| Ce-L2 | −1.4 ± 6.9 | NA | 3 | −14.1 ± 1.3 | NA | 3 | −3.0 ± 1.2 | NA | 3 |
| Ce-L2d | −1.1 ± 8.5 | NA | 3 | −13.4 ± 3.2 | NA | 3 | −2.5 ± 2.3 | NA | 3 |

TABLE 3-continued

Activity (pIC$_{50}$ and Max response) of macrocyclic peptides on PGM panel

| Ce-2tail | −0.4 ± 7.4 | NA | 3 | −13.9 ± 3.8 | NA | 3 | −2.9 ± 3.4 | NA | 3 |
|---|---|---|---|---|---|---|---|---|---|
| Ce-2S | 1.6 ± 7.0 | NA | 3 | −12.1 ± 5.1 | NA | 3 | −1.4 ± 4.4 | NA | 3 |
| Ce-2S* | 30.5 ± 5.2 | NA | 4 | 12.4 ± 1.6 | NA | 4 | NT | NT | 0 |

Error was determined as follows: values for samples with N ≥ 2 experiments (≥4 replicates) represent s.d. For samples tested twice (N = 1) the standard error is determined from the nonlinear fit of the standard Hill equation to the aggregated data from the technical replicates (n = 2).
NA = no appreciable inhibition,
NT = not tested.
*Represent values obtained for iPGM concentrations of 500 pM to better estimate potency of the higher affinity ligands, Ce-2 and Ce-2a; lower affinity ligands, Ce-2d and Ce-S re-tested as well for comparison.

Exclusion Criteria:

A data point would be eliminated from the curve fit if the value was determined to be an outlier based on the criteria described in Southall et al. (*Handbook of Drug Screening*, pp. 442-464, 2009) Potential reasons for a data point to be eliminated from a curve fit would include, for example, known failure of compound transfer or under dispensing of assay reagent to the test well of the 1536-well assay plate. No data points needed to be excluded in the concentration response curves presented in this study.

Size Exclusion Chromatography:

Samples were analyzed and fractionated on a Superdex® 75 16/600 column using an AKTA® Pure chromatography system (GE Healthcare Bio-Sciences, Pittsburgh, Pa.). Samples, 500 μL, were eluted at 1 mL/min in buffer containing 30 mM Tris, 150 mM NaCl and 2 mM MgSO$_4$ at 4° C. Elution profile absorbance was recorded with in-line detection at 280 and 500 nm, and 2 mL fractions were collected in 96 deep-well plates.

Polyacrylamide Gel Electrophoresis:

Protein (10 μL/lane) was electrophoresed on Criterion™ TGX™ 12% precast polyacrylamide mini slab gels (Bio-Rad, Hercules, Calif.) in 1× Tris running buffer, ambient temperature at 200V for 45 mM Samples, 100 μL aliquots from size exclusion column fractions plus 33 μL 4× Laemmeli sample buffer (Bio-Rad 161-0747)±2% (WE, were heated for 10 min at 95° C. Gels were fixed for 30 mins in 50% methanol 10% acetic acid then stained with Coomassie Brilliant Blue G-250 colloidal protein stain (Sigma-Aldrich B8522) overnight and imaged on a Bio-Rad ChemiDoc™ imaging system or HP flatbed scanner Molecular weight ladder was Bio-Rad catalog number 161-0376.

Phylogenetic Tree Construction:

The protein sequences for the seven PGM orthologs were aligned using Clustal Omega multiple sequence alignment analysis (available on the World Wide Web at ebi.ac.uk/Tools/msa/clustalo/). The accession numbers for the sequence alignment are NP_871851.1 (*Caenorhabditis elegans*), AAQ97626.1 (*Brugia malayi*), AAV33247.1 (*Onchocerca volvulus*), AEA91534.1 (*Dirofilaria immitis*), NP_002620.1 (*Homo sapiens*), P37689.1 (*Escherichia coli* 2, 3-bisphosphoglycerate-independent phosphoglycerate mutase), and P62707.2 (*Escherichia coli* 2, 3-bisphosphoglycerate-dependent phosphoglycerate mutase), all of which are incorporated herein by reference as present in GenBank on Aug. 11, 2016. The Pearson/FASTA alignment was uploaded to RAxML BlackBox (available on the World Wide Web at genome.jp/tools/raxml) for tree construction. Gamma model of rate of heterogeneity and the BLOSUM62 protein substitution matrix with a maximum likelihood search were applied for tree building. No outgroup was selected for tree rooting. A rapid algorithm bootstrapping analysis was performed with 1,000 replicates.

Crystallization and Data Collection:

Purified full length apo iPGM from *Caenorhabditis elegans* spanning and harboring a C-terminal hexahistidine tag was concentrated to 11.6 mg/mL in 200 mM NaCl, 20 mM Tris pH 7.5, 2 mM TCEP. Another sample of iPGM from *Caenorhabditis elegans* spanning residues M19 to 1539, for preparation of the peptide complex, was concentrated to 10.8 mg/mL in 150 mM NaCl, 30 mM Tris pH 8.0 for crystallization screening. To prepare the Ce-2d cyclic peptide complex a 50 mM stock solution of peptide Ce-2d was prepared in DMSO, mixed in a 1:1.5 (protein:cyclic peptide) molar ratio and incubated on ice for 30 minutes prior to screening. All crystallization experiments were conducted with Compact 300 (Rigaku Reagents) sitting drop vapor diffusion plates at 20° C. using equal volumes of protein and crystallization solution equilibrated against 75 μL of the latter.

Figure 6A:
FIGS. 6A-6D are a series of panels showing crystals of apo *C. elegans* iPGM and in a complex with Ce-2d.
Figure 6C:
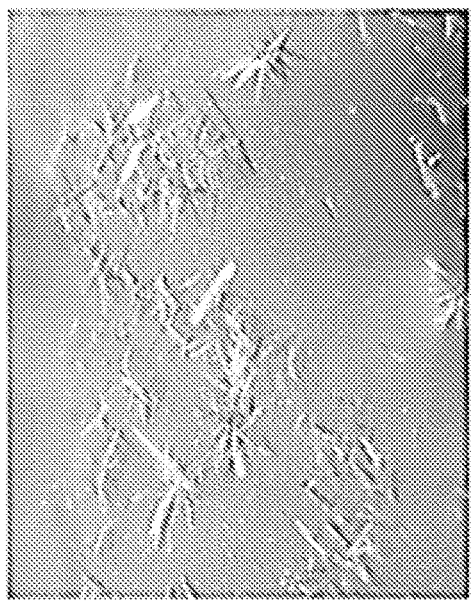
Figure 6B:
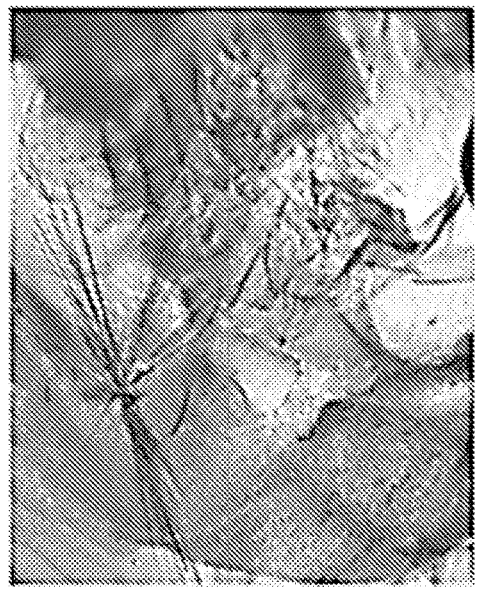

Apo iPGM:

Native *C. elegans* iPGM yielded crystals that formed plate clusters which represented two crystal forms. Monoclinic P crystals (*C. elegans* iPGM-m) were obtained in approximately 4 weeks (FIG. 6A) from the Wizard 3-4 screen (Rigaku Reagents) condition D11 (30% (w/v) PEG 5000 MME, 100 mM MES pH 6.5, 200 mM ammonium sulfate). The sample was subjected to refinement screening using the Additive Screen HT (Hampton Research). After approximately two weeks, single plate shape crystals (FIG. 6B) were observed from a condition consisting of 30% (w/v) PEG 5000 MME, 100 mM MES pH 6.5, 200 mM ammonium sulfate, 100 mM guanidine-HCl. A second crystal form belonging to an orthorhombic P lattice (*C. elegans* iPGM-o) was observed after 6 months (FIG. 6C) from the Index HT (Hampton Research) condition F7 (25% (w/v) PEG 3350, 100 mM Bis-Tris pH 6.5, 200 mM ammonium sulfate). Samples were transferred to a fresh drop composed of 75% crystallization solution and 25% PEG 400 and stored in liquid nitrogen.

iPGM•Ce-2d Complex:

*C. elegans* Met19 iPGM prepared in a 1:1.5 ratio with Ce-2d yielded crystals displaying a needle morphology after 7 days (FIG. 6D) from the Crystal Screen HT (Hampton Research) condition A6 (30% (w/v) PEG 4000, 100 mM Tris pH 8.5, 200 mM MgCl$_2$. Samples were transferred to a fresh drop composed of 80% crystallization solution and 20% glycerol and stored in liquid nitrogen.

Structure Solution and Refinement:

X-ray diffraction data were collected at the Advanced Photon Source beamline 17-ID using a Dectris Pilatus 6M pixel array detector. Intensities were integrated using XDS (Kabsch *J. Appl. Crystallogr.* 21:67-71, 1988; Kabsch, *Acta Crystallogr.* D 66:125-132, 2010) via Autoproc (Vonrhein et al., *Acta Crystallogr.* D 67:293-302, 2011) and the Laue class analysis and data scaling were performed with Aimless19 which suggested that the highest probability Laue class was 2 lm for iPGM-m and mmm for iPGM-o. The Matthew's coefficient (Matthews et al., *J. Mol. Biol.* 33:491, 1968) indicated that there were two molecules in the asymmetric unit ($V_m$=2.7 Å$^3$/Da, % solvent=54%) and ($V_m$=2.5 Å$^3$/Da, % solvent=50%) for *C. elegans* iPGM-m and mmm iPGM-o respectively. Structure solution for iPGM-m was conducted by molecular replacement with Balbes (Long et al., *Acta Crystallogr. D* 64:125-132, 2008) which generated a search model using a previously determined iPGM structure (PDB: 1O98; Rigden et al., *J. Mol. Biol.* 328:909-920, 2003). Searches were conducted in space groups P2 and P2$_1$ and the top solution was obtained in the latter space group which was used from this point forward. Initial refinement of the model with Refmac (Murshudov et al., *Acta Crystallogr. D* 53:240-255, 1997) converged at R/R$_{free}$ of 34%/37%. For iPGM-o, molecular replacement was conducted using Phaser (Mccoy et al., *J. Appl. Crystallogr.* 40:658-674, 2007) in all possible space groups with 222 point symmetry using PDB 2IFY (Nukui et al., *Biophys. J.* 92:977-988, 2007) as the search model. The top solution was obtained in the space group P2$_1$2$_1$2$_1$. The models were improved by automated model building with Phenix (Adams et al., *Acta Crystallogr. D* 66:213-221, 2010).

Structure solution for iPGM•Ce-2d was conducted by molecular replacement using a single subunit of iPGM-o as the search model. Searches were conducted in space groups P2 and P2$_1$ ($V_m$=2.3 Å$^3$/Da, % solvent=47%) for two molecules in the asymmetric unit and the top solution was obtained in P2 which was used from this point forward. Initial refinement of the model was carried out with Refmac (Murshudov et al., *Acta Crystallogr. D* 53:240-255, 1997) and was improved by automated model building with Apr/warp (Langer et al., *Nat. Protoc.* 3:1171-1179, 2008). Subsequent refinement and manual model building were carried out with Phenix and Coot (Emsley et al., *Acta Crystallogr. D* 66:486-501, 2010), respectively. Disordered side chains were truncated to the point for which electron density could be observed. Structure validation was conducted with Molprobity (Chen et al., *Acta Crystallogr. D* 66:12-21, 2010) and figures were prepared using the CCP4MG package (Potterton et al., *Acta Crystallogr. D* 60:2288-2294, 2004). Superposition of iPGM structures was conducted using GESAMT (Krissinel et al., *J. Mol. Biochem.* 1:76-85, 2012) via the CCP4 (Winn et al., *Acta Crystallogr. D* 67:235-242, 2011) interface. Relevant crystallographic data are provided in Table 4.

TABLE 4

X-ray data collection and refinement statistics

|  | *C. elegans* iPGM-m | *C. elegans* iPGM-o | *C. elegans* iPGM•Ce-2d |
|---|---|---|---|
| Data Collection | | | |
| Unit-cell parameters (Å, °) | a = 67.85, b = 94.38, c = 102.2, β = 96.6 | a = 70.32, b = 98.85, c = 173.10 | a = 73.78, b = 75.83, c = 101.42, β = 95.7 |
| Space group | P2$_1$ | P2$_1$2$_1$2$_1$ | P2 |
| Resolution (Å)$^a$ | 46.48-2.95 (3.13-2.95) | 98.85-2.45 (2.54-2.45) | 48.17-1.95 (1.99-1.95) |
| Wavelength (Å) | 1.0000 | 1.0000 | 1.0000 |
| Temperature (K) | 100 | 100 | 100 |
| Observed reflections | 90,718 | 217,179 | 275,647 |
| Unique reflections | 27,020 | 43,707 | 80,429 |
| <I/σ(I)>$^a$ | 9.0 (2.3) | 7.6 (1.9) | 7.8 (2.2) |
| Completeness (%)$^a$ | 99.7 (99.9) | 97.5 (99.4) | 99.0 (98.1) |
| Multiplicity$^a$ | 3.4 (3.5) | 5.0 (4.7) | 3.4 (3.4) |
| R$_{merge}$ (%)$^{a,b}$ | 14.1 (62.5) | 20.5 (84.0) | 14.6 (60.3) |
| R$_{meas}$ (%)$^{a,d}$ | 16.8 (74.0) | 22.9 (92.6) | 17.4 (71.8) |
| R$_{pim}$ (%)$^{a,d}$ | 9.0 (39.4) | 9.9 (41.7) | 9.2 (38.5) |
| CC$_{1/2}$$^{a,e}$ | 0.985 (0.779) | 0.976 (0.601) | 0.988 (0.811) |
| Refinement | | | |
| Resolution (Å)$^a$ | 42.98-2.95 | 40.44-2.45 | 35.49-1.95 |
| Reflections (working/test)$^a$ | 25,639/1,353 | 41,536/2,137 | 76,298/4,113 |
| R$_{factor}$/R$_{free}$ (%)$^{a,c}$ | 18.4/23.7 | 18.5/26.0 | 15.3/20.3 |
| No. of atoms (Protein/Peptide/Mn$^{2+}$/Zn$^{2+}$/water) | 7,837/0/2/2/0 | 7,886/0/2/2/234 | 8,001/210/2/2/735 |
| Model Quality | | | |
| R.m.s deviations | | | |
| Bond lengths (Å) | 0.008 | 0.009 | 0.018 |
| Bond angles (°) | 1.013 | 0.936 | 1.029 |
| Average B-factor (Å$^2$) | | | |
| All Atoms | 48.6 | 25.2 | 19.3 |
| Protein | 48.7 | 25.2 | 18.8 |
| Peptide | — | — | 18.2 |
| Mn$^{2+}$/Zn$^{2+}$ | 49.2/48.3 | 38.4/27.0 | 17.5/17.6 |
| Water | — | 20.9 | 26 |

TABLE 4-continued

X-ray data collection and refinement statistics

|  | C. elegans iPGM-m | C. elegans iPGM-o | C. elegans iPGM•Ce-2d |
|---|---|---|---|
| Coordinate error(maximum likelihood) (Å) | 0.35 | 0.35 | 0.2 |
| Ramachandran Plot |  |  |  |
| Most favored (%) | 97.6 | 96.6 | 98 |
| Additionally allowed (%) | 1.8 | 3.1 | 1.7 |

[a]Values in parenthesis are for the highest resolution shell.
[b]$R_{merge} = \Sigma_{hkl}\Sigma_i | I(hkl) - <I(hkl)>|/\Sigma_{hkl}\Sigma_i(hkl)$, where I(hkl) is the intensity measured for the ith reflection and <I(hkl)> is the average intensity of all reflections with indices hkl.
[c]$R_{factor} = \Sigma_{hkl} || F_{obs}(hkl) | - | F_{calc}(hkl) ||/\Sigma_{hkl} | F_{obs}(hkl)|$; Rfree is calculated in an identical manner using 5% of randomly selected reflections that were not included in the refinement.
[d]$R_{meas}$ = redundancy-independent (multiplicity-weighted) $R_{merge}$. $R_{pim}$ = precision-indicating (multiplicity-weighted) $R_{merge}$.
[e]$CC_{1/2}$ is the correlation coefficient of the mean intensities between two random half-sets of data.

Figure 7A:
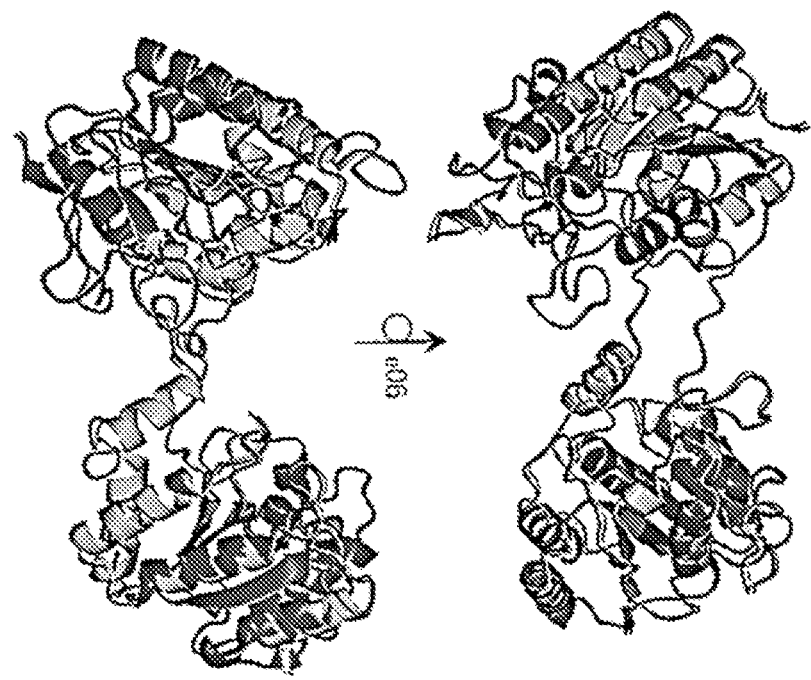
FIGS. 7A-7C are a series of ribbon diagrams of asymmetric unit cell of *C. elegans* iPGM-m.
Figure 7B:
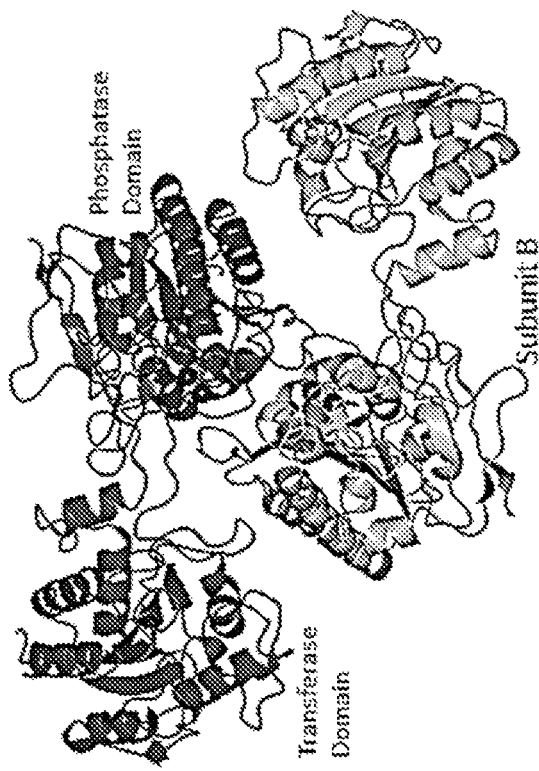

Crystallographic Analysis:

The final model of iPGM-m consisted of two subunits with two $Mn^{2+}$ and $Zn^{2+}$ ions modeled within domain A of each subunit (FIG. 7A) and the first 20 residues of the N-terminus and last 13 residues of the C-terminus were disordered and could not be modeled. The two subunits are nearly identical with an RMSD deviation of 0.58 Å between Cα atoms for 517 residues aligned using GESAMT (Krissinel et al., *J. Mol. Biochem.* 1:76-85, 2012) (FIG. 7B). Crystals of the orthorhombic form (*C. elegans* iPGM-o) were obtained after approximately 6 months and diffracted to higher resolution than iPGM-m. Similarly, the N and C-terminal residues were disordered in the iPGM-o as well. The subunits of iPGM-o were structurally very similar with an RMSD deviation of 0.77 Å between Cα atoms for 520 residues aligned. In addition, the structures of iPGM-o and iPGM-m were quite similar with an RMSD deviation of 1.85 Å between Cα atoms for 495 residues aligned. However, the phosphatase domains are much more closely aligned whereas the transferase domains exhibit a slight shift (FIG. 8C) which may be due to the conformational flexibility of this domain. The structure of iPGM-o also contains two metal ions in the substrate binding site which bind in a similar manner to iPGM-m (see below).

Figure 8A:
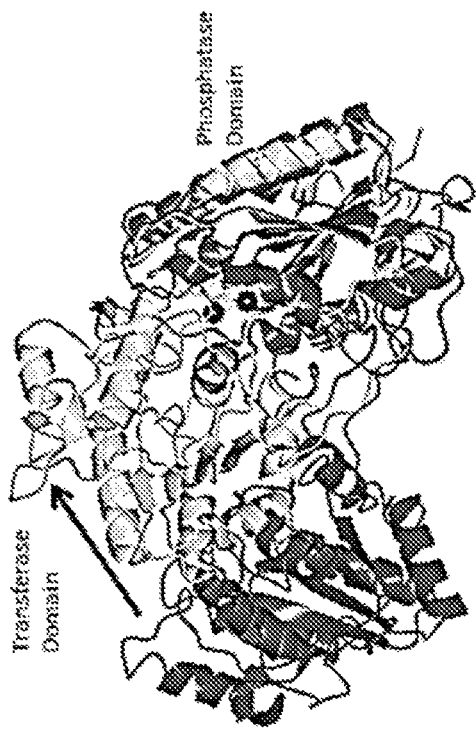
FIGS. 8A-8C are a series of ribbon diagrams showing a comparison of *C. elegans* iPGM to *Bacillus anthracis* and *Bacillus stearothermophilus* iPGM.
Figure 8B:
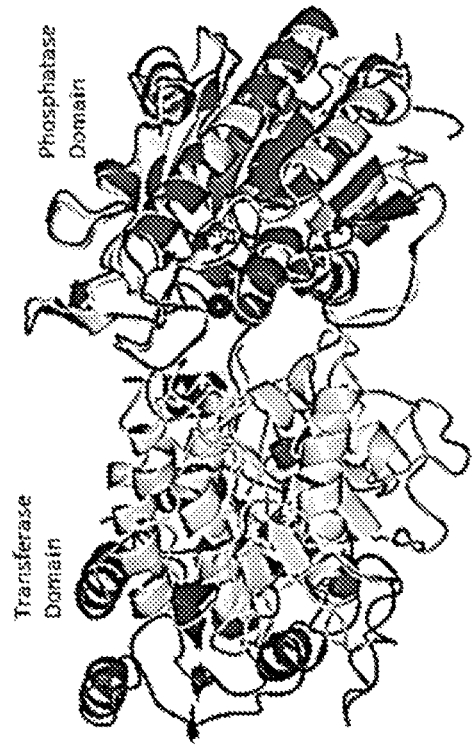
Figure 8C:
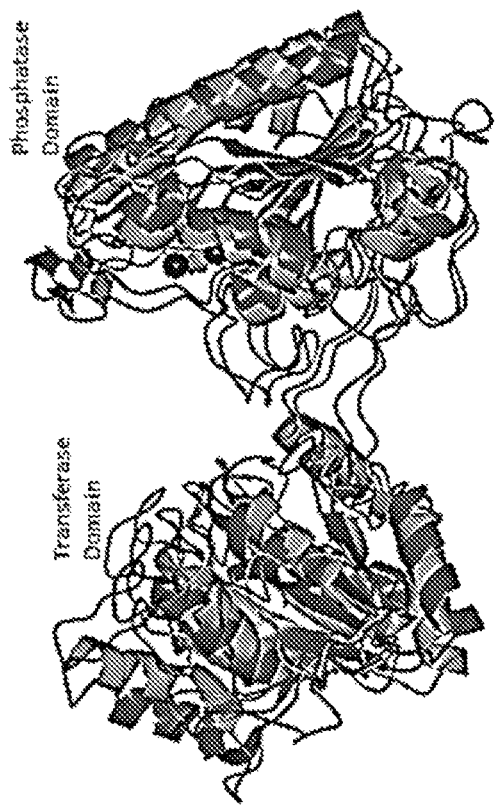

Comparison of *C. elegans* iPGM-m to Other Apo iPGM Structures:

Superposition of *C. elegans* iPGM-m with iPGM from *Bacillus anthracis* (PDB: 2IFY) yielded an RMSD of 2.76 Å between Cα atoms (476 residues aligned). Although the deviation from superposition was somewhat large between the two structures, the overall fold was very similar between the two structures (FIGS. 8A-8C). The structure of *C. elegans* iPGM-m was also compared with that of a substrate bound iPGM from *Bacillus stearothermophilus* (PDB: 1O98). Superposition yielded an RMSD of 1.07 Å between Cα atoms. However, only 282 residues could be aligned for residues in the transferase domain since substrate binding produced a large conformational change in the phosphatase domain (FIG. 8B).

Figure 9A:
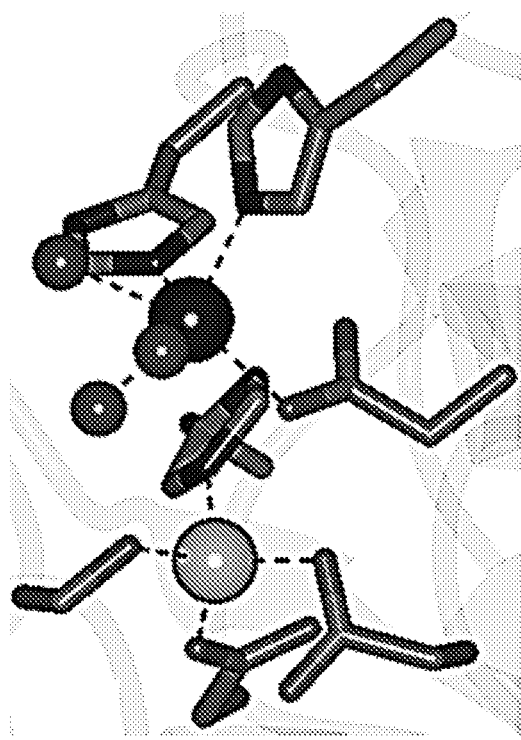
FIGS. 9A-9C are a series of diagrams showing metal ion binding sites in iPGM.
Figure 9B:
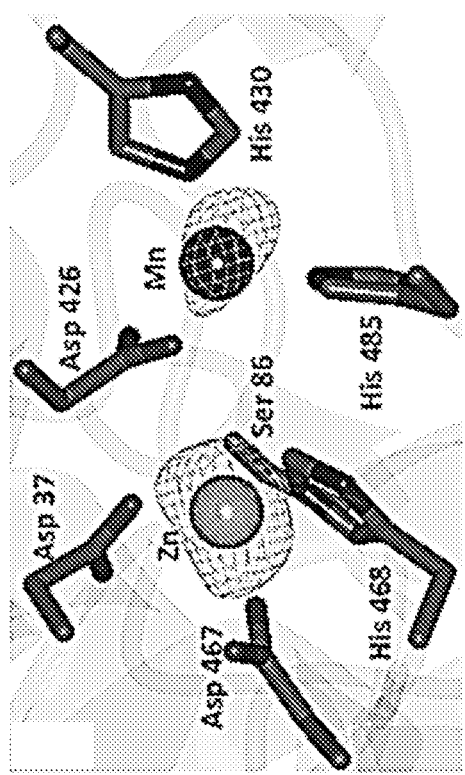
Figure 9C:
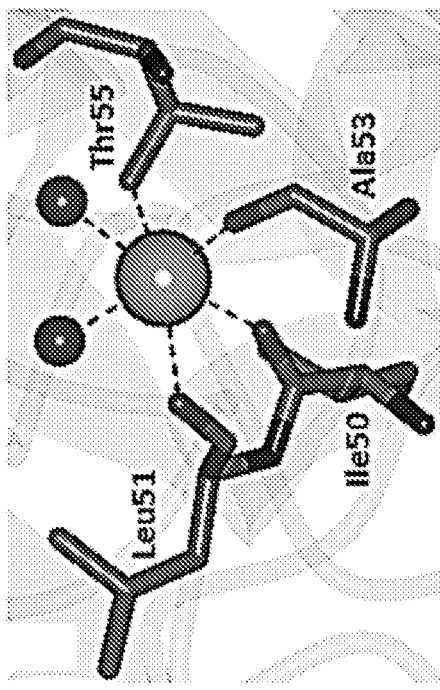

Metal Ion Sites:

Large peaks of positive electron density (Fo-Fc) were observed in the metal binding sites of the phosphatase domain following refinement FIG. 9A. This region is occupied by Asp 426 and His 430 (site 1) and Asp 37, Ser 86, Asp 467 and His 468 (site 2). When these sites were refined as $Mg^{2+}$ ions, residual positive electron density was observed suggesting that a larger metal ion was present. Modelling $Mn^{2+}$ ions at each site resulted in a B-factor of approximately 17 $Å^2$ at site 1, but site 2 contained some positive electron density and a B-factor of approximately 7 $Å^2$. Additionally, the coordinating distances between the surrounding residues and the ion at site 2 were approximately 1.9 Å to 2.0 Å which are shorter than expected for a $Mn^{2+}$ ion (2.1 Å to 2.2 Å). Phased anomalous difference maps were calculated, using data collected at a wavelength of 1.0000 Å, which yielded peak heights of: site 1 (5.7σ) and site 2 (11.7σ) as shown in FIG. 9A. $Zn^{2+}$ ions may occupy site 2 based on the coordinating distances and anomalous signal, and homology of the iPGM phosphatase domain to that of *E. coli* alkaline phosphatase (Jedrzejas *Prog. Biophys. Mol. Biol.* 73:263-287, 2000). The theoretical anomalous signal at a wavelength of 1.0000 Å, is 2.6 $e^-$ and 1.4 $e^-$ for $Zn^{2+}$ and $Mn^{2+}$ ions, respectively. Additionally, data were collected at a wavelength of 1.9016 Å which is on the low energy side of the $Mn^{2+}$ absorption edge. The theoretical anomalous signal at this wavelength is 1.1 $e^-$ and 0.49 $e^-$ for $Zn^{2+}$ and $Mn^{2+}$ ions respectively. A phased anomalous difference map was calculated using the 1.9016 Å data and produced no peaks at site 1 whereas peaks of approximately 5σ were observed at site 2. Subsequent refinement of $Mn^{2+}$ and $Zn^{2+}$ ions at site1 and site2, respectively yielded no residual positive electron density which further supported the assignments for these sites. The coordination of these metals by *C. elegans* iPGM is shown in FIG. 9B and the distances are listed in Table 5. It should be noted that an $Mg^{2+}$ binding site, from the crystallization solution, was also observed as shown in FIG. 9C.

TABLE 5

H-bonding and metal coordination distances in the *C. elegans* iPGM•Ce-2d structure

| Ce-2d Residue or metal ion | iPGM Residue | Distance Min Residue Pair | Closest Atom Filter < 5Å | Ce-2d Residue or metal ion | iPGM Residue | Distance Min Residue Pair | Closest Atom Filter < 5Å |
|---|---|---|---|---|---|---|---|
| D-TYR 1 | ASN336 | 3.802 | O D-TYR1/O ASN336 | TYR 7 | ARG284 | 2.4231 | CD1 TYR7/NH2 ARG284 |
| D-TYR 1 | PHE365 | 3.1853 | O D-TYR1/CZ PHE365 | TYR 7 | ASP286 | 2.5816 | CE2 TYR7/OD2 ASP286 |
| D-TYR 1 | GLY369 | 3.2692 | O D-TYR1/O GLY369 | TYR 9 | VAL 88 | 2.1049 | O TYR9/CG2 VAL88 |
| D-TYR 1 | GLY370 | 2.4339 | O D-TYR1/O GLY370 | TYR 9 | ILE 99 | 2.9585 | CG TYR9/CB ILE99 |
| D-TYR 1 | PHE366 | 2.7405 | CE1 D-TYR1/CE1 PHE366 | TYR 9 | LEU 91 | 2.0412 | CE1 TYR9/CD2 LEU91 |

TABLE 5-continued

H-bonding and metal coordination distances in the C. elegans iPGM•Ce-2d structure

| Ce-2d Residue or metal ion | iPGM Residue | Distance Min Residue Pair | Closest Atom Filter < 5Å | Ce-2d Residue or metal ion | iPGM Residue | Distance Min Residue Pair | Closest Atom Filter < 5Å |
|---|---|---|---|---|---|---|---|
| D-TYR 1 | GLU 87 | 2.4137 | OH D-TYR1/CB GLU87 | TYR 9 | ASN336 | 2.9207 | OH TYR9/ND2 ASN336 |
| D-TYR 1 | LEU 91 | 3.7614 | OH D-TYR1/CA LEU91 | TYR 9 | GLY369 | 3.6132 | OH TYR9/C GLY369 |
| ASP 2 | ARG289 | 2.6574 | OD2 ASP2/NH2 ARG289 | TYR 9 | GLY370 | 3.3093 | OH TYR9/CA GLY370 |
| TYR 3 | ALA334 | 2.4222 | CD1 TYR3/N ALA334 | LEU 10 | ILE 99 | 3.3204 | N LEU10/O ILE99 |
| TYR 3 | ARG289 | 4.541 | CD2 TYR3/NE ARG289 | LEU 10 | LEU 78 | 2.2841 | CA LEU10/CD2 LEU78 |
| TYR 3 | PRO333 | 2.4141 | CD2 TYR3/CB PRO333 | LEU 10 | LEU 82 | 3.2601 | O LEU10/CD2 LEU82 |
| TYR 3 | GLN320 | 3.3003 | CE2 TYR3/O GLN320 | LEU 10 | TYR100 | 3.7162 | CD1 LEU10/CD1 TYR100 |
| TYR 3 | ASP102 | 2.5979 | OH TYR3/OD2 ASP102 | LEU 10 | GLN101 | 2.5471 | CD1 LEU10/OE1 GLN101 |
| TYR 3 | TYR283 | 3.0582 | OH TYR3/O TYR283 | LEU 10 | ILE103 | 4.0535 | CD1 LEU10/CD1 ILE103 |
| TYR 3 | ARG284 | 3.2451 | OH TYR3/C ARG284 | LEU 10 | PRO 79 | 2.948 | CD2 LEU10/CD PRO79 |
| TYR 3 | ALA285 | 2.6402 | OH TYR3/N ALA285 | TYR 11 | VAL 88 | 2.6738 | C TYR11/CB VAL88 |
| TYR 3 | ASP286 | 3.1893 | OH TYR3/N ASP285 | TYR 11 | ASN 85 | 1.8956 | O TYR11/CG ASN85 |
| TYR 3 | THR319 | 3.1545 | OH TYR3/CB THR319 | TYR 11 | HIS485 | 4.5843 | O TYR11/CE1 HIS485 |
| PRO 4 | ALA334 | 2.3729 | O PRO4/CB ALA334 | TYR 11 | GLU87 | 3.02 | OXT TYR11/OE1 GLU87 |
| PRO 4 | ASN336 | 2.6715 | CG PRO4/CB ASN336 | Mn2+ | Asp426 | 2.14 | Asp426/OD2 |
| GLY 5 | ILE99 | 2.4236 | N GLY5/CG2 ILE99 | Mn2+ | His430 | 2.21 | His430/NE2 |
| GLY 5 | TYR100 | 2.5803 | O GLY5/O TYR 10D | Mn2+ | His485 | 2.13 | His485/NE2 |
| GLY 5 | GLN101 | 3.2351 | O GLY5/CA GLN101 | Mn2+ | H20 | 2.09, 245, 2.39 | H20 |
| GLY 5 | ASP102 | 2.8573 | O GLY5/N ASP102 | Zn2+ | Asp37 | 1.95 | OD1 Asp37 |
| TYR 7 | GLN101 | 2.7272 | CA TYR7/NE2 GLN101 | Zn2+ | Ser86 | 1.99 | OGSer86 |
| TYR 7 | ILE99 | 3.5024 | O TYR7/C ILE99 | Zn2+ | His468 | 2 | NE2 His468 |
|  |  |  |  | Zn2+ | Asp467 | 1.91 | OD2 Asp467 |

Database Deposition:

Coordinates and structure factors have been deposited to the Worldwide Protein Databank with the following accession codes: C. elegans apo iPGM-m (PDB 5KGM), C. elegans apo iPGM-o (PDB 5KGL) and the complex C. elegans Met19 iPGM•Ce-2d (PDB 5KGN), all of which are incorporated herein by reference.

Example 2

Identification of High Affinity iPGM Ligands

A recently reported attempt to obtain small molecule inhibitors against iPGM from a combined library of 380,000 compounds by Genzyme Corporation and the National Center for Drug Screening in Shanghai resulted in only two low potency compounds, apparent metal ion chelators (Crowther et al., PLoS Neglected Trop. Dis. 8:e2628, 2014). Given the apparent refractory nature of iPGM toward small molecule inhibition outside of metal ion ligands, and the difficulty of identifying chemotypes of the alkaline phosphatase superfamily enzyme class from HTS with sub-micromolar optimization potential (Narisawa et al., J. Bone Miner. Res. 22:1700-1710, 2007), we approached the problem through the complementary method of affinity selection using an in-vitro display system, referred to as RaPID (Random non-standard Peptides Integrated Discovery).

The RaPID system enabled us to exploit the diversity of macrocyclic peptide populations numbering in a trillion unique members and enrich for and amplify low abundance, high affinity ligands (Bashiruddin et al., Curr. Opin. Chem. Biol. 24:131-138, 2015). For this particular selection campaign, we utilized a thioether-cyclic peptide library initiated with either L- or D-tyrosine (L/D-Tyr) and performed selection of high affinity ligands against two protein targets, B. malayi iPGM and C. elegans iPGM, which were individually immobilized on magnetic beads via the His6 tag at the C-terminus of these recombinant enzymes. The sequence alignments (FIGS. 4A-4C) from 69 RaPID-derived clones resulted in 11 independent sequence families, corresponding to macrocyclic peptides of a lariat structure with ring sizes ranging between 7-13 amino acids and C-terminal tails of 1-7 amino acids (Table 6).

It should be noted that the cyclic peptides as isolated by RaPID are tethered at their carboxyl terminus via puromycin to the encoding mRNA. Any effect of the tethered nucleic acid during cyclic peptide binding to their target, either to facilitate binding or block possible productive target-cyclic peptide interactions is an inherent property of mRNA-display technology. Significant binding contributions made via the nucleic acid will not be present in samples made by the solid-phase peptide synthesis step.

TABLE 6

Inhibitory activity of RaPID selected macrocyclic peptides

| | | | pIC$_{50}$ | | | | | |
|---|---|---|---|---|---|---|---|---|
| Protein ID* | Sequence | Ring size/ tail length | C. elegans iPGM | B. malayi iPGM | O. volvulus iPGM | D. immitis iPGM | E. coli iPGM | H. sapiens dPGM | E. coli dPGM |
| Bm-1 | Ac-DYSWPNAPEIWKCCG |—S—| (SEQ ID NO: 10) | 12/2 | 5.30 | 5.89 | 5.88 | 5.99 | 5.31 | NA | NA |

TABLE 6-continued

Inhibitory activity of RaPID selected macrocyclic peptides

| Protein ID* | Sequence | Ring size/ tail length | C. elegans iPGM | B. malayi iPGM | O. volvulus iPGM | D. immitis iPGM | E. coli iPGM | H. sapiens dPGM | E. coli dPGM |
|---|---|---|---|---|---|---|---|---|---|
| Bm-2 | \|———s———\|<br>Ac-D YDLRTPWLKRHACG<br>(SEQ ID NO: 11) | 13/1 | NA | NA | NA | NA | NA | NA | NA |
| Bm-3 | \|———s———\|<br>Ac-D YQNRSIWLYGCCG<br>(SEQ ID NO: 12) | 12/2 | 5.05 | 5.56 | 5.62 | 5.73 | 5.03 | NA | NA |
| Bm-4 | \|—s—\|<br>Ac-D YLEWPNCNTCG<br>(SEQ ID NO: 13) | 7/4 | 5.61 | 6.24 | 6.10 | 6.21 | 5.56 | NA | NA |
| Bm-5 | \|—s—\|<br>Ac-D YLDWPNCSTCG<br>(SEQ ID NO: 14) | 7/4 | 5.60 | 6.16 | 5.99 | 6.10 | 5.54 | NA | NA |
| Bm-6 | \|—s—\|<br>Ac-D YPEWPNCSTCG<br>(SEQ ID NO: 15) | 7/4 | 5.58 | 6.16 | 6.08 | 6.26 | 5.55 | NA | NA |
| Bm-7 | \|—s—\|<br>Ac-D YAVWPNCRTCG<br>(SEQ ID NO: 16) | 7/4 | 5.13 | 5.28 | 5.37 | 5.42 | 5.12 | NA | NA |
| Ce-1 | \|—s—\|<br>Ac-D YDYPGDHCYLYGTCG<br>(SEQ ID NO: 1) | 8/7 | 8.40 | 7.92 | 7.62 | 8.04 | 8.38 | NA | NA |
| Ce-2 | \|—s—\|<br>Ac-D YDYPGDYCYLYGTCG<br>(SEQ ID NO: 2) | 8/7 | 8.65 | 8.27 | 7.72 | 8.21 | 8.78 | NA | NA |
| Ce-3 | \|———s———\|<br>Ac-L YITLANPFRILHCG<br>(SEQ ID NO: 3) | 13/1 | 6.33 | NA | NA | NA | 6.27 | NA | NA |
| Ce-4 | \|———s———\|<br>Ac-L YTTLANPFRILHCG<br>(SEQ ID NO: 4) | 13/1 | 5.22 | NA | NA | NA | 5.28 | NA | NA |

Each peptide had a C-terminal amide. Peptide sequences identified from the pool in round 6 and 7 for B. malayi and C. elegans iPGM, respectively.
$pIC_{50} = -\log IC_{50}$.
NA = No appreciable inhibitory activity at highest concentration tested.
*Ce-1 is ipglycermide A and Ce-2 is ipglycermide B.

Example 3

Functional Evaluation of Cyclic Peptide PGM Inhibitors

To efficiently profile the activity of the cyclic peptides derived from in vitro selection, several phosphoglycerate mutase enzymes from a range of species were evaluated, including the parasite target, B. malayi iPGM and filarial orthologs (Onchocerca volvulus, Dirofilaria immitis), the corresponding model organism C. elegans iPGM ortholog, and the H. sapiens anti-target dPGM isozyme. Both iPGM and dPGM enzymes from E. coli were also included. Low volume, 1536-well plate format kinetic and endpoint assays for the PGM-catalyzed conversion of 3-PG to 2-PG were developed (FIG. 2A). Each assay utilized a coupled enzyme approach where the product 2-PG is driven through phosphoenol pyruvate (PEP) to pyruvate and ATP via enolase and pyruvate kinase, respectively (Feraudi et al., J. Clin. Chem. Clin. Biochem. 21:193-197, 1983). A kinetic absorbance output was achieved using lactate dehydrogenase-mediated changes in NADH concentration through pyruvate conversion to lactate (FIG. 2B) (Fuad et al., Metallomics 3:1310-1317, 2011; White et al., Eur. J. Biochem. 207:709-714, 1992). For a bioluminescent endpoint assay the ATP produced is used in light production by Firefly luciferase and luciferin (FIG. 2B, Table 1). The continuous NADH-dependent absorbance assay was used to determine the relative activity and 3-PG $K_M$ for each of the seven PGM orthologs and isozymes being used in this study. Each of these enzymes and conditions was used to calibrate the bioluminescent end-point assay that gave a 3.5-5.4-fold ratio of signal-to-background following a five minute incubation (FIG. 1C and Table 7).

TABLE 7

Assay summary statistics

| PGM | Output Signal (RLU) | S:B | CV | Z' Factor | Control condition |
|---|---|---|---|---|---|
| B. malayi iPGM | 22000 ± 6500 | 4.4 ± 1.8 | 3.4 ± 1.0 | 0.81 ± 0.06 | No Enzyme |
| C. elegans iPGM | 19000 ± 5400 | 3.6 ± 1.5 | 4.0 ± 1.3 | 0.76 ± 0.11 | No Enzyme |
| O. volvulus iPGM | 25000 ± 6300 | 4.7 ± 2.2 | 4.7 ± 2.1 | 0.79 ± 0.10 | No Enzyme |
| D. immitis iPGM | 20000 ± 7000 | 3.8 ± 2.2 | 4.2 ± 2.4 | 0.74 ± 0.15 | No Enzyme |
| E. coli iPGM | 1700 ± 4100 | 3.1 ± 1.2 | 4.0 ± 2.1 | 0.72 ± 0.16 | No Enzyme |
| H. sapiens dPGM | 19000 ± 3200 | 3.7 ± 1.4 | 4.0 ± 0.9 | 0.75 ± 0.10 | No Enzyme |
| E. coli dPGM | 23000 ± 3900 | 3.8 ± 1.5 | 3.7 ± 1.3 | 0.77 ± 0.11 | No Enzyme |
| PK-FLuc | 29000 ± 5300 | 5.2 ± 2.0 | 3.3 ± 1.0 | 0.77 ± 0.18 | No Enzyme |

For the direct evaluation of compounds and cyclic peptides on the target enzyme, gradient elution moving boundary electrophoresis (GEMBE) (Shackman et al., *Anal. Chem.* 79:565-571, 2007; Strychalski et al., *Anal. Chem.* 81:10201-10207, 2009) was used to enact an electrophoretic separation of 3-PG from 2-PG (FIG. 2C, FIG. 3A). The method provides a direct, label-free measurement of the substrate and product, 3-PG and 2-PG (FIG. 3B top). Baseline separation of the isomers was clearly apparent in the first derivative plot (FIG. 3B, bottom) for equimolar amounts of 3-PG and 2-PG. Using the established separation conditions, a time course for conversion of 2-PG to 3-PG was demonstrated with the *C. elegans* and *B. malayi* iPGMs. GEMBE, while low throughput, provides an ideal orthogonal validation of the activity of the iPGM inhibitors described in this study.

Example 4

Identification of a Potent and Selective Class of iPGM Inhibitors

The parasitic target *B. malayi* iPGM was initially panned against the macrocyclic peptide library to obtain seven macrocycles represented by tetradeca-through undecapeptides, Bm-1-Bm-7 (Table 6). From the nucleic acid sequences (FIGS. 4A-4C) encoding these cyclic peptides sufficient quantities for evaluation as inhibitors of the enzymatic activity of a panel of seven PGM orthologs and isozymes were synthesized (Table 6). Concentration response curves obtained for Bm-1-7 across the PGM panel primarily revealed a selective, modestly potent macrocyclic series. All except Bm-2 (for which RaPID selection may have been influenced by the tethered nucleic acid not present in the resynthesized cyclic peptide) inhibited the iPGM orthologs in the high nanomolar to low micromolar range (Table 6), and further showed complete selectivity for iPGM vs. dPGM enzymes. These cyclic peptides comprised two groups, one having large rings of 12 or 13 amino acids with short 1-2 amino acid tails (Bm-1-Bm-3) and the second having 7-membered rings with C-terminal extensions of between 3-4 amino acids (Bm-4-Bm-7), and all seven peptides contained a cysteine at the penultimate position. Because Bm-4 represented the shorter, potent undecapeptide class of sequences among the cyclic peptides it was selected as a template for additional study through C-terminal truncation analogs. Additionally, to probe the importance of the free sulfhydryl group of the tail cysteine, Cys10 was replaced with Ser. Interestingly, the Cys10Ser replacement and elimination of all but the terminal Gly11 resulted in inactive macrocycles (Table 3).

Figure 10A:
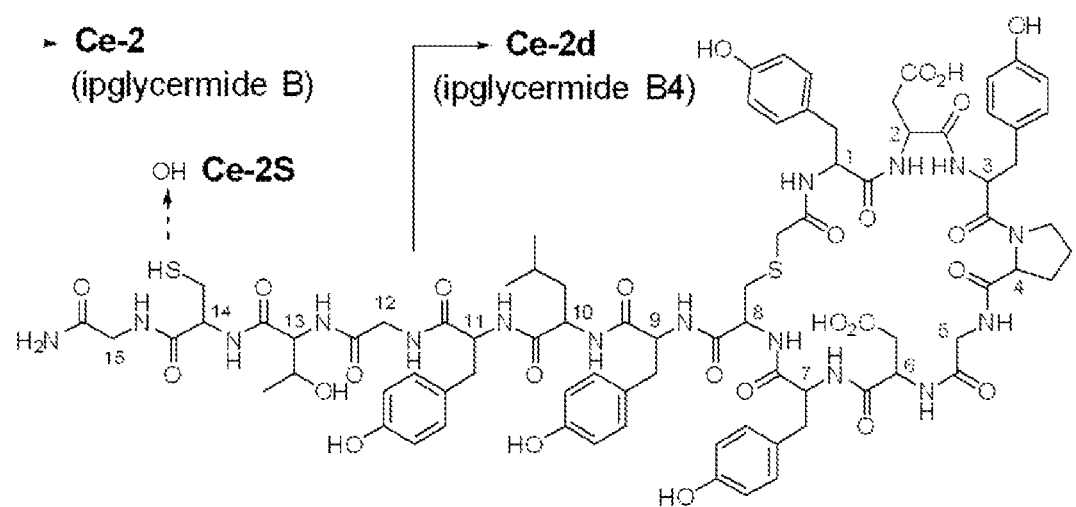
FIGS. 10A-10E are a series of panels showing pharmacologic-phylogenetic relationship of iPGM macrocyclic peptide inhibitors.
Figure 10B:
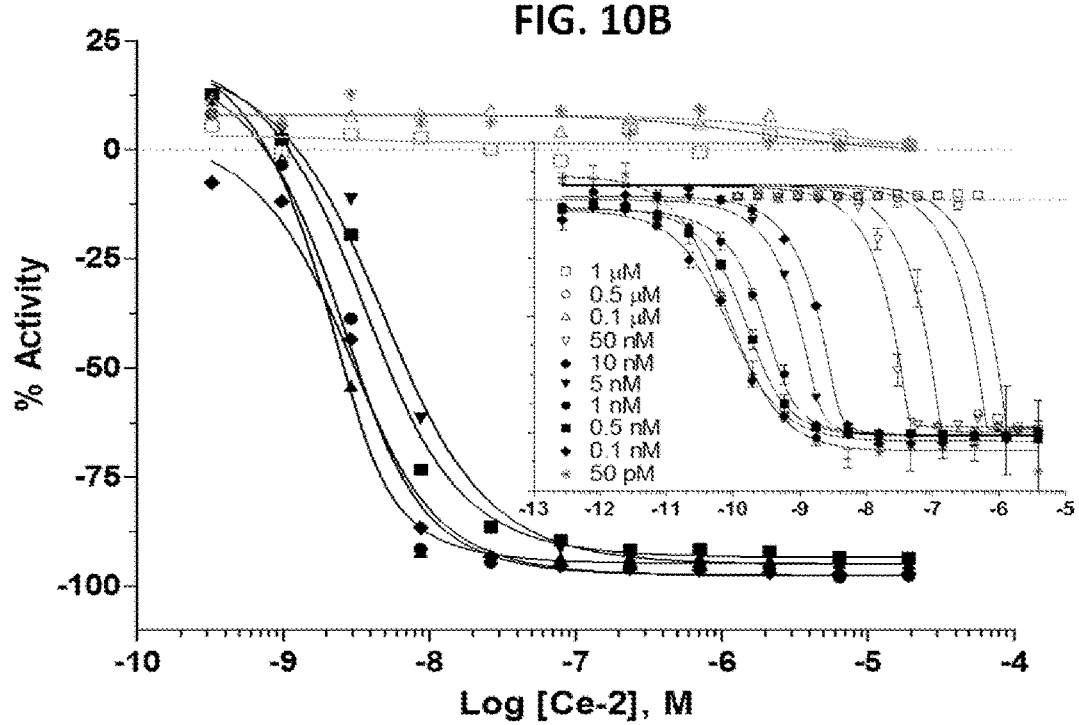

The Bm-series cyclic peptides were relatively low potency. Additionally *B. malayi* has proven refractory to crystallographic structure determination. However, successful crystals were obtained for *C. elegans* iPGM and motivated RaPID targeting of this ortholog towards the deduction of design rules guiding macrocycle-iPGM interactions. A second affinity selection experiment using the *C. elegans* model organism iPGM yielded four macrocyclic peptides, either pentadecapeptides, ipglycermides A (Ce-1) and B (Ce-2, FIG. 10A) or tetradecapeptides (Ce-3, Ce-4). As in the corresponding *B. malayi*-derived series ring systems the macrocycles are completely inactive toward the dPGM isozymes. Two of these, Ce-1 and Ce-2, ipglycermide A and B, respectively, were exceedingly potent inhibitors of the iPGM orthologues nominally exhibiting low nM activity (2-20 nM) under the initial conditions (that is, the [iPGM] for *C. elegans*, *B. malayi* was 5 nM, for *D. immitis*, *E. coli* 10 nM and *O. volvulus* 20 nM) used in the endpoint profiling assays, and were recapitulated in the GEMBE-based assay for the selected PGMs shown in FIGS. 11A-11B. The steep concentration response curves observed at enzyme concentrations 5 nM and higher for Ce-2 (FIGS. 10B-10D, 11A, 11B) suggest stoichiometric titration of the enzymes, which would occur under conditions where $[E] > K_d$ of the ligand, and therefore lead to an underestimation of potency. This was supported by the hyperbolic response of the concentration response curves and leftward shift in ipglycermide B $IC_{50}$ as the iPGM concentration was taken below 5 nM (FIG. 10B). Using a quadratic model to account for stoichiometric binding at high iPGM concentration the family of concentration response curves in FIG. 10B was used to estimate an effective $K_d$ of 73±15 pM for ipglycermide B.

Example 5

Ipglycermide B (Ce-2) Analogs Define a Pharmacologic-Phylogenetic Relationship to iPGM Orthologs Ce-2 was chosen as a template for a structure activity relationship study involving a C-terminal truncation/substitution series and used to define the minimal sequence needed for activity. This cyclic peptide was also used to explore linear analogs to determine the effect on affinity from conformational constraining the sequence (see Table 8 and FIG. 12A-12B). While removing the majority of the linear sequence of Ce-2 resulted in loss or greatly diminished iPGM inhibitory activity (Ce-2e to Ce-2g), truncated analogs Ce-2a to Ce-2d resulted in a broadened range of activity among the iPGM orthologs. Of particular note is the retention of nanomolar activity of analog Ce-2d for *C. elegans* and *E. coli* iPGM, while the activity for *B. malayi*, *O.*

Figure 10C:
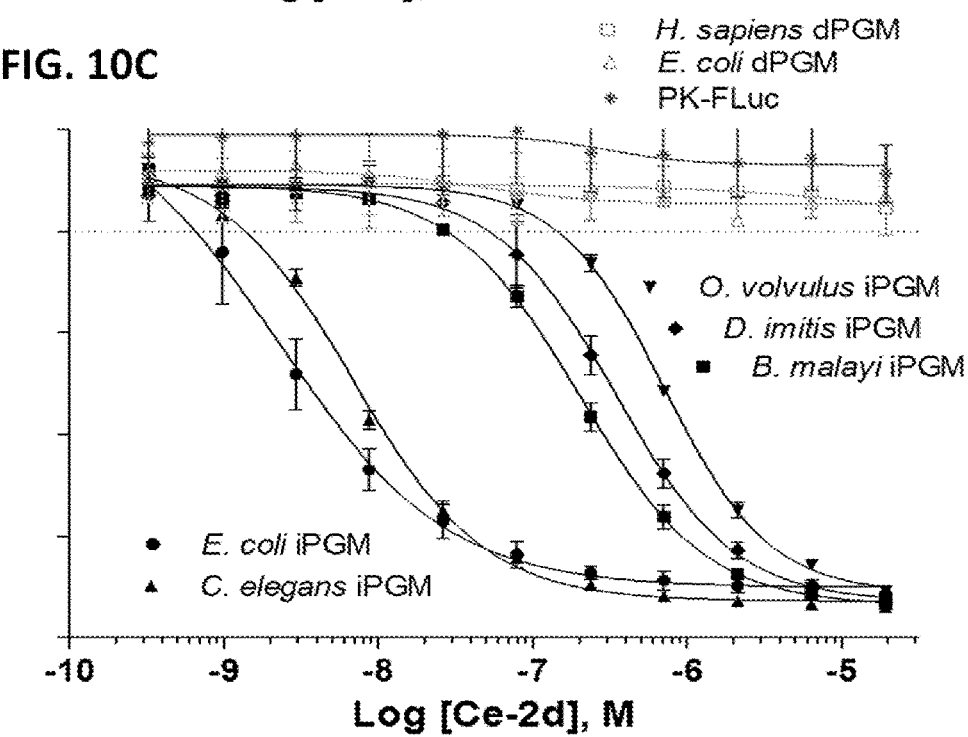
Figure 10D:
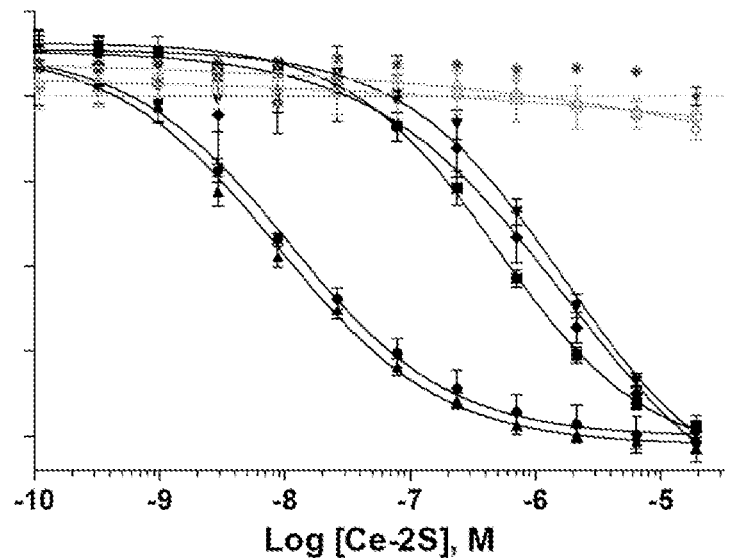
Figure 10E:
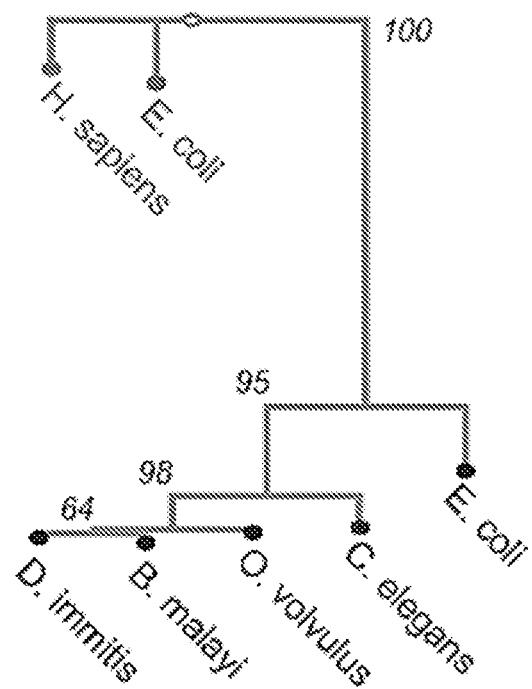
Figure 11A:
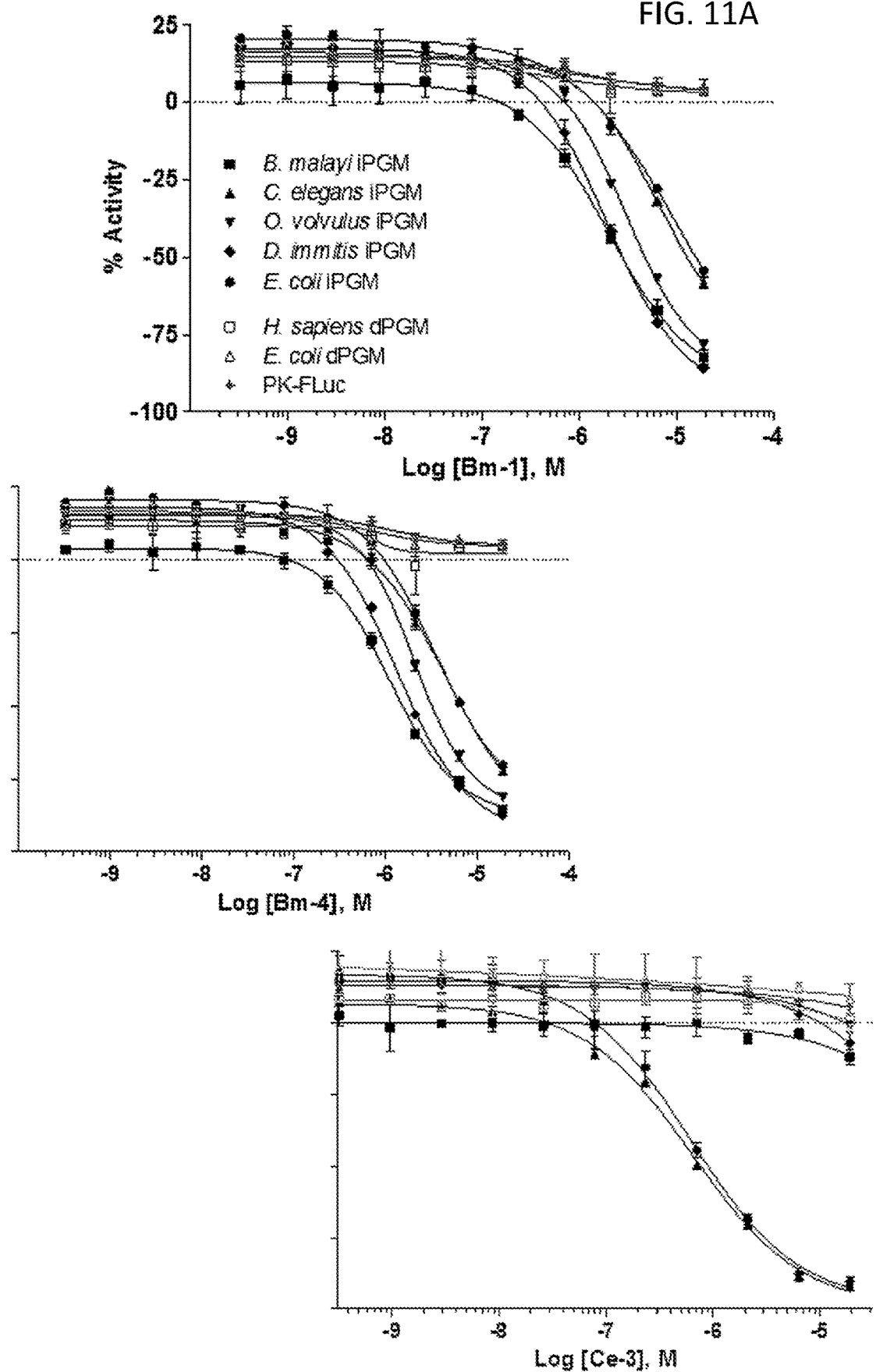
FIGS. 11A-11C are a series of representative concentration response curves (CRCs) for iPGM inhibitory activity of Bm and Ce-cyclic peptides and GEMBE analysis of Ce-2 and Ce-2d.
Figure 11B:
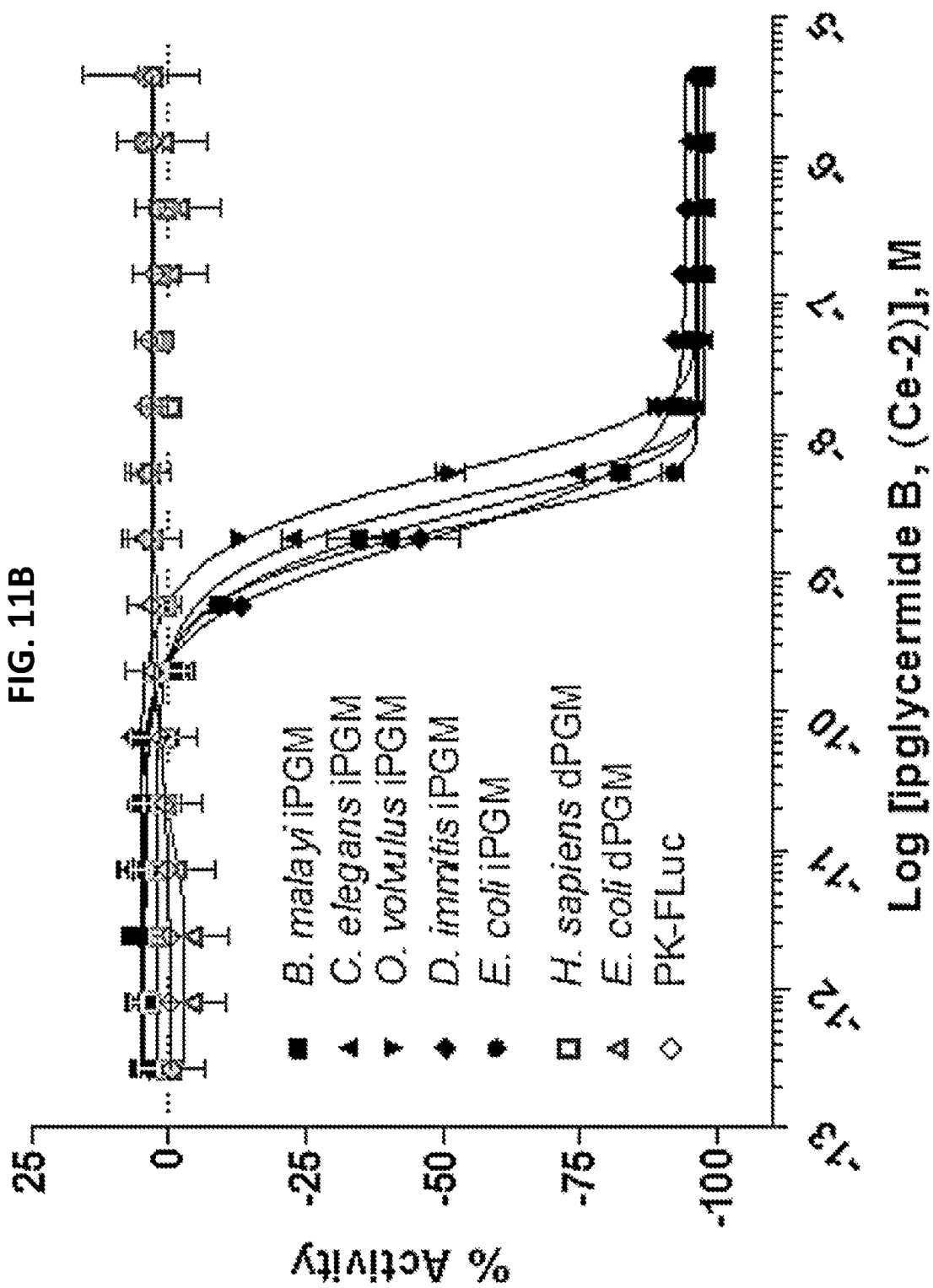
Figure 11C:
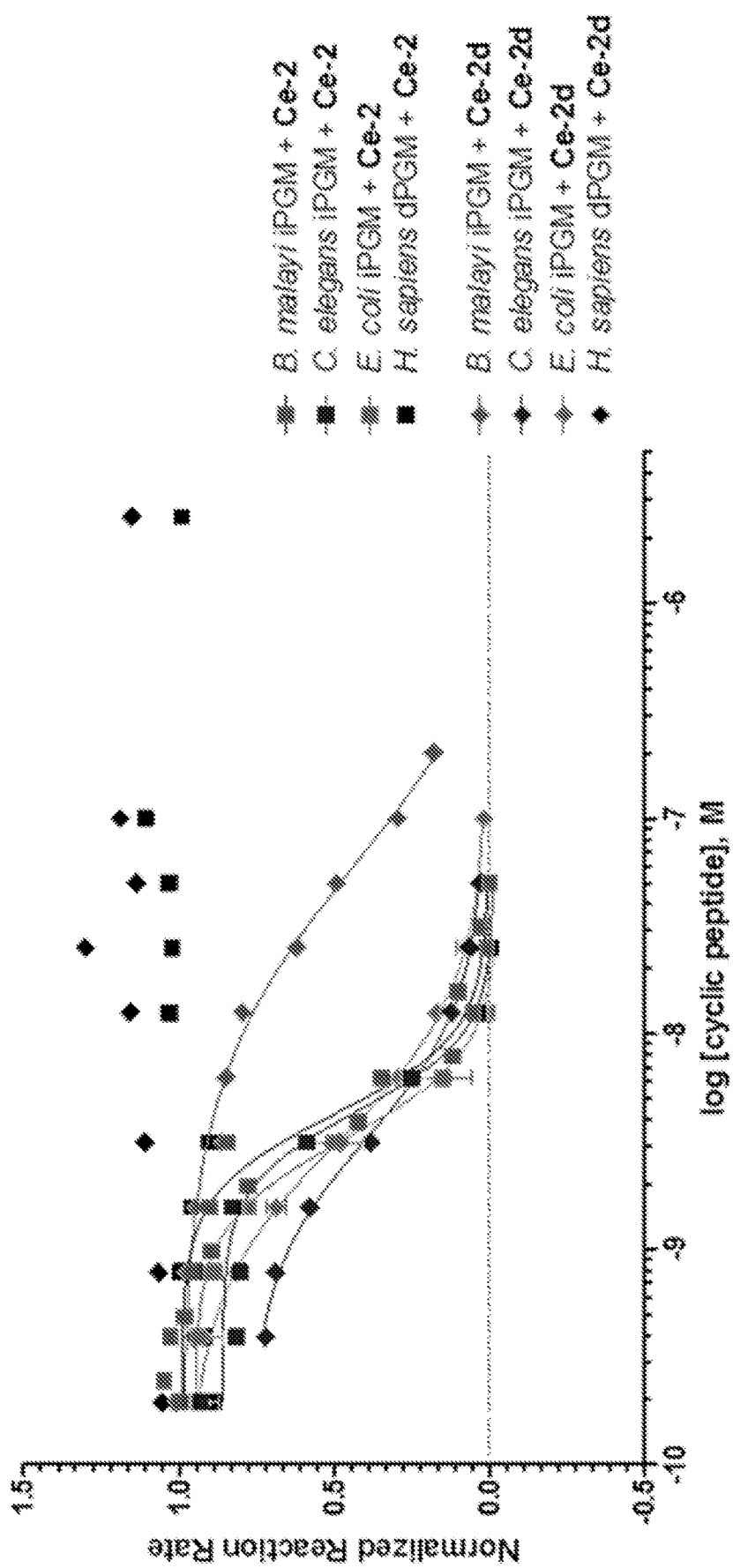
Figure 13A:
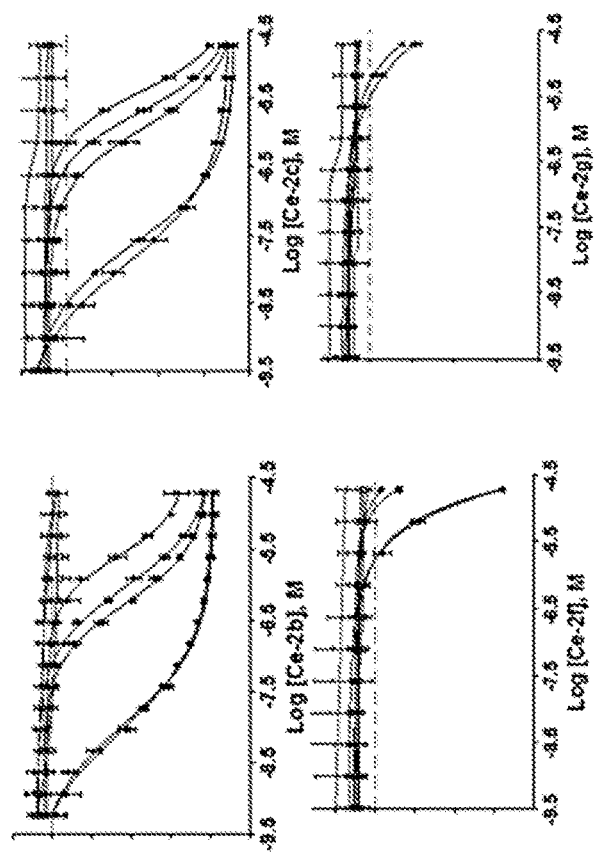
FIGS. 13A and 13B are a series of graphs showing PGM panel activity for macrocyclic peptide analogs of Ce-2.
Figure 13A:
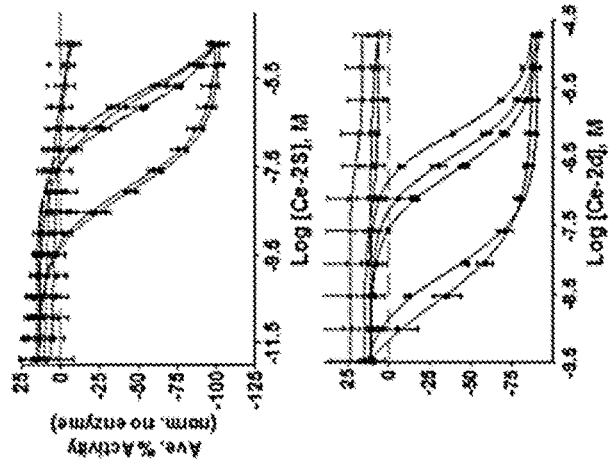
Figure 13B:
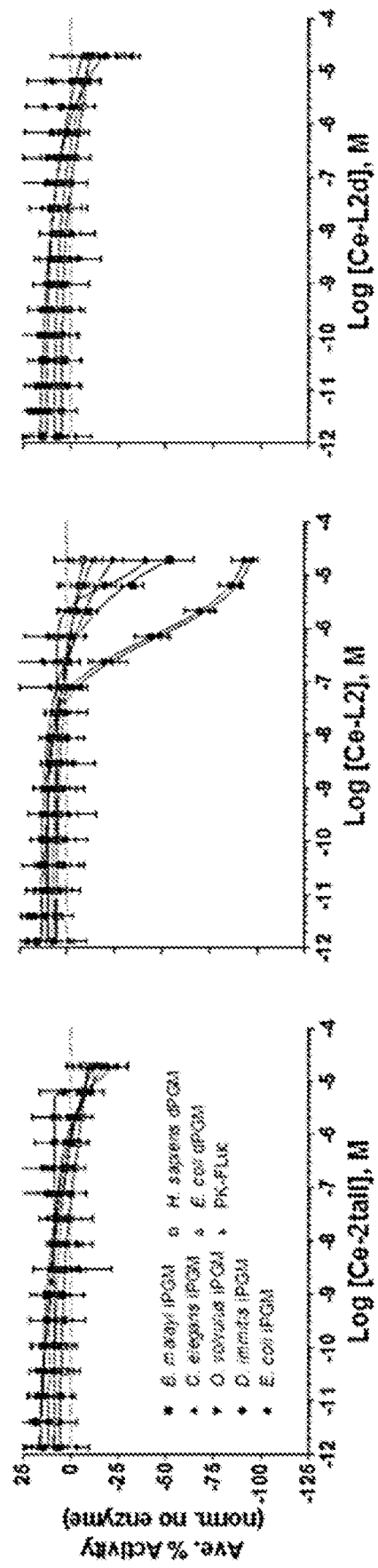

*volvulus*, and *D. immitis* approach IC$_{50}$s in the micromolar range (FIG. 10B and FIGS. 13A-13B). This separation of ortholog activity closely parallels the phylogenetic differences between the amino acid sequences of these enzymes (FIG. 10C).

the catalytic center of iPGM. Finally, while Cys14 contributes to important binding interactions, a peptide devoid of the macrocyclic core comprised solely of Ce-2 residues 9-14 alone (Ce-2tail) was inactive on all PGMs (Table 8; FIG. 13B).The large entropic contribution of macrocyclization of

TABLE 8

Inhibitory properties of ipglycermide B (Ce-2) analogs

| | | pIC$_{50}$ | | | | | | |
|---|---|---|---|---|---|---|---|---|
| Protein ID* | Sequence | C. elegans iPGM | B. malayi iPGM | O. volvulus iPGM | D. immitis iPGM | E. coli iPGM | H. sapiens dPGM | E. coli dPGM |
| Ce-2 | \|⎯⎯s⎯⎯\|<br>$^{Ac-D}$YDYPGDYCYLYGTCG<br>(SEQ ID NO: 2) | 9.60 | 9.02 | 9.18 | 9.36 | 9.26 | NA | NA |
| Ce-2S | \|⎯⎯s⎯⎯\|<br>$^{Ac-D}$YDYPGDYCYLYGTSG<br>(SEQ ID NO: 6) | 8.08 | 6.28 | 5.99 | 6.01 | 8.00 | NA | NA |
| Ce-2a | \|⎯⎯s⎯⎯\|<br>$^{Ac-D}$YDYPGDYCYLYGTC<br>(SEQ ID NO: 17) | 9.76 | 9.49 | 9.68 | 9.91 | 9.58 | NA | NA |
| Ce-2b | \|⎯⎯s⎯⎯\|<br>$^{Ac-D}$YDYPGDYCYLYGT<br>(SEQ ID NO: 18) | 7.80 | 6.16 | 5.61 | 5.96 | 7.98 | NA | NA |
| Ce-2c | \|⎯⎯s⎯⎯\|<br>$^{Ac-D}$YDYPGDYCYLYG<br>(SEQ ID NO: 19) | 7.64 | 5.93 | 5.41 | 5.70 | 7.98 | NA | NA |
| Ce-2d | \|⎯⎯s⎯⎯\|<br>$^{Ac-D}$YDYPGDYCYLY<br>(SEQ ID NO: 5) | 9.03 | 7.29 | 7.13 | 6.20 | 7.98 | NA | NA |
| Ce-2e | \|⎯⎯s⎯⎯\|<br>$^{Ac-D}$YDYPGDYCYL<br>(SEQ ID NO: 20) | 7.16 | 5.53 | 4.72 | 5.32 | 7.27 | NA | NA |
| Ce-2f | \|⎯⎯s⎯⎯\|<br>$^{Ac-D}$YDYPGDYCY<br>(SEQ ID NO: 21) | 4.29 | NA | NA | NA | 4.59 | NA | NA |
| Ce-2g | \|⎯⎯s⎯⎯\|<br>$^{Ac-D}$YDYPGDYC<br>(SEQ ID NO: 22) | NA | NA | NA | NA | NA | NA | NA |
| Ce-L2 | $^{Ac-D}$YDYPGDYSYLYGTCG<br>(SEQ ID NO: 7) | 5.94 | 4.89* | 5.18* | 5.18* | 5.88 | NA | NA |
| Ce-L2d | $^{Ac-D}$YDYPGDYSYLY<br>(SEQ ID NO: 8) | NA | NA | NA | NA | NA | NA | NA |
| Ce-2tail | $^{Ac-D}$YLYGTCG<br>(SEQ ID NO: 9) | NA | NA | NA | NA | NA | NA | NA |

NA = no appreciable activity.
Each peptide had a C-terminal amide
*Estimated from incomplete concentration response curves (FIG. 13B)

Other than Ce-2, only Ce-2a, resulting from Gly14 truncation, retained subnanomolar potency against the iPGM orthologs (Table 8) pointing to Cys14 as a key determinant in high-affinity binding. Isosteric replacement of Cys14 with Ser in Ce-2 to generate Ce-2S caused an approximately 100-fold decrease in inhibitory activity (IC$_{50}$~10 nM) for the *C. elegans* and *E. coli* iPGMs, and comparable to Ce-2d a separation in potency of 100-fold between the iPGMs of *C. elegans* and *E. coli* versus *B. malayi, O. volvulus*, and *D. immitis* (FIG. 10B). These results indicate that the high-affinity binding of Ce-2 is dependent on its Cys14 thiol, possibly involving a sulfur-transition metal ion interaction at the peptide was demonstrated by comparing the IC$_{50}$s between Ce-2 and a linear form of Ce-2 made by a Cys8Ser substitution (Ce-L2) for iPGMs on which there was measurable activity of Ce-L2. The most reliable data from *C. elegans, O. volvulus*, and *E. coli* iPGM (see FIG. 13B and Table 8) allowed a calculation of between a 2000- and 10,000-fold enhancement in affinity attributable to reduction of random states by macrocycle formation, though a potential steric clash between hydrogens replacing the thioether bond may contribute as well to this greatly decreased inhibitory activity. A related peptide derived from a linear form of Ce-2d, Ce-L2d, was completely inactive on all iPGMs, further supporting the importance of two functional lariat macrocycle sub-domains, the ring system and C-terminus, both necessary to engender high affinity binding to the Ce-2 macrocycle.

Example 6

Structure of Nematode iPGM

The iPGMs are monomeric bi-domain enzymes where a phosphatase domain, structurally related to the alkaline phosphatase family of binuclear metalloenzymes, is connected by two hinge peptides to a phosphotransferase domain (Jedrzejas et al., *EMBO J.* 19:1419-1431, 2000). X-ray crystal structures have been obtained for the enzymes derived from two trypanosomatids and several bacterial species (Jedrzejas et al., *EMBO J.* 19:1419-1431, 2000; Mercaldi et al., *FEBS J.* 279:2012-2021, 2012; Nowicki et al., *J. Mol. Biol.* 394:535-543, 2009; Nukui et al., *Biophys. J.* 92:977-988, 2007).

Figure 7C:
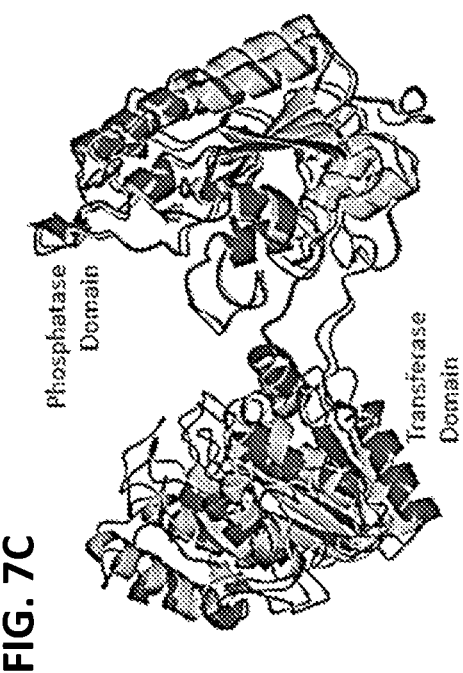

To develop a structural model delineating the molecular interactions mediating the pharmacologic-phylogenetic relationship between the macrocycles and iPGM orthologs we attempted to co-crystallize Ce-2 with *B. malayi* and *C. elegans* iPGM, but failed to obtain crystals. Although soaking of pre-formed iPGM crystals with Ce-2 caused the crystals to shatter, two apo crystal forms were obtained, monoclinic P (iPGM-m) and orthorhombic P (iPGM-o) lattices (FIG. 6A-6C), of native *C. elegans* iPGM providing the first structure of a nematode iPGM (Table 4 and FIG. 7A-7C). As anticipated from primary amino acid sequence homology among iPGM orthologs, *C. elegans* iPGM is quite similar to other iPGMs of bacterial origin (FIG. 14). Superposition of the monoclinic *C. elegans* apo iPGM (PDB: 5KGM) structure with *Bacillus anthracis* apo iPGM (PDB: 2IFY) yielded an RMSD of 2.76 Å between Cα atoms (476 residues aligned). Though the deviation from superposition is fairly large between the two structures, the overall fold is very similar (FIGS. 8A-8C). The structure of monoclinic *C. elegans* iPGM was also compared with that of a substrate bound iPGM from *Bacillus stearothermophilus* (PDB: 1098). Superposition yielded an RMSD of 1.07 Å between Cα atoms. However, only 282 residues could be aligned for residues in the transferase domain since substrate binding produces a large conformational change in the phosphatase domain (FIGS. 8A-8C). Similar to other iPGMs, $Mn^{2+}$ occupies one of the two phosphatase domain metal ion binding sites while, as in alkaline phosphatase, a $Zn^{2+}$ ion was found in the second binding site of *C. elegans* iPGM. The identity of these transition metal ions was verified from phased anomalous difference maps calculated from data collected at wavelengths of 1.0000 Å and 1.9016 Å. These metal ions contact the histidine and aspartate triads as shown in FIGS. 9A-9C at coordination distances listed in Table 5, and the catalytic Ser86 nucleophile coordinates to the $Zn^{2+}$ ion.

Example 7

Figure 6D:
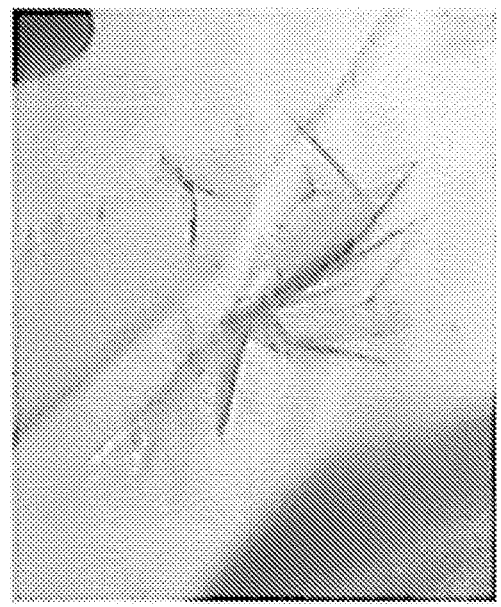
Figure 15B:
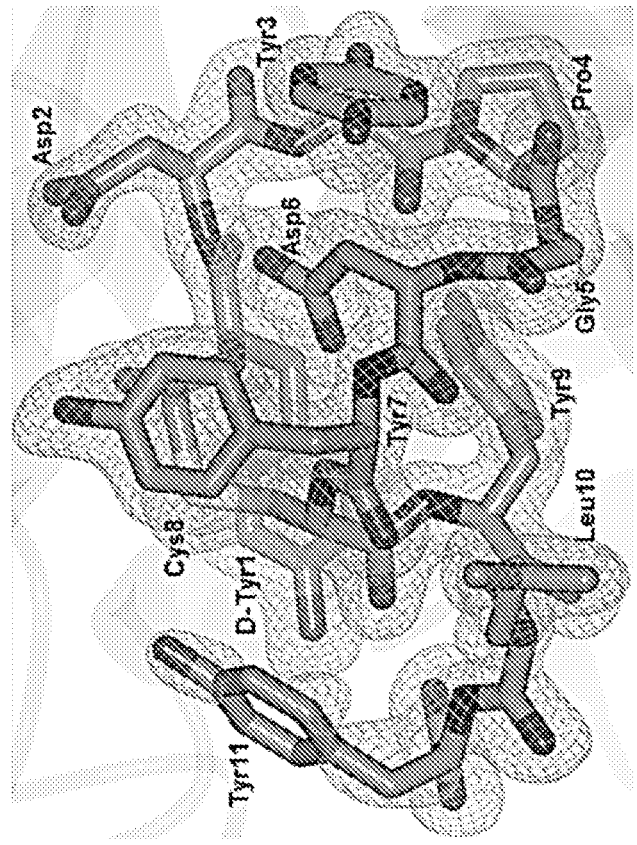
FIGS. 15A-15C are a series of diagrams showing the structure of iPGM•Ce-2d complex asymmetric unit.
Figure 15A:
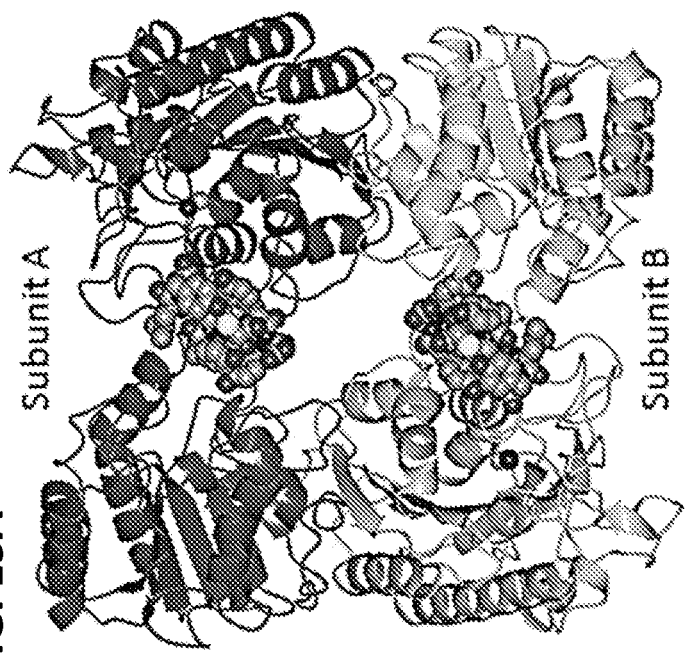
Figure 15C:
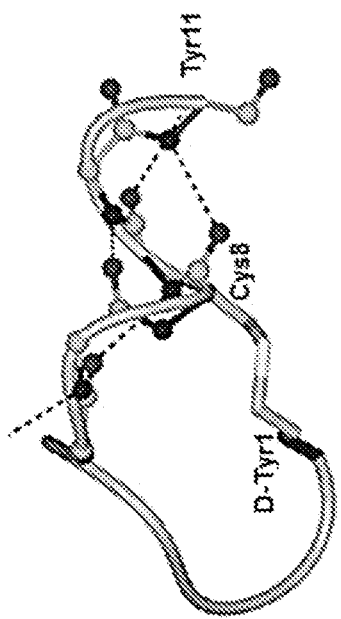
Figure 15C:
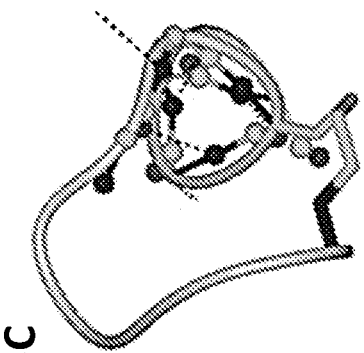
Figure 16B:
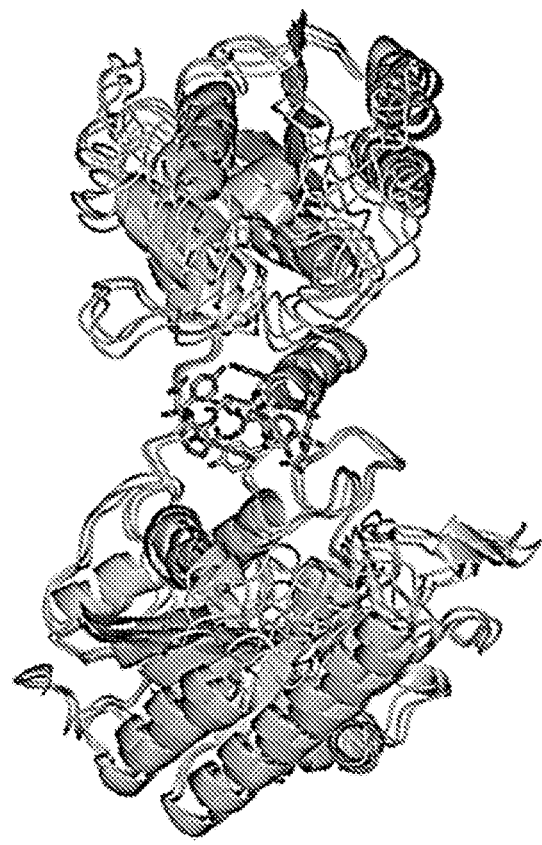
FIGS. 16A-16E are a series of diagrams showing Ce-2d traps iPGM in an open conformation.
Figure 16A:
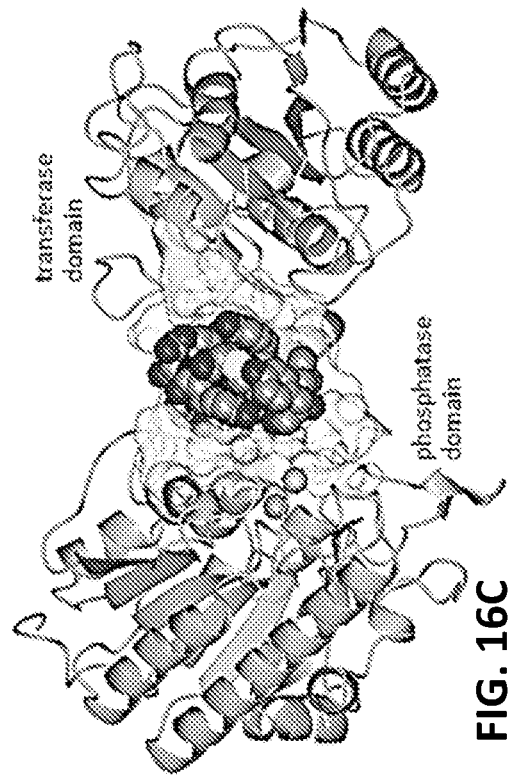
Figure 16E:
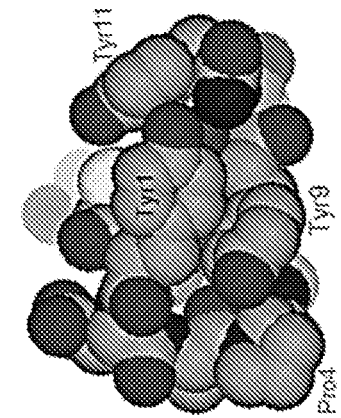
Figure 16D:
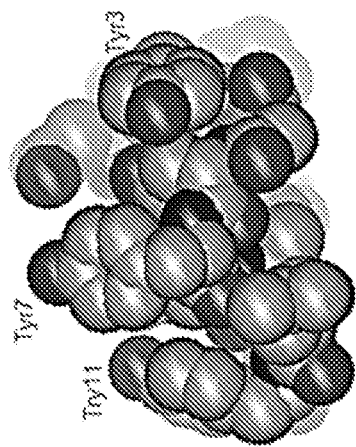
Figure 16C:
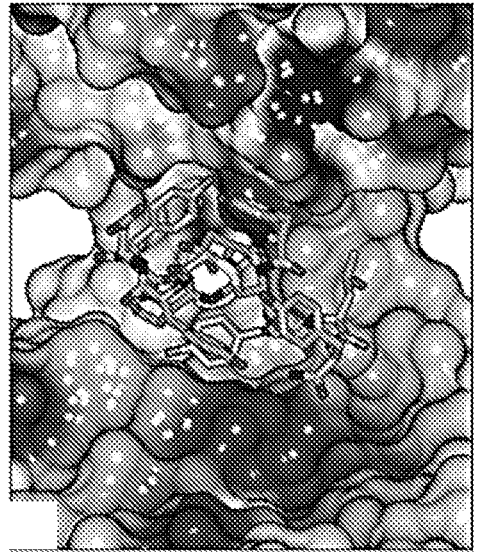

Co-Crystal Structure of iPGM•Macrocyclic Complex Elucidates Locked-Open Inhibitory Mechanism From the apo iPGM structure it was observed that the N-terminal 18 amino acids, unique to *C. elegans* iPGM, were disordered. In a subsequent crystallization effort, using an 18 amino acid N-terminal truncated form of *C. elegans* iPGM, a pre-formed Ce-2 complex purified by sizing chromatography was prepared, as well as a mixture with Ce-2d. The latter resulted in needle like crystals diffracting to 1.95 Å (FIG. 6D and Table 4). The final model of the iPGM•Ce-2d complex (PDB: 5KGN) contained two molecules in the asymmetric unit (FIG. 15A), articulating an inter-domain binding mode with the macrocycle cradled in a pocket shaped from the hinge peptides and adjacent phosphatase and transferase domain surfaces (FIG. 16A). The two subunits of the asymmetric unit are nearly identical with an RMSD deviation of 0.20 Å between Cα atoms for 520 residues aligned. Therefore all subsequent analyses were carried out using subunit A of the model. The structure of iPGM•Ce-2d was compared with the aforementioned apo iPGM-m and iPGM-o (PDB: 5KGL) structures. Superposition yielded an RMSD deviation of 1.98 Å (503 residues) and 2.05 Å (502 residues), respectively. Although the RMSD deviations are somewhat large, the overall structures are remarkably similar (FIG. 16B) with slight displacement of secondary structure elements due to the high flexibility of iPGM. The cavity that accommodates the binding of the Ce-2d cyclic peptide is very similar amongst all of the structures with no dramatic conformational changes observed to accommodate binding of the peptide. Rather, it appears that the peptide adopts an optimal fit within this cavity as might be expected from the affinity selection approach used here to discover the parent macrocycle. This region of iPGM forms a somewhat negative asymmetrically charged pocket that accommodates the polar residues of Ce-2d as shown in FIG. 16C. Ce-2d has a total surface area of 432.1 Å$^2$ and contacts iPGM with a total area of 127.1 Å$^2$ as calculated using Areaimol (Lee et al., *J. Mol. Biol.* 55:379-400, 1971), which provides information regarding total area, contact area, and the solvent exposed area of a surface. A relatively small region of the total Ce-2d peptide surface makes direct contact to iPGM (127.1 Å$^2$) with the remaining area (305 Å$^2$) exposed to solvent as it is positioned within an open pocket between the phosphatase and transferase domains. On the basis of molecular weight (1501.6) and its 27 ring atoms, Ce-2d can be categorized as a large macrocycle. With 29% of its surface buried, Ce-2d solvent exposes slightly more surface area than comparably sized macrocycles. The electron density for the cyclic peptide was prominent for all of the residues except for the terminal tyrosine side chain which was somewhat disordered, while the C-terminal 4 residues form a short α-helix (FIGS. 15B and 15C). From the CPK representation of Ce-2d (FIGS. 16C and 16D) the orientation of the tyrosine side chains 3, 7 and 11 can be seen enfolding the cyclic peptide (FIG. 16D) while tyrosine side chains 1 and 9 engage in an edge-to-face interaction (FIG. 16E). In Ce-1, His7 replaces Tyr7 maintaining similar activity (Table 6). The three extra-cyclic C-terminal residues, Tyr9, Leu10 and Tyr11 are wrapped close to the core macrocycle, with the carboxamide of Tyr11 visible on the exterior surface of this compact structure and pointing toward the metal ion active site (FIG. 16E and FIGS. 17A-17C). Notably, the Ce-2d C-terminal amide of the Tyr11 residue is 6.5 Å and 8.4 Å from the $Mn^{2+}$ and $Zn^{2+}$ ions, respectively (FIG. 17C). Thus, it is feasible that the longer C-terminus of Ce-2 (and Ce-1) could potentially extend from this cavity, positioning Cys14 within coordination distance to either metal ion.

The Ce-2d macrocycle forms direct hydrogen bonds with *C. elegans* iPGM as well as water mediated contacts as depicted in FIGS. 17A and 17B and detailed in Table 5. Two of these key H-bonds are made with C-terminal tail residues, Tyr9 and the carboxamide of Tyr11. Others include, iPGM Arg289 which forms two H-bonds with Ce-2d ring system residues, one directly with Asp2 and one water-mediated through the Tyr3 hydroxyl (FIG. 17B), while a bifurcated Gly5 carbonyl H-bond occurs with iPGM via Gln101 and Asp102 (FIG. 17B). Hydrophobic interactions were also observed, for example Leu10 of the macrocycle sits in a small pocket formed by iPGM Ile103, Leu78 and Leu82 (FIG. 18A-18B), while Ile99 of the enzyme is within 3.5 Å or less of cyclic peptide residues Tyr9, Leu 10 and Tyr7.

Figure 17D:
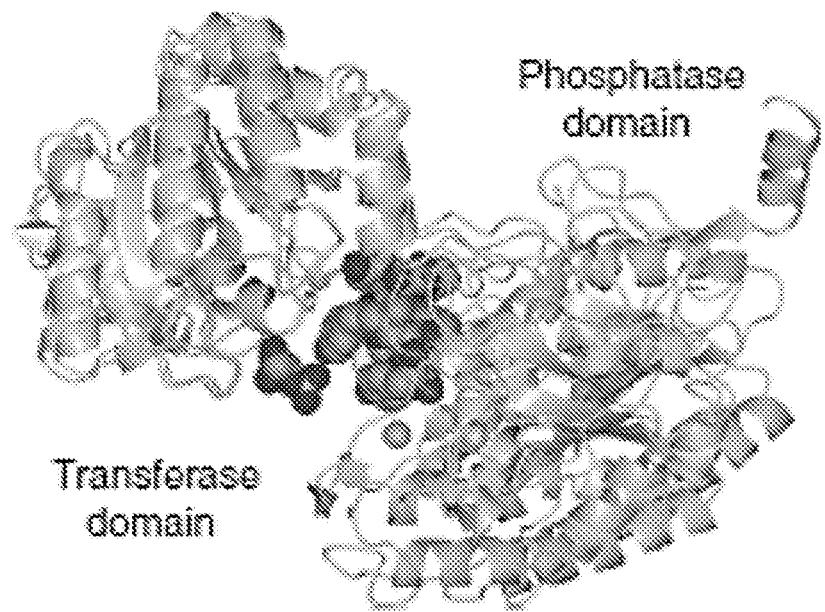
Figure 17E:
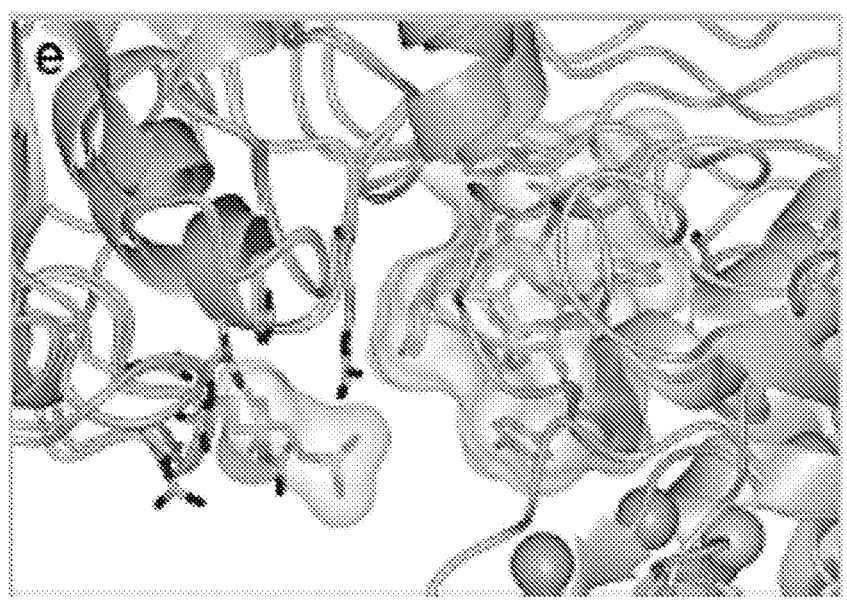
Figure 18A:
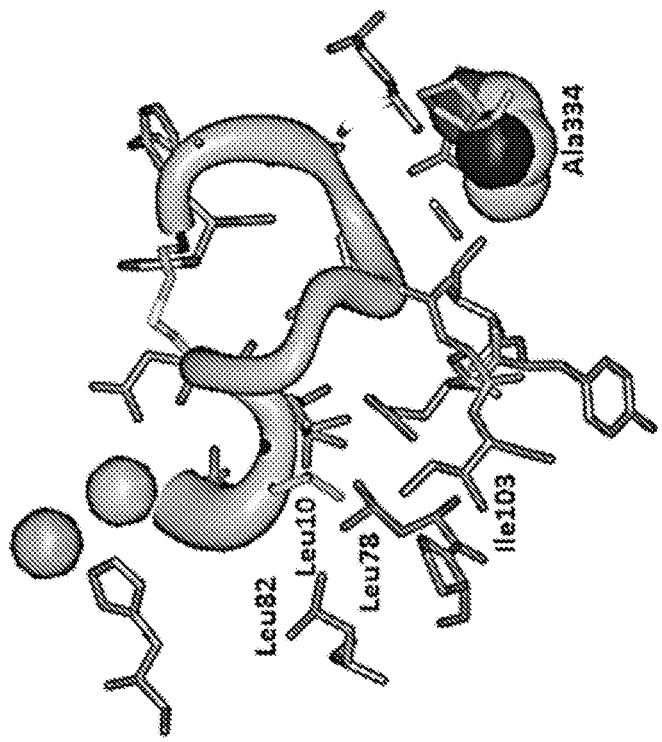
FIGS. 18A and 18B are diagrams showing the hydrophobic pocket occupied by Leu10 of Cd-2d.
Figure 18B:
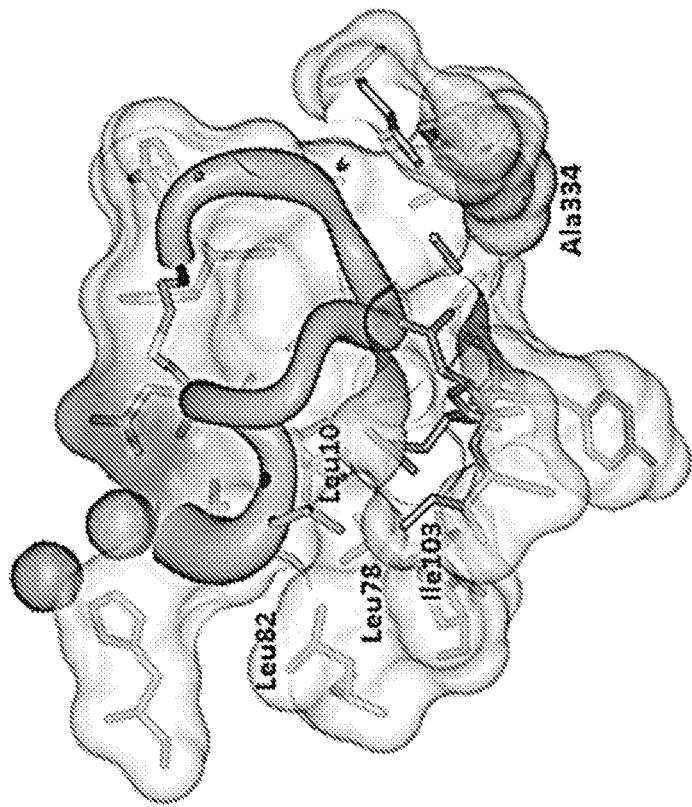
Figure 22A:
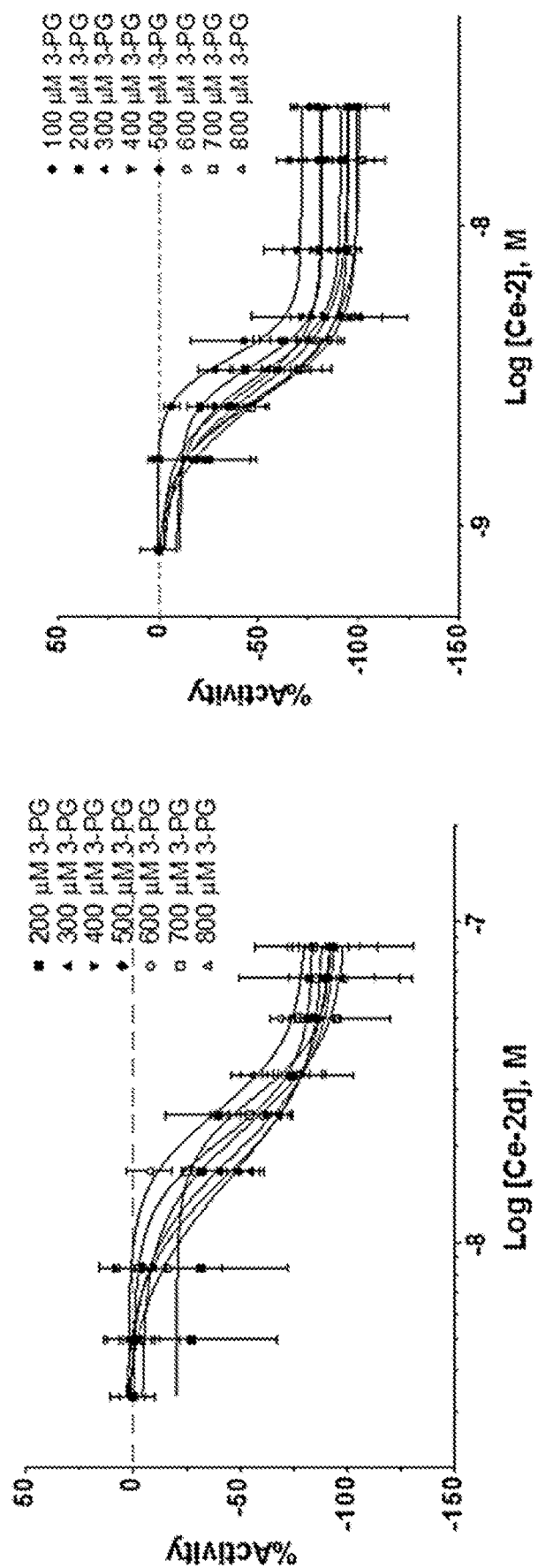
FIGS. 22A and 22B are a series of plots showing Concentration response curves (FIG. 22A) and $IC_{50}$ variation (FIG. 22B) for Ce-2 (right) and Ce-2d (left) tested across varying concentrations of 3-PG substrate. Fifteen minute post substrate addition as measured by a continuous NADH-dependent absorbance assay. The *C. elegans* iPGM concentration used was ~5 and ~15 nM for Ce-2 and Ce-2d respectively. Absorbance values were normalized to no enzyme control and plotted in GraphPad Prism using a 4-paramerter logistic fit for the purpose of estimating $IC_{50}$ values. Error bars represent standard deviation of four replicates. $K_M$ of 3-PG=200 μM as calculated in this study.
Figure 22B:
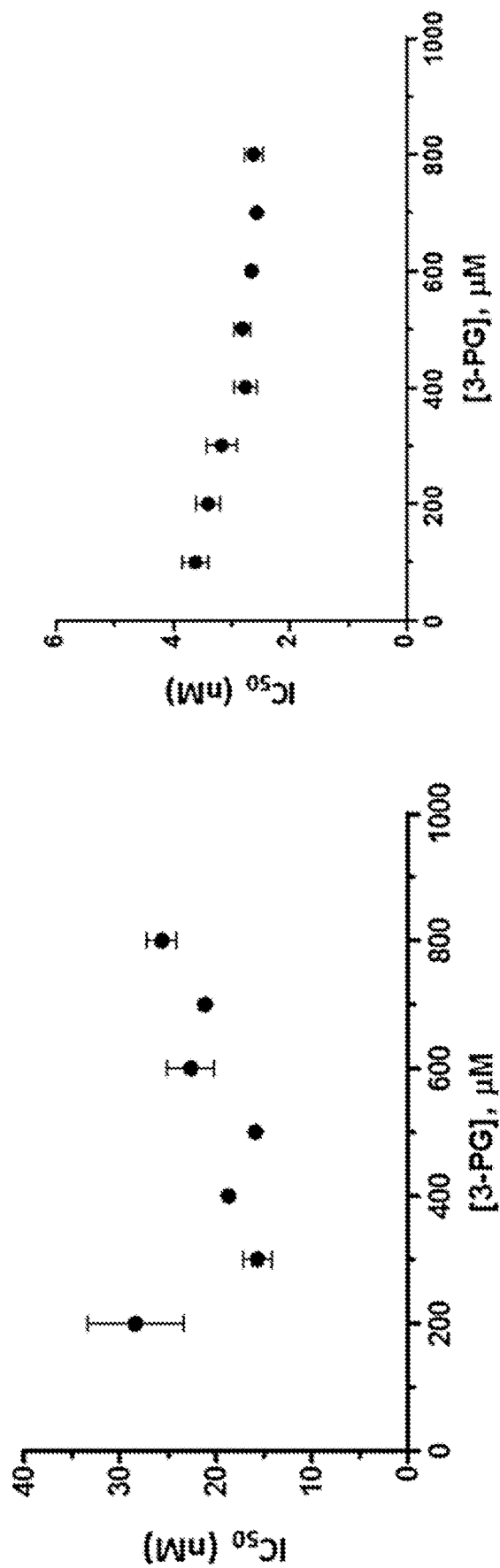

To explore the orientation of Ce-2d binding relative to phosphoglycerate, we superimposed the *S. aureus* iPGM 2-PG-bound and *C. elegans* iPGM Ce-2d crystal structures using the His, Asp, Arg phosphoglycerate binding residues as alignment points in both structures (FIGS. 17D and 17E). The model places the macrocycle at a site non-overlapping with phosphoglycerate supporting an allosteric binding mode for the ipglycermides. This result is consistent with the independence of Ce-2d and Ce-2 IC50 on 3-PG substrate concentration (FIG. 22A-22B).

Figure 19A:
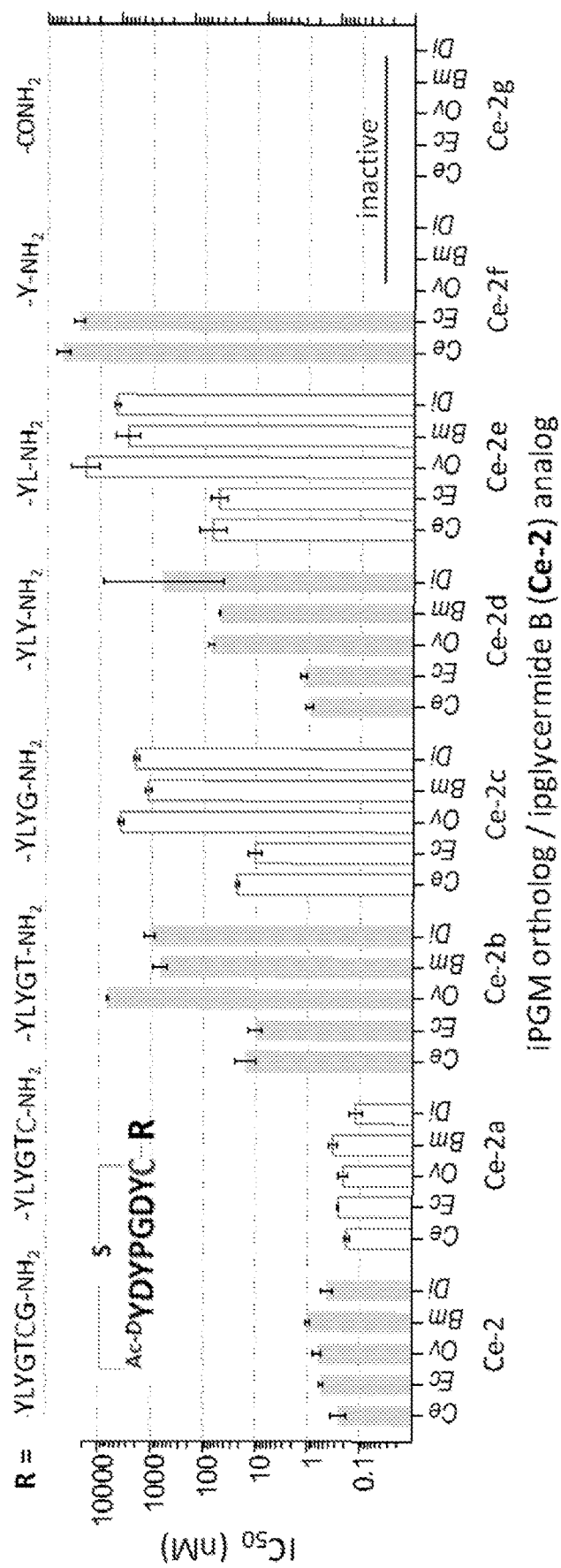
Figure 19C:
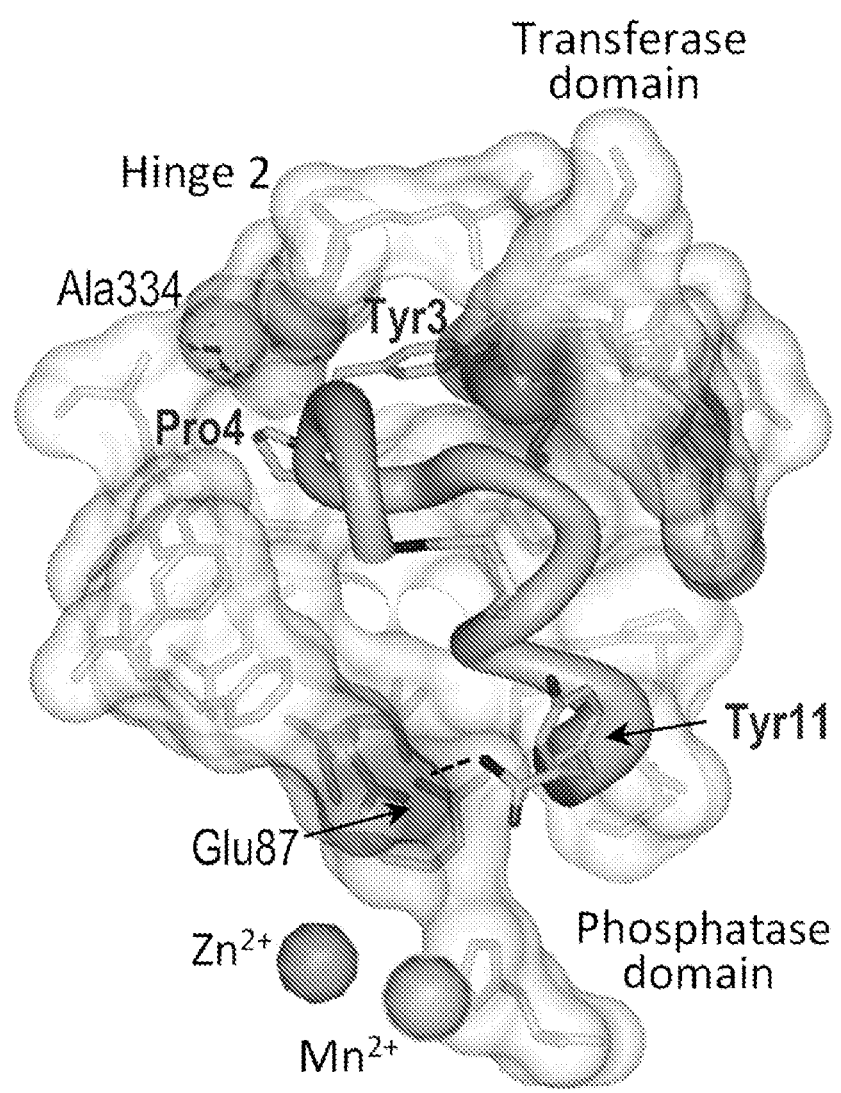

To gain insight into the mechanism underlying the iPGM ortholog selectivity of the Ce-2 series observed in FIG. 19A a binding cavity from residues within 5 Å of the Ce-2d macrocycle (shaded orange in the protein sequence alignment shown in FIG. 19B) was defined. In the cavity defined by these amino acids Ce-2d was projected as a worm representation α-chain scaled by B-factor (gold) with several side chains, Tyr3, Pro4, Tyr11 amide and the thioether linkage shown in green (FIG. 19C), from which several salient observations were made. As previously discussed, truncation of Ce-2 beyond Cys14 resulted in a ~10-fold potency decrease (Ce-2b, c) until Tyr11 becomes the C-terminal residue, at which point potency for *C. elegans* and *E. coli* iPGM was recovered (Ce-2d), but only marginally so for the *B. malayi, O. volvulus,* and *D. immitis* orthologs. The improvement of inhibitory potency was likely the result of a new H-bond made possible by the C-terminal Tyr11 amide of Ce-2d with the highly conserved Glu87 of the phosphatase domain (FIG. 19C). Subsequent removal of Tyr11 resulted in nearly a 100-fold potency decrease, probably a consequence of the Tyr11 amide-Glu87 H-bond forfeiture. Continued truncation led to virtual inactivation of the macrocycle (Ce-2f, g). A possible explanation for the dramatic separation of Ce-2d inhibitory potency between *C. elegans* and *E. coli* vs. *B. malayi, O. volvulus,* and *D. immitis* iPGM orthologs may be in part mediated by Ala334 within hinge 2 of *C. elegans* and *E. coli* iPGM, but replaced by a glutamate in the *B. malayi, O. volvulus,* and *D. immitis* iPGM orthologs. Ala334 is <2.5 Å from Ce-2d Pro4 and Tyr3, thus the larger volume occupied by a glutamic acid residue may create a steric clash only partially compensated for by the Tyr11 amide H-bond. Sequence differences outside the binding cavity between *C. elegans* and *E. coli* vs. the *B. malayi, O. volvulus,* and *D. immitis* iPGMs highlighted in yellow in FIG. 14 could also contribute to ortholog selectivity.

Figure 20B:
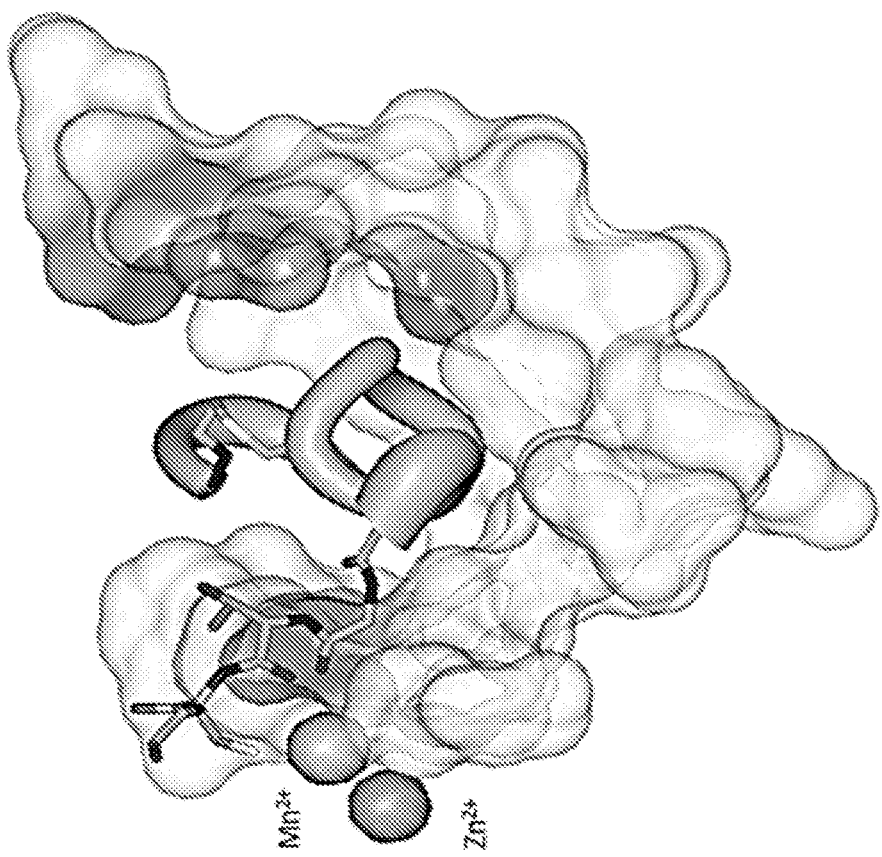
FIGS. 20A and 20B are a pair of diagrams showing modeling of C-terminal residues of Ce-2 onto Ce-2d.
Figure 20A:

From the progressive C-terminal truncation of ipglycermide B (Ce-2) it became apparent that Cys14 engendered the pan-ortholog potency and steep Hill coefficient (>1) to the macrocycle. This observation is consistent with a cysteinyl thiolate functioning as a potential catalytic-site metal ion ligand, particularly plausible with a borderline hard/soft Lewis acid $Zn^{2+}$ at the iPGM active site suggested by the crystallographic findings herein, and its occurrence in related metalloenzymes, e.g., *E. coli* AP (Christianson et al., *Ann. Rev. Biochem.* 68:33-57, 1999). Loss of the sulfhydryl side chain as a consequence of truncation or Cys14Ser substitution results in a more graded Hill slope (<1) of the concentration response curves and potency discrimination among the iPGM orthologs (FIG. 13A). A clear correspondence can be seen between potency and the phylogenetic relationship of the iPGMs (determined from FIG. 10C) as follows: $IC_{50}^{Ce} = IC_{50}^{Ec} \gg IC_{50}^{Bm} > IC_{50}^{Di} \approx IC_{50}^{Ov}$. Taken together these results suggest a positive cooperative binding mechanism whereby the cyclic sequence and majority of the C-terminal extension bind to iPGM positioning the sulfhydryl of Cys14 within coordinating distance to the metal ion site. This mechanism would be consistent with a binding mode resulting in the step-like or ultrasensitive concentration response profile reflected in the steep Hill slope (Shoichet *J. Med. Chem.* 49:7274-7277, 2006; Zhang et al., *Open Biol.* 3:130031, 2013). Modeling of the C-terminal four amino acid residues of Ce-2 onto the iPGM•Ce-2d crystal structure positions the thiolate of Cys14 within coordination distance of the $Mn^{2+}$ ion as illustrated in FIGS. 20A-20B. Interaction with the $Zn^{2+}$ ion would likely require a conformational adjustment in the enzyme possibly explaining the instability of the *C. elegans* apo iPGM crystals upon soaking with Ce-2.

Example 8 iPGM Inhibition by Methylated Peptide Analogs

A series of analogs of Ce-2 (SEQ ID NO: 2) including one or more methylated amide bonds on the linear portion of the peptide were synthesized. The peptides are shown in Table 9. The activity of the analogs was determined as described in Example 1 and results are shown in Table 10.

TABLE 9

Ce-2 N-methyl amide analogs

| Protein ID | Sequence | SEQ ID NO: |
|---|---|---|
| Ce-2h | Ac-DYDYPGDYC$^{Me}$YLYGTCG (cyclic via S) | 55 |
| Ce-2i | Ac-DYDYPGDYCY$^{Me}$LYGTCG (cyclic via S) | 56 |
| Ce-2j | Ac-DYDYPGDYCYL$^{Me}$YGTCG (cyclic via S) | 57 |
| Ce-2k | Ac-DYDYPGDYCYLY$^{Me}$GTCG (cyclic via S) | 58 |
| Ce-2l | Ac-DYDYPGDYCYLYG$^{Me}$TCG (cyclic via S) | 59 |
| Ce-2m | Ac-DYDYPGDYCYLYGT$^{Me}$CG (cyclic via S) | 60 |
| Ce-2n | Ac-DYDYPGDYCYLYGTC$^{Me}$G (cyclic via S) | 61 |
| Ce-2o | Ac-DYDYPGDYCYLYG$^{Me}$T$^{Me}$C$^{Me}$G (cyclic via S) | 62 |
| Ce-2p | Ac-DYDYPGDYCYLYGT$^{Me}$C$^{Me}$G (cyclic via S) | 63 |
| Ce-2q | Ac-DYDYPGDYCYLYG$^{Me}$TC$^{Me}$G (cyclic via S) | 64 |
| Ce-2r | Ac-DYDYPGDYCYLYG$^{Me}$T$^{Me}$CG (cyclic via S) | 65 |
| Ce-2d1 | Ac-DYDYPGDYCYL$^{Me}$Y (cyclic via S) | 66 |
| Ce-2b1 | Ac-DYDYPGDYCYLYG$^{Me}$T (cyclic via S) | 67 |

TABLE 9-continued

Ce-2 N-methyl amide analogs

| Protein ID | Sequence | SEQ ID NO: |
|---|---|---|
| Ce-2b2 | Ac-D YDYPGDYCYL$^{Me}$YGT (with S bridge) | 68 |
| Ce-2b3 | Ac-D YDYPGDYCYL$^{Me}$YG$^{Me}$T (with S bridge) | 69 |

Each peptide had a C-terminal amide

TABLE 10

Inhibitory properties of Ce-2 N-methyl amide analogs

| | iPGM Ortholog | | | | | | | | | | PGM Isozyme | | | | Control | | |
|---|---|---|---|---|---|---|---|---|---|---|---|---|---|---|---|---|---|
| | Bm iPGM | | Ce iPGM | | Ov iPGM | | Di iPGM | | Ec iPGM | | Hs dPGM | | Ec dPGM | | PK-Fluc | | |
| ID | Max Inhib | pIC$_{50}$ | Max Inhib | pIC$_{50}$ | Max Inhib | pIC$_{50}$ | Max Inhib | pIC$_{50}$ | Max Inhib | pIC$_{50}$ | Max Inhib | pIC$_{50}$ | Max Inhib | pIC$_{50}$ | Max Inhib | pIC$_{50}$ | N |
| Ce-2h | −0.7 | NA | −28.8 | 5.05 | 4.2 | NA | 4.7 | NA | −37.7 | 5.05 | 2.0 | NA | 1.2 | NA | 1.5 | NA | 1 |
| Ce-2i | −19.8 | 5.25 | −58.9 | 5 | 1.8 | NA | −14.0 | 5.25 | −82.7 | NA | 7.3 | NA | 4.6 | NA | 2.4 | NA | 1 |
| Ce-2j | −93.2 | 7 | −94.2 | 8 | −92.2 | 6.35 | −94.2 | 6.8 | −93.7 | 8.2 | 5.9 | NA | 2.8 | NA | 1.9 | NA | 1 |
| Ce-2k | −86.1 | 5.4 | −93.3 | 6.2 | −77.8 | 5.05 | −85.6 | 5.4 | −92.0 | 6.4 | 3.4 | NA | 8.5 | NA | 6.9 | NA | 1 |
| Ce-2l | −93.9 | 7.95 | −94.4 | 8.5 | −93.1 | 7.15 | −93.7 | 7.75 | −92.0 | 8.65 | 5.0 | NA | 10.3 | NA | 5.5 | NA | 1 |
| Ce-2m | −94.5 | 7.8 | −94.9 | 8.2 | −94.2 | 6.95 | −96.0 | 7.6 | −95.7 | 8.45 | 6.7 | NA | 3.5 | NA | 0.9 | NA | 1 |
| Ce-2n | −93.4 | 7.91 | −92.9 | 8.46 | −92.4 | 7.11 | −93.4 | 7.63 | −91.4 | 8.67 | 6.3 | NA | 2.4 | NA | −0.4 | NA | 3 |
| Ce-2o | −97.7 | 7.95 | −98.7 | 8.39 | −96.3 | 7.22 | −98.3 | 7.72 | −96.8 | 8.55 | 2.3 | NA | −1.8 | NA | 1.6 | NA | 2 |
| Ce-2p | −93.7 | 7.35 | −92.8 | 7.88 | −92.3 | 6.6 | −93.5 | 7.01 | −90.9 | 8.12 | 6.8 | NA | 5.1 | NA | 3.2 | NA | 1 |
| Ce-2q | −93.1 | 7.43 | −92.7 | 8.19 | −92.0 | 6.67 | −93.1 | 7.08 | −90.0 | 8.51 | 6.0 | NA | 4.5 | NA | 8.1 | NA | 1 |
| Ce-2r | −97.7 | 7.84 | −99.1 | 8.51 | −96 | 7.08 | −97.8 | 7.57 | −98.5 | 8.61 | −2.2 | NA | −2.7 | NA | 5.8 | NA | 2 |
| Ce-2dl | −29.6 | NA | −91.8 | 5.95 | −2.1 | NA | −20.2 | NA | −91.0 | 6.02 | 4.5 | NA | −0.6 | NA | 1.7 | NA | 1 |
| Ce-2bl | −72.0 | 5.37 | −100.3 | 7.06 | −24.3 | NA | −61.1 | 4.49 | −98.7 | 7.07 | −0.4 | NA | 0.1 | NA | 2.2 | NA | 1 |
| Ce-2b2 | −43.2 | NA | −97.0 | 6.35 | 2.2 | NA | −26.0 | NA | −96.6 | 6.38 | 4.4 | NA | 0.5 | NA | 2.9 | NA | 1 |
| Ce-2b3 | −167.4 | NA | −88.3 | 5.9 | 9.5 | NA | −8.9 | NA | −88.4 | 5.95 | 11.5 | NA | 7.9 | NA | 5.7 | NA | 1 |

Example 9

Comparison of N-Terminal L- and D-Amino Acids

Peptides with an N-terminal L- or D-amino acid were synthesized and tested for inhibition of PGM, as described in Example 1. Ce-2 and Ce-2d have N-terminal D-N-chloroacetyl tyrosine, as discussed above. The same peptides, with all L-amino acids (having an N-terminal L-N-chloroacetyl tyrosine (L-Tyr1-Ce2 and L-Tyr1-Ce-2d)) were also tested. As shown in Table 11, the peptides with all L-amino acids retained the majority of the activity of Ce-2 and Ce-2d. No appreciable activity was observed against Homo sapiens or E. coli dPGM.

Example 10

Assessing Effect of Peptides on C. elegans

C. elegans strain N2 (wild type) was used for compound testing. Worms were handled using standard methods. They were cultivated on nematode growth medium (NGM) plates in a 20° C. incubator and fed on living Escherichia coli strain OP50. The E. coli OP50 cells were precultured overnight at 37° C. before spreading on the surface of NGM plates. Synchronous liquid culture of L1 C. elegans obtained through egg bleaching and individual L4 picked from NGM plates under the microscope were used for testing. Either 20 L1 s or 1 L4 were placed in individual wells of 96-well plate in 100 μL of S medium supplied with dead E. coli HB101 as food source. Compounds were added into the well at different concentrations and incubated with worms at 20° C. for up to 7 days. The effect of compounds on worm health was measured by food consumption, development and reproduction. Food consumption was measured by a decline in OD600 nm readings monitored using a SpectraMax M5 microplate reader. Worm development and F1 progeny production were monitored visually under a microscope.

Figure 23B:
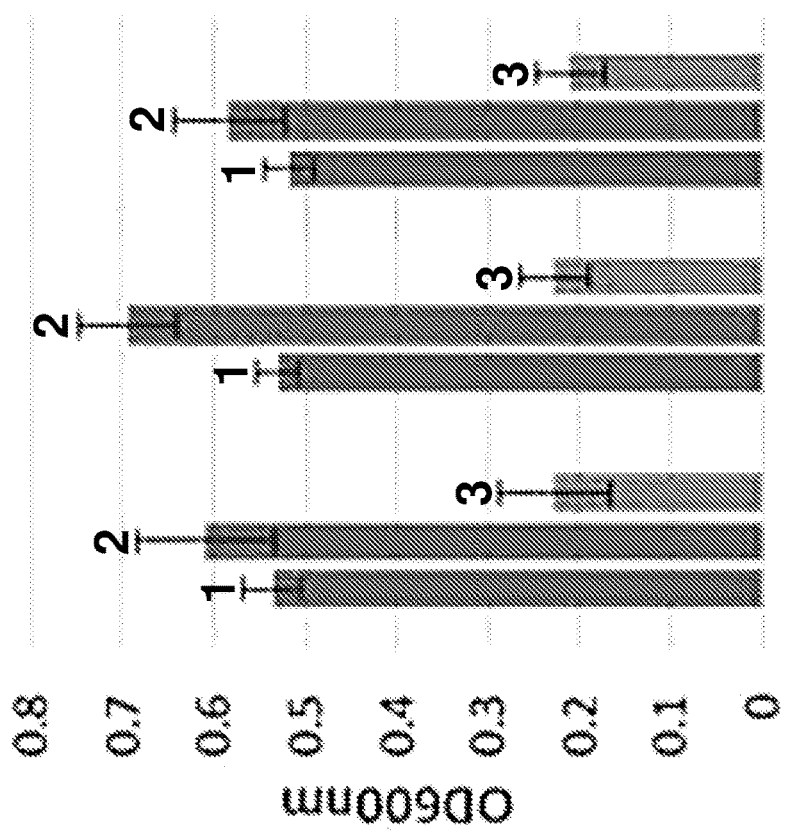
FIGS. 23A-23C are a series of graphs showing Ce-2 and Ce-2d in vivo activity in *C. elegans* culture assay. L1 stage *C. elegans* were exposed to 5 μM (FIG. 23A) or 10 μM (FIG. 23B) Ce-2 or Ce-2d for 1, 2, and 7 days. L4 stage *C. elegans* were exposed to 50 µM Ce-2, 50 µM Ce-2d, or DMSO (FIG. 23C). Data represent mean±s.d. of triplicate samples.
Figure 23A:
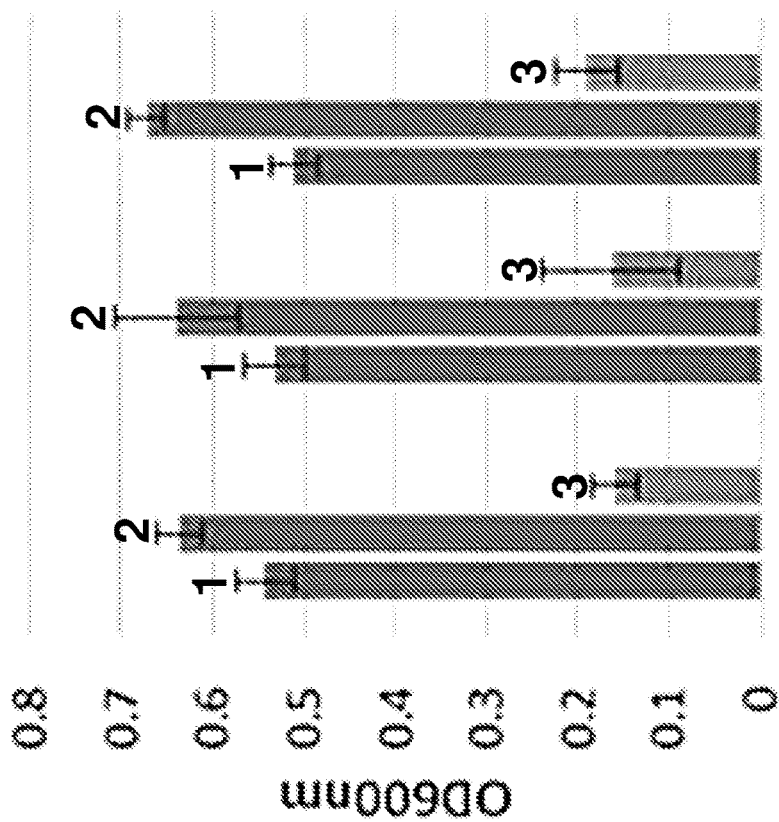

FIGS. 23A and 23B show the effect of exposure of C. elegans to 5 μM or 10 μM Ce-2 or Ce-2d for 1-7 days. Microscopic examination showed slightly decreased numbers of F1 progeny in the presence of the peptide. Exposure

TABLE 11

Inhibitory properties of Ce-2 and Ce-2d analogs

Figure 23C:
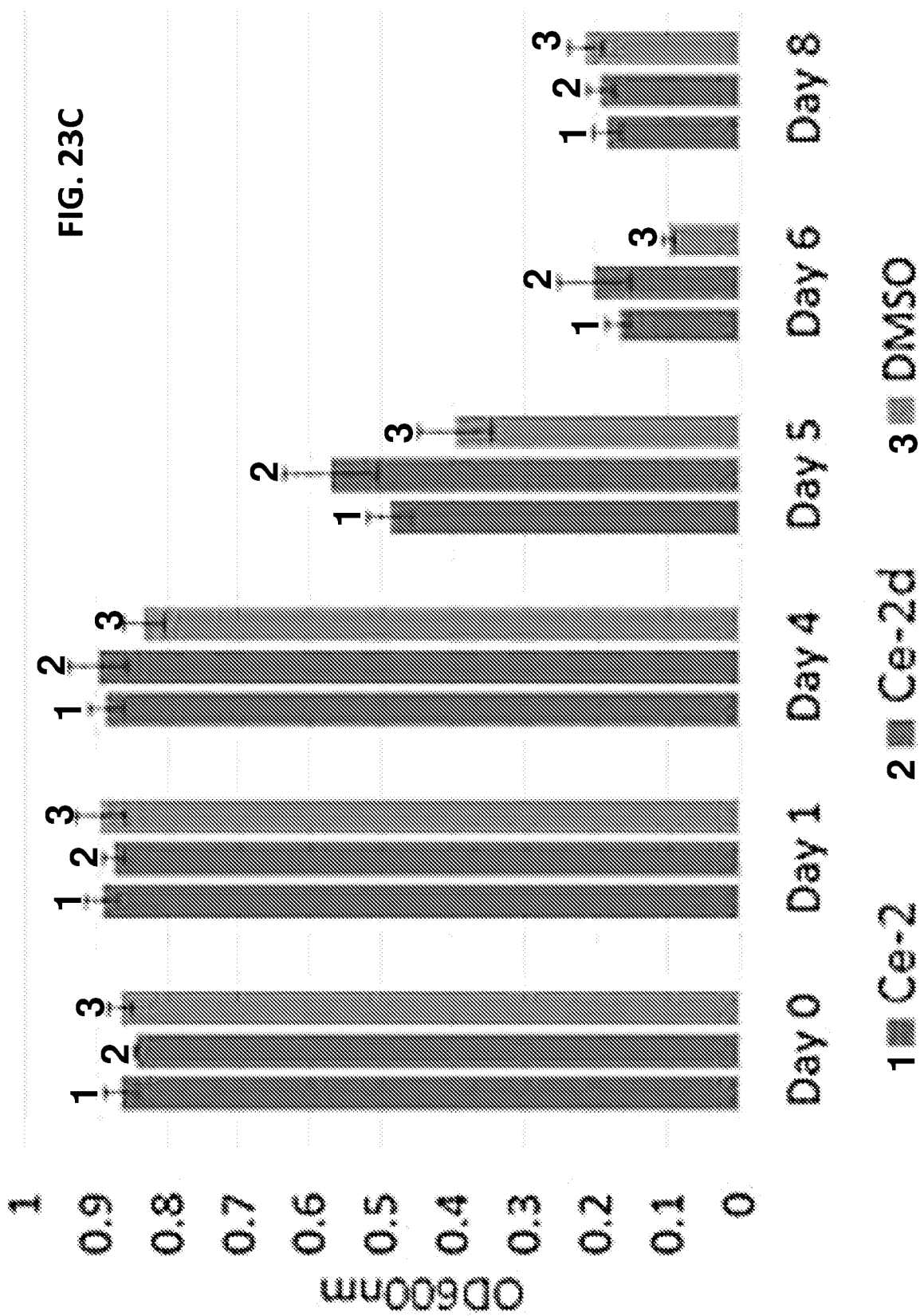

| | C. elegans iPGM (5 nM) | | | E. coli iPGM | | | B. malavi iPGM | | | D. immitis iPGM | | | O. volvulus iPGM | | |
|---|---|---|---|---|---|---|---|---|---|---|---|---|---|---|---|
| | pIC$_{50}$ | M | nM | pIC$_{50}$ | M | nM | pIC$_{50}$ | M | nM | pIC$_{50}$ | M | nM | pIC$_{50}$ | M | nM |
| Ce-2 | 8.63 | 2.34E−09 | 2.34 | 9.64 | 2.32E−10 | 0.23 | 7.78 | 1.68E−08 | 16.76 | 8.22 | 6.03E−09 | 6.03 | 7.63 | 2.35E−08 | 23.49 |
| Ce-2d | 8.41 | 3.88E−09 | 3.88 | 9.12 | 7.67E−10 | 0.77 | 6.83 | 1.48E−07 | 148.4 | 6.82 | 1.52E−07 | 151.8 | 6.42 | 3.83E−07 | 383.4 |
| $^L$Tyr$_1$-Ce-2 | 8.55 | 2.83E−09 | 2.83 | 9.52 | 3.02E−10 | 0.3 | 7.75 | 1.79E−08 | 17.86 | 8.09 | 8.14E−09 | 8.14 | 7.46 | 3.43E−08 | 34.34 |
| $^L$Tyr$_1$-Ce-2d | 7.86 | 1.40E−08 | 14 | 8.24 | 5.76E−09 | 5.76 | 6.02 | 9.49E−07 | 949 | 6.01 | 9.89E−07 | 989 | 5.73 | 1.85E−06 | 1,853 | iPGMs: Ce, 5 nM C. elegans; Ec, 10 nM E. coli; Bm, 5 nM B. malavi; Di, 10 nM D. immitis; Ov, 15 nM O. volvulus; dPGMs to 50 µM peptide showed little effect on the adult stage (FIG. 23C). Though little in vivo efficacy was observed with these two peptides, other peptides, modes of administration, or alternative culturing conditions (e.g. axenic growth conditions) more closely mimicking that of parasitic species may have greater effects.

Example 11

Additional Assessment of Peptide Effect on *C. elegans*

*C. elegans* are handled and cultivated as described in Example 10. Compounds are microinjected in *C. elegans* using standard techniques. Worm development and F1 progeny production are monitored as described in Example 9. Active compounds are identified by impacts on development, worm viability (e.g., decreased viability), and progeny production.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An isolated cyclic peptide comprising the amino acid sequence of any one of SEQ ID NOs: 1-6, 10-20, or 55-69 wherein the peptide includes an N-terminal ring structure of 7-13 amino acids and a C-terminal linear portion of 1-7 amino acids, wherein the N-terminal ring structure comprises a thioether linkage, or a pharmaceutically acceptable salt or ester thereof.

2. The isolated cyclic peptide of claim 1, wherein the peptide comprises:

(a)
$Ac-D$YDYPGDYCYLYGTCG; (SEQ ID NO: 2)

(b)
$Ac-D$YDYPGDYCYLYGTC; (SEQ ID NO: 17)

(c)
$Ac-D$YDYPGDYCYLY; (SEQ ID NO: 5)

(d)
$Ac-D$YDYPGDHCYLYGTCG; (SEQ ID NO: 1)

(e)
$Ac-L$YITLANPFRILHCG; (SEQ ID NO: 3)

(f)
$Ac-L$YTTLANPFRILHCG; (SEQ ID NO: 4)

(g)
$Ac-D$YDYPGDYCYLYGTSG; (SEQ ID NO: 6)

(h)
$Ac-D$YSWPNAPEIWKCCG; (SEQ ID NO: 10)

(i)
$Ac-D$YDLRTPWLKRHACG; (SEQ ID NO: 11)

(j)
$Ac-D$YQNRSIWLYGCCG; (SEQ ID NO: 12)

(k)
$Ac-D$YLEWPNCNTCG; (SEQ ID NO: 13)

(l)
$Ac-D$YLDWPNCSTCG; (SEQ ID NO: 14)

(m)
$Ac-D$YPEWPNCSTCG; (SEQ ID NO: 15)

(n)
$Ac-D$YAVWPNCRTCG; (SEQ ID NO: 16)

(o)
$Ac-D$YDYPGDYCYCLYGT; (SEQ ID NO: 18)

(p)
$Ac-D$YDYPGDYCYLYG; (SEQ ID NO: 19)

(q)
$Ac-D$YDYPGDYCYL; (SEQ ID NO: 20)

(r)
$Ac-D$YDYPGDYC$^{Me}$YLYGTCG; (SEQ ID NO: 55)

(s) 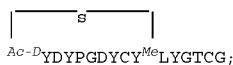 (SEQ ID NO: 56)

(t)  (SEQ ID NO: 57)

(u) 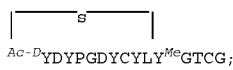 (SEQ ID NO: 58)

(v) 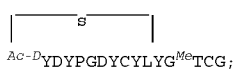 (SEQ ID NO: 59)

(w) 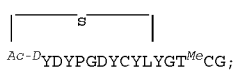 (SEQ ID NO: 60)

(x) 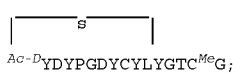 (SEQ ID NO: 61)

(y)  (SEQ ID NO: 62)

(z)  (SEQ ID NO: 63)

(aa)  (SEQ ID NO: 64)

(bb) 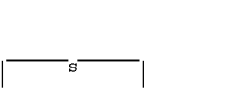 (SEQ ID NO: 65)

(cc)  (SEQ ID NO: 66)

(dd)  (SEQ ID NO: 67)

(ee) 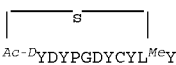 (SEQ ID NO: 68)

(ff) 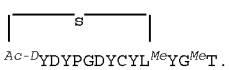 (SEQ ID NO: 69)

3. The isolated cyclic peptide of claim 1, wherein at least one amino acid is a D-amino acid.

4. The isolated cyclic peptide of claim 3, wherein the N-terminal amino acid is a D-amino acid.

5. The isolated cyclic peptide of claim 1, wherein the thioether linkage is between an N-terminal acetyl group and a cysteine residue.

6. The isolated cyclic peptide of claim 1, wherein the peptide comprises a C-terminal amide.

7. The isolated cyclic peptide of claim 1, wherein the peptide comprises at least one N-methyl amide in the linear portion of the peptide.

8. The isolated peptide of claim 1, wherein the peptide inhibits activity of cofactor-independent phosphoglycerate mutase with an $IC_{50}$ of 100 μM or less.

9. The isolated peptide of claim 8, wherein the peptide inhibits activity of cofactor-independent phosphoglycerate mutase with an $IC_{50}$ of 1 pM to 100 μM.

10. A pharmaceutical composition comprising the isolated peptide of claim 1 and a pharmaceutically acceptable carrier.

11. A method of treating or inhibiting infection with an organism expressing at least one cofactor-independent phosphoglycerate mutase in a subject, comprising administering to the subject an effective amount of the pharmaceutical composition of claim 10.

12. A method of treating or inhibiting infection with an organism expressing at least one cofactor-independent phosphoglycerate mutase in a subject, comprising administering to the subject an effective amount of the isolated peptide of claim 1.

13. The method of claim 12, wherein the subject is infected with an organism selected from the group consisting of a nematode, a trypanosome, a helminth, and a protozoan parasite.

14. The method of claim 13, wherein the subject is infected with a nematode, and the nematode comprises one or more of *Brugia malayi*, *Brugia timori*, *Wuchereria bancrofti*, *Onchocerca volvulus*, *Loa loa*, *Mansonella streptocerca*, *Mansonella perstans*, *Mansonella ozzardi*, *Dirofilaria immitis*, *Trichinella*, *Parafilaria bovicola*, *Onchocerca dermatan*, *Onchocerca ochengi*, *Onchocerca dukei*, *Stenofilaria assamensis*, and *Parafilaria multipapillosa*.

15. The method of claim 12, wherein the peptide is administered orally, intravenously, or topically.

16. The method of claim 12, further comprising administering one or more of an antiparasitic or antibiotic agent to the subject.

* * * * *